US007510834B2

(12) United States Patent
Inoko et al.

(10) Patent No.: US 7,510,834 B2
(45) Date of Patent: Mar. 31, 2009

(54) GENE MAPPING METHOD USING MICROSATELLITE GENETIC POLYMORPHISM MARKERS

(75) Inventors: Hidetoshi Inoko, 19-35, Ryokuen 1-chome, Izumi-ku, Yokohama-shi, Kanagawa-ken (JP) 245-0002; Gen Tamiya, Isehara (JP)

(73) Assignees: Hidetoshi Inoko, Kanagawa-ken (JP); Tokai University, Tokyo-to (JP)

( * ) Notice: Subject to any disclaimer, the term of this patent is extended or adjusted under 35 U.S.C. 154(b) by 10 days.

(21) Appl. No.: 10/674,124

(22) Filed: Sep. 26, 2003

(65) Prior Publication Data
US 2004/0197797 A1    Oct. 7, 2004

Related U.S. Application Data

(63) Continuation-in-part of application No. 10/257,511, filed as application No. PCT/JP00/07621 on Oct. 30, 2000.

(30) Foreign Application Priority Data

Apr. 13, 2000  (JP)  .............................. 2000-112699
Sep. 28, 2002  (JP)  .............................. 2002-327516
Dec. 9, 2002   (JP)  .............................. 2002-383869

(51) Int. Cl.
*C12Q 1/68*   (2006.01)
*C12P 19/34*  (2006.01)
*C07H 21/02*  (2006.01)
*G01N 33/48*  (2006.01)

(52) U.S. Cl. .......................... 435/6; 435/91.2; 536/23.1; 536/24.3

(58) Field of Classification Search ........................ None
See application file for complete search history.

(56) References Cited

U.S. PATENT DOCUMENTS 5,683,880 A * 11/1997 Kamb ........................... 435/6
2004/0038272 A1  2/2004 Jou et al.

FOREIGN PATENT DOCUMENTS

WO   WO 94/25625   11/1994
WO   WO 97/31011   8/1997
WO   WO 02/50307   6/2002

OTHER PUBLICATIONS

Barcellos, 1997, Am. J. Hum. Genet., vol. 61, pp. 734-747.*
Braun, 1997, Genomics, vol. 46, pp. 18-23.*
Zhao S et al 'Human, mouse, and rat genome large-sclae rearrangements: stability versus speciation.' Genome Res. Oct. 2004;14(10A):1851-60.*
Adb-Elsalam 'Bioinformatic tools as guidelines for PCR primer design' African Journal of Biotechnology, vol. 2 (5) pp. 91-95.*

Barcellos, et al., "Association mapping of disease loci, by use of a pooled DNA genomic screen," American Journal of Human Genetics, (1997) vol. 61, No. 3, pp. 734-747.
Cox T C et al., "A very high density microsatellite map (1 STR/41 kb) of 1.7 Mb on Xp22 spanning the microphthalmia with linear skin defects (MLS) syndrome critical region," European Journal of Human Genetics: EJHG. England Jul.-Aug. 6, 1998 pp. 406-412.
GenBank Accession No. AF003650 Homo sapiens clone CxM18 MLS syndrome critical region microsatellite sequence, sequence tagged site (Jan. 5, 1999).
Gyapay, et al., "The 1993-94 genethon human genetic linkage map," Nature Genetics, US (Jun. 1994) vol. 7, No. 1, pp. 246-339.
Van Heel, et al., "Identification of novel polymorphisms in the β7 integrin gene: family-based association studies in inflammatory bowel disease," Genes and Immunity (2001) vol. 2, No. 8, pp. 455-460.
Immervoll, et al., "Fine mapping and single nucleotide polymorphism association results of candidate genes for asthma and related phenotypes," Human Mutation (2001) vol. 18, No. 4, pp. 327-336.
Hirota, et al., "Genome-wide microsatellite association studies for parkinson's disease by using the pooled DNA method," American Journal of Human Genetics, (Nov. 2003) vol. 73, No. 5, p. 469 Abstract 1754.
Shiina, et al., "Molecular dynamics of MHC genesis unraveled by sequence analysis of the 1,796,938-bp HLA class I region," Proceedings of the National Academy of Sciences of the United States of America. US, (Nov. 9, 1999) vol. 96, No. 23, pp. 13282-13287.
Shiozawa, et al., "Identification of the gene loci that predispose to rheumatoid arthritis," International Immunology, (Dec. 1998) vol. 10, No. 12, pp. 1891-1895.
Yoshikawa, et al., "An efficient application of maldi-tof/ms coupled with microarray for detection of microsatellite polymorphism," American Journal of Human Genetics, (Oct. 2001) vol. 69, No. 4, p. 464, Abstract 1651.
Oka, et al., "Association analysis using refined microsatellite markers localizes a susceptibility locus for psoriasis vulgaris within a 111 kb segment telomeric to the HLA-C gene", Human Molecular Genetics, vol. 8, No. 12, pp. 2165-2170, 1999.
Keicho, et al., "Fine localization of a major disease-susceptibility locus for diffuse panfronchiolitis", Am. J. Hum. Genet., vol. 66, pp. 501-507, 2000.
Kimura, et al., "Mapping of the HLA-linked genes controlling the susceptiiblity to Takayasu's arthritis", International Journal of Cardiology, vol. 75, pp. S1QS-S110, 2000.

(Continued)

*Primary Examiner*—Jehanne S Sitton
*Assistant Examiner*—Stephen Kapushoc
(74) *Attorney, Agent, or Firm*—Carol L. Francis; Bozicevic, Field & Francis LLP

(57) ABSTRACT

The present invention provides a gene mapping method which involves analysis of a DNA sample from a test subject and from a control subject for the presence of an allelic form of a plurality of microsatellite genetic polymorphism marker, which markers are located at intervals of about 50 Kb to 150 Kb on the human genome, in order to identify regions of the genome associated with a characteristic of the test subjects relative to the control subjects, e.g., a region containing a pathogenic gene or a gene relating to human phenotypes with genetic factors. The invention also features genomic regions so identified that are associated with susceptibility or the presence of psoriasis vulgaris and with rheumatoid arthritis.

7 Claims, 26 Drawing Sheets

OTHER PUBLICATIONS

Mizuki, et al., "Localization of the Pathogenic Gene of Behget's Disease by Microsatellite Analysis AV of Three Different Populations", Invest. Ophthalmol Vis Sci. vol. 41, No. 12, pp. 3702-3708, Nov. 2002.

Matsuzaka, et al., "New polymorphic microsatellite markers in the human MHC class II region", Tissue Antigens, vol. 56, pp. 492-500, 2000.

Ota, et al., "A Second Susceptibility Gene for Developing Rheumatoid Arthritis in the Human MHC AX is Localized within a 70-kb Interval Telomeric of the TNF Genes in the HLA Class III Region", Genomics. vol. 71, pp. 263-270, 2001.

Mizuki, et al., "Microsatellite Mapping of a Susceptible Locus Within the HLA Region for Beliefs Disease Using Jordanian Patients", Human Immunology., vol. 62, pp. 186-190, 2001.

Matsuzaka, et al., "Identification of novel candidate genes in the diffuse panbronchiolitis critical region of the class I human MHC", Immunogenetics. vol. 54, pp. 301-309, 2002.

Matsuzaka, et al., "Susceptibility locus for non-obstructive azoospermia is localized within the H*LA-DR/DQ* subregion: Primary role of *DQBI\*0604*", Tissue Antigens. vol. 60, pp. 53-63, 2002.

Niizeki, et al., "Polymorphisms in the TNF region confer susceptibility to UVB-induced impairment of contact hypersensitivity induction in mice and humans", Methods, vol. 28, pp. 46-54, 2002.

Oka, et al., "Identification of psoriasis vulgaris-susceptible gene within HLA class I antigen", The 22nd Annual meeting Pf MBSJ, IP-1334, Nov. 22, 1999.

* cited by examiner

7th Chromosome

9th Chromosome

10th Chromosome

11th Chromosome

12th Chromosome

15th Chromosome

18th Chromosome

21st Chromosome

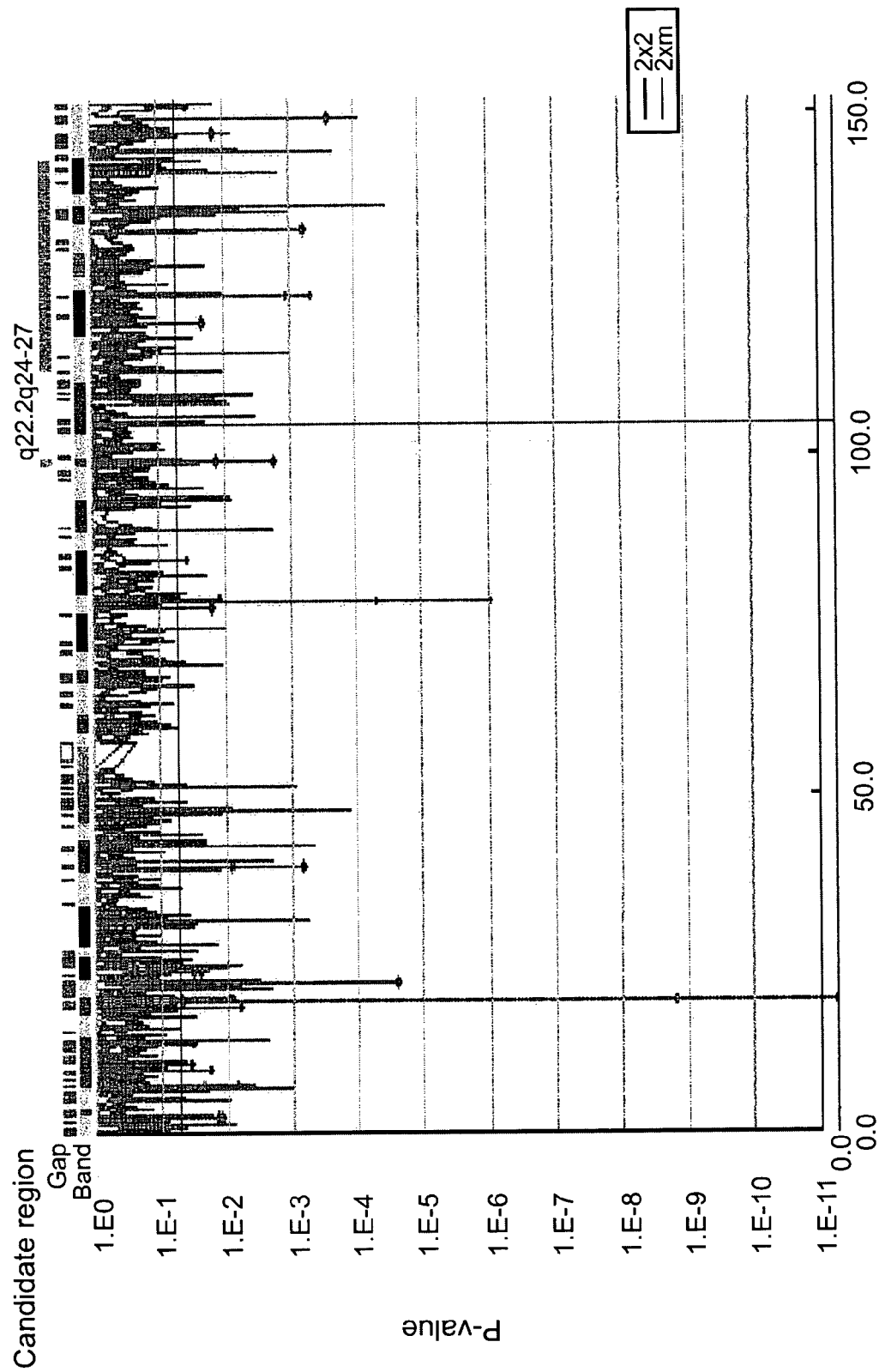

GENE MAPPING METHOD USING MICROSATELLITE GENETIC POLYMORPHISM MARKERS

CROSS-REFERENCE TO RELATED APPLICATIONS

This application
1) is a continuation-in-part of U.S. application Ser. No. 10/257,511, filed, Mar. 7, 2003, which application is a §371 national phase application of PCT/JP00/07621, filed Oct. 30, 2000, which application claims the priority benefit of Japanese patent application serial no. 2000-112699, filed Apr. 13, 2000; and
2) claims the benefit of Japanese patent application serial no. 2002-327516, filed Sep. 28, 2002, and claims the benefit of Japanese patent application serial no. 2002-383869, filed Dec. 9, 2002;

each of which application is incorporated herein by reference in its entirety.

SEQUENCE LISTING

The present specification incorporates herein by reference, each in its entirety, the sequence information on the Compact Disks (CDs) labeled Copy 1 and Copy 2. The CDs are formatted on IBM-PC, with operating system compatibility with MS-Windows. The files on each of the CDs are as follows:
Copy 1—Seqlist.txt 23.250 MB created May 19, 2004; and
Copy 2—Seqlist.txt 23.250 MB created May 19, 2004;
where "N" appears in a nucleotide sequence, N=A, T, C, or G.

FIELD OF THE INVENTION

The present invention relates to methods for gene mapping using microsatellite genetic polymorphism markers. In particular, it relates to a gene mapping method, which uses a distribution map indicating the nucleotide sequences and location of each DNA sequence in a group of DNA sequences including microsatellite genetic polymorphism markers that are located on the human genome.

BACKGROUND OF THE INVENTION

Mapping of pathogenic genes or genes expressing specific phenotypes has been accomplished prior to the invention by comparing the genetic polymorphism markers in test subjects and those in control subjects, and then determining whether there is difference between the frequencies of scific alleles in the test and control subjects.

Such methods of analysis of genetic polymorphism markers include detection of restriction fragment length polymorphisms (RFLP); detection of a variable number of tandem repeats (VNTR) which are scatter within the human genome; detection of the presence or absence of microsatellites markers; and detection of the presence or absence of single nucleotide polymorphisms (SNPs). In particular, methods involving detection of SNPs and microsatellites have attracted attention.

However, there are problems with use of SNPs as the genetic polymorphism markers. For example, because the SNPs are single nucleotide replacements on a genome, generally only two alleles exist, and further only those SNPs existing within 5 kb to 10 kb from to be-mapped genes correlate with the gene. Therefore, genome mapping performed using the SNPs as the genetic polymorphism markers requires an enormous amount of SNPs as markers and an analysis thereof.

Microsatellites avoid some of the problems of SNPs. Many alleles exist for a microsatellite genetic polymorphism markers, and microsatellite markers show correlation to a gene even when it is positioned somewhat far from the gene to be mapped. However, use of microsatellite markers is problematic where there are many microsatellite genetic polymorphism markers used, analysis becomes becomes difficult in terms of tremendous time and labor. In addition, when too few microsatellite markers are used, correlation cannot be found and thus causative genes may be overlooked.

Currently, the field is focusing on specifying a genetic mechanism that defines individual phenotypes through collection and comparison of genetic polymorphism information on a group of subjects, and identifying the susceptibility gene for hereditary diseases with multiple factors or phenotypes. However, the conventional methods utilizing microsatellites or SNPs can work for only limited regions and genes in the human genome, and even for the entire chromosome, only low resolution methods can be used. Therefore, there are many cases of neither being able to identify the susceptibility gene nor eliminate the possibility that other genes are involved even if that identification is successful.

There is a need in the field for methods of gene mapping that address these problems. The present invention addresses this need.

SUMMARY OF THE INVENTION

The present invention provides a gene mapping method which involves analysis of a DNA sample from a test subject and from a control subject for the presence of an allelic form of a plurality of microsatellite genetic polymorphism marker, which markers are located at intervals of about 50 Kb to 150 Kb on the human genome, in order to identify regions of the genome associated with a characteristic of the test subjects relative to the control subjects, e.g., a region containing a pathogenic gene or a gene relating to human phenotypes with genetic factors. The invention also features genomic regions so identified that are associated with susceptibility or the presence of psoriasis vulgaris and with rheumatoid arthritis.

An objective of the present invention is to provide a genome polymorphism analysis method, which does not have the same defects as in the gene mapping methods utilizing the SNPs or microsatellites as described above and allows clear identification of the genetic mechanism that defines individual phenotypes through collection and comparison of genetic polymorphism information on a group.

Furthermore, an objective of the present invention is to provide a protein, which is encoded by a gene that is identified by the genome polymorphism analyzing method, and antibodies against the protein.

The present invention further provides a forward primer, which has a length of, for example, about 15 to 100 nucleotides, and which can be used for detection of a microsatellite genetic polymorphism, e.g, the forward primer has a nucleotide sequence that is the same as, a nucleotide sequences extending in the 3'-direction from the 5'-terminus of the DNA sequence of a microsatellite genetic polymorphism marker located on the human genome.

Furthermore, the present invention provides a reverse primer, which has a length of, for example, about 15 to 100 nucleotides, and which can be used for detection of a microsatellite genetic polymorphism, e.g., the reverse primer has a nucleotide sequence that is complementary to the sequence extending in the 5'-direction from the 3'-terminus of the DNA sequences of a microsatellite genetic polymorphism markers that are located on the human genome.

Furthermore, the present invention provides a distribution map for the DNA sequences including microsatellite genetic polymorphism markers, which indicate the nucleotide sequences and location in each DNA sequence of a group of DNA sequences including microsatellite genetic polymorphism markers that are located on the human genome at intervals of 50 Kb to 150 Kb. The distribution map can be provided in, for example, in computer-readable format (e.g., embedded in a computer readable media), for access by a computer, which can be programmed to facilitate analysis of the distribution map.

Other features and advantages of the invention will be apparent to the ordinarily skilled artisan upon reading the disclosure provided herein.

BRIEF DESCRIPTION OF THE DRAWINGS

FIG. 26 shows a profile for the rheumatism susceptibility segment in the Y chromosome analyzed using a method according to the present invention.

DEFINITIONS, ABBREVIATIONS OF TERMINOLOGY, AND DESCRIPTION OF TERMINOLOGY

Figure 1:
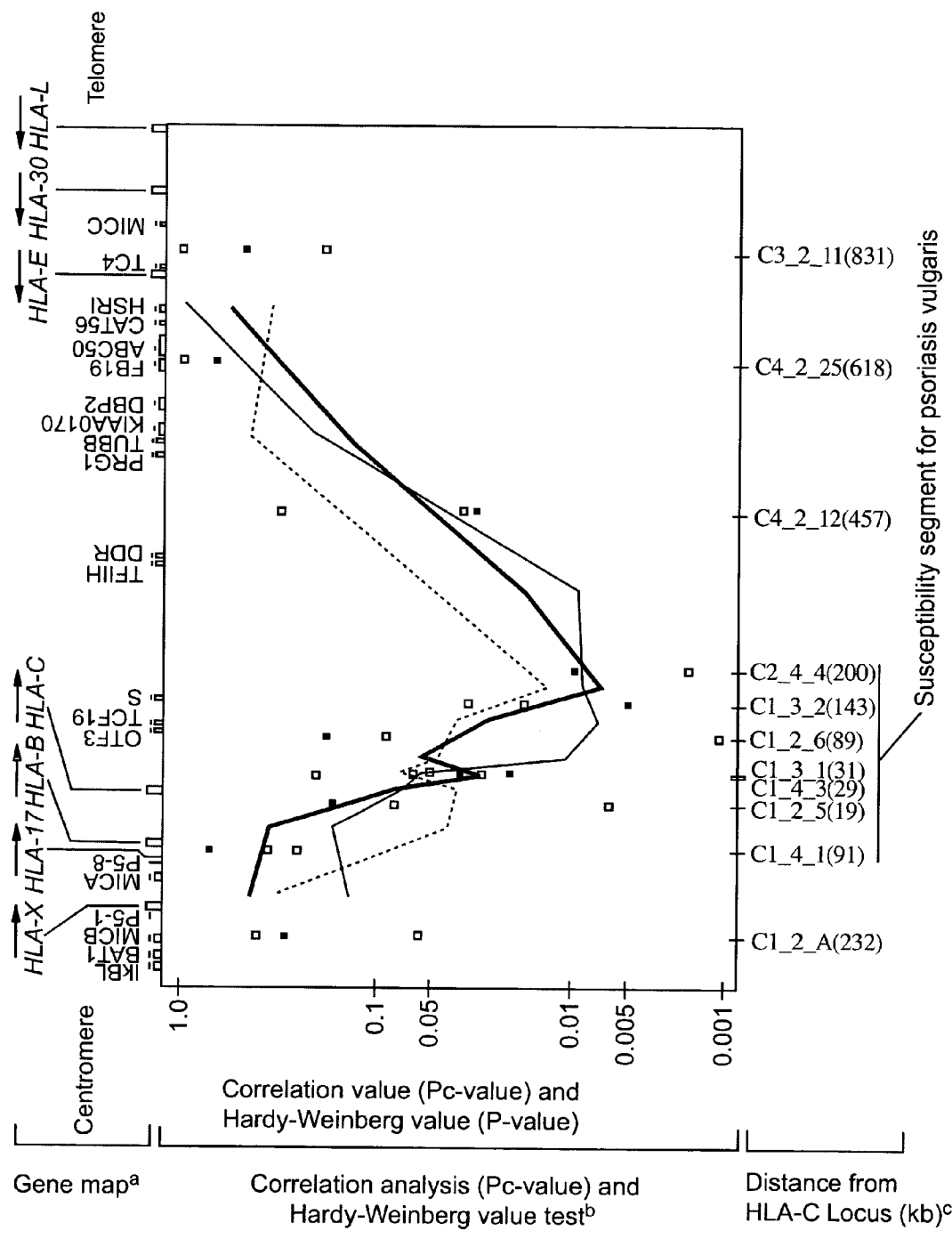
FIG. 1 indicates P-values obtained by the correlation test and the exact test of Hardy-Weinberg proportion with the locations of microsatellite markers used for gene mapping of psoriasis vulgaris.

The term "forward primer" herein denotes a primer having the same nucleotide sequence as the sequence extending in 3'-directions from the 5'-terminus and may include part of the sequence of the 5' terminus, of the DNA sequence encoding the microsatellite genetic polymorphism markers that are located on human genome.

The term "reverse primer" herein denotes a primer having a complementary nucleotide sequence to a sequence extending in 5'-directions from the 3'-terminus, and may include part of the sequence of complementary to the 3' terminus, of the DNA sequence encoding the microsatellite genetic polymorphism markers that are located on human genome.

The term "distribution map" herein denotes a map indicating the distribution of DNA sequences including microsatellite genetic polymorphism markers, which are used to indicate the nucleotide sequences and location in each DNA sequence of a group of DNA sequences including microsatellite genetic polymorphism markers that are located on the human genome in desired intervals. As a group of DNA sequences including the genetic polymorphism markers, a group of DNA sequences composed of the nucleotide sequences referred to with SEQ ID NOS: 1 to 27088 are described herein. The distribution map can be provided in, for example, in computer-readable format (e.g., embedded in a computer readable media), for access by a computer, which can be programmed to facilitate analysis of the distribution map.

It is noted that the nucleotide sequences having the sequence of SEQ ID NOS: 1 to 27088 are located on the human chromosome as shown below. The numbers to the right of "autosome" denote sequence numbers.

The first autosome: SEQ ID NOS:1 to 2203
The second autosome: SEQ ID NOS:2204 to 4561
The third autosome: SEQ ID NOS:4562 to 6438
The fourth autosome: SEQ ID NOS:6439 to 8005
The fifth autosome: SEQ ID NOS:8006 to 9641
The sixth autosome: SEQ ID NOS:9642 to 11422
The seventh autosome: SEQ ID NOS: 11423 to 13352
The eighth autosome: SEQ ID NOS:13353 to 14629
The ninth autosome: SEQ ID NOS:14630 to 15734
The tenth autosome: SEQ ID NOS:15735 to 17011
The eleventh autosome: SEQ ID NOS:17012 to 18202
The twelfth autosome: SEQ ID NOS:18203 to 19560
The thirteenth autosome: SEQ ID NOS:19561 to 20427
The fourteenth autosome: SEQ ID NOS:20428 to 21178
The fifteenth autosome: SEQ ID NOS:21179 to 21732
The sixteenth autosome: SEQ ID NOS:21733 to 22478
The seventeenth autosome: SEQ ID NOS:22479 to 23137
The eighteenth autosome: SEQ ID NOS:23138 to 23801
The nineteenth autosome: SEQ ID NOS:23802 to 24313
The twentieth autosome: SEQ ID NOS:24314 to 24953
The twenty-first autosome: SEQ ID NOS:24954 to 25307
The twenty-second autosome: SEQ ID NOS:25308 to 25634
X chromosome: SEQ ID NOS:25635 to 26697
Y chromosome: SEQ ID NOS:26698 to 26801
Not identified locations: SEQ ID NOS:26802 to 27088

The abbreviation "MS genetic polymorphism marker sequence" or "MS marker sequence" herein denotes a DNA sequence including a microsatellite genetic polymorphism marker.

"Genetic polymorphism" herein indicates that two or more forms of an allele exist on a particular gene locus with a frequency greater than 1%. A gene locus may be any region on the genome, and is not limited to the genetic region which is expressed.

The term "microsatellite" denotes a sequence having di- to hexanucleotide repeats. The microsatellites are known to exist at a frequency of one in 2 kb to 3 kb on the genome. The number of repeats within each microsatellite may vary among individuals.

A short tandem repeat (STR) refers to a short sequence that varies between alleles by the number of repeats of the sequence present, e.g., the polymorphism is due to variation in the number of repeats across different allelic forms. Genetic polymorphisms of microsatellites are generally determined by the number of repeats therein. A representative example of such microsatellites is the CA repeat (Dib C. et al. (1966) Nature, 380: 152-154).

For example, according to microsatellite analyses in the human HLA region made by the present inventors, microsatellites with dinucleotide repeats were found at a rate of one in approximately 8.9 kb; with trinucleotide repeats, one in approximately 12.9 kb; with tetranucleotide repeats, one in approximately 6.6 kb; with pentanucleotide repeats, one in approximately 12.6 kb; in total, one microsatellite in approximately 2.4 kb (Shiina T. et al. (1999) Proc. Natl. Acad. Sci. USA, 96: 13282-13287).

With this invention, these microsatellites are appropriately selected and used as genetic polymorphism markers. According to the present invention, a microsatellite marker for mapping a genomic locus are selected, and a distribution map for DNA sequences including microsatellite genetic polymorphism markers can be generated. The map indicates the nucleotide sequence and location in each DNA sequence within of a group of DNA sequences that including microsatellite genetic polymorphism markers located on the human genome in intervals of 50 to 150 Kb, preferably 80 to 120 Kb, more preferably 90 to 110 Kb, is made and utilized.

In one aspect of the invention, the inventors generated such a distribution map of region on the human genome, a where a group of DNA sequences including microsatellite genetic polymorphism markers on the human genome are a group of DNA sequences made up of nucleotide sequences referenced with sequence numbers 1 to 27088. The sequence table with the sequence numbers shows chromosome numbers for the respective DNA sequences, locations on the chromosomes, and distances from before and after each DNA sequence.

It is noted that "additional information" (<223>) in the Sequence Listing provided on CD-ROM, and intended as part of the present specification, provides information about the location and characteristics of the marker. Examples of such descriptions are set out below.

"<223> Marker ID" in the Sequence Listing denotes a specific marker symbol. This specific symbol is an identification symbol attached to each microsatellite genetic marker by the applicant; which can be used in implementing the present invention and obtaining additional experimental data if necessary.

"<223> Located on chromosome" in the Sequence Listing denotes a location on a chromosome. For example, "<223> Located on chromosome 17" means that a corresponding nucleotide sequence exists on the seventeenth chromosome.

"<223> Distance between a terminus base of telomere on chromosomal short arm and 5'-terminus of this base sequence:" in the Sequence Listing means the distance between the very end base of the telomeric short arm of a chromosome and corresponding base sequence 5'-terminus. For example, "<223> Distance between a terminus base of telomere on chromosomal short arm and 5'-terminus of this base sequence: 72160696", this means that the distance between a terminus base of the chromosomal telomeric short arm and the 5'-terminus of this base sequence is equal to 72160696 nucleotides.

"<223> Distance between 3'-terminus of neighbour sequence of sequence listing upward to telomere on chromosomal short arm and the 5'-terminus of this base sequence: 107571" in the Sequence Listing means that the distance between the 3'-terminus of the neighbour sequence located on the chromosomal telomeric short arm, which is listed in the sequence table, and the 5'-terminus of this base sequence. For example, "<223> Distance between the 3'-terminus of neighbour sequence of sequence listing upward to telomere on chromosomal short arm and the 5'-terminus of this base sequence: 107571" means that the distance between the 3'-terminus of the neighbour sequence (appricon) positioned on the chromosomal telomeric short arm and the 5'-terminus of this base sequence is equal to 107571 nucleotides. It is noted that when this number is "0", this means that there is no neighbour sequence.

It is further noted that the MS genetic polymorphism markers are provided over a genomic region such that they exist at a rate of one to approximately 100 kb on the genome. This emanates from the fact that the microsatellites located within the range between 100 Kb and 200 Kb from a target gene indicate linkage disequilibrium, and that correlation with phenotypes such as diseases is found by mapping, thereby allowing identification of the target gene region. That is, since the microsatellite genetic polymorphism located 100 kb to 200 kb from the causative gene indicates linkage disequilibrium, the distribution map for MS genetic polymorphism markers located at a rate of one in approximately 100 kb can be used to to reliably detect the correlation without overlooking a causative gene and conduct most effective causative gene mapping with minimum labor.

With this invention, a rate of one in approximately 100 kb usually means an average rate of one in 50 kb to 150 kb, preferably one in 80 kb to 120 kb on average, and more preferably one in 90 kb to 110 kb on average, over a genomic region of interest, e.g., over a gene (e.g., including introns and exons), genetic locus (e.g., a region containing one or more genes), or one or more chromosomes.

With this invention, the phrase "substantially located at a rate of one in approximately 100 kb" refers not only to the case where the MS genetic polymorphism markers are located at a rate of one in approximately 100 kb throughout the entire region, but also the case where some of the markers are located at a rate of one in approximately 100 kb. For example, when MS genetic polymorphism markers are located at a rate of one in approximately 100 kb in a certain region, and markers are located at a different frequency in another region, then as a whole it does not satisfy the ratio of "one in approximately 100 kb", however, as long as the MS genetic polymorphism markers are located in a certain region at a rate of one in approximately 100 kb, it is included in the definition of "substantially located at a rate of one in approximately 100 kb" according to this invention.

Incidentally, if three or more MS genetic polymorphism markers are prepared, the ratio thereof can be calculated; however, locating 5 or more is favorable to calculate that rate, more preferably 7 or more, and still more preferably 10 or more.

Moreover, to make a distribution map for MS genetic polymorphism markers, which are used for gene mapping, the MS genetic polymorphism markers to be prepared preferably have high information content available for analysis. The larger the allele number, for example, or the higher the heterozygosity, the higher information content available for the analyses.

The "allele number" indicates the number of alleles of a certain gene, according to the present invention. That is, genomic sequences at a specific gene locus having different nucleotide sequences are referred to as having an "allelic" relationship; the term corresponds to genotype, and the number thereof is referred to as the allele number.

The term "average allele number" refers to the average allele number of all microsatellites used in the mapping method of this invention. Provided that the allele numbers of the 1 st to the n-th microsatellite are denoted as m1 to mn, respectively, the average allele number of n microsatellites is expressed by the following equation:

Average allele number: $(m_1+m_2+m_3+ \ldots +m_n)/n$

The term "heterozygous" refers to the state of a gene in diploid organisms, such as humans, having different alleles on the two strands of chromosomes. Further, the term "heterozygosity" denotes the degree of heterozygosity. When the allele number of the x-th microsatellite is denoted as $m_x$, and the frequency of each allele $Fm_1$ to $Fm_x$, respectively, "heterozygosity ($h_x$)" of that microsatellite is given by the following equation:

$$h_x = 1-(Fm_1^2+Fm_2^2+Fm_3^2+ \ldots +Fm_x^2)$$

The "average heterozygosity" of n microsatellites is given by the following equation:

Average heterozygosity: $(h_1+h_2+h_3+ \ldots +h_n)/n$

Use of a genetic polymorphic marker having an average allele number of 5 or more, or preferably 8 or more, and an average heterozygosity of 60% or more, preferably 65% or more, or more preferably 70% or more, provides for more efficient mapping.

Gene mapping according to the present invention is generally conducted by comparing the frequency of MS genetic polymorphic markers in healthy control subjects to that in randomly selected affected patients. That is, the frequency of each allele of microsatellites in healthy control subjects and the frequency of each allele of microsatellites in randomly selected affected patients are compared by correlation analysis.

Herein, "randomly selected" indicates that the selected patients do not have to have a blood relation (siblings or filioparental relationship). It is preferable that the group of patients consists of patients without blood relation (siblings or filioparental relationship) to each other. If a microsatellite is within 100 kb to 200 kb from a pathogenic gene, the frequency of each allele of that microsatellite will be statistically different between healthy subjects and affected patients. A correlation analysis can be performed based on a known method (Nishimura Y. (1991) "Takei no Tokeigakuteki Riyoho" (Statistical Utilization of Polymorphisms), Saishin Igaku 46: 909-923; Oka A. et al. (1999) Hum. Mol. Genetics, 8: 2165-2170 (1999); Ota M. et al. (1999) Am. J. Hum. Genet. 64: 1406-1410 (Ozawa A. et al. (1999) Tissue Antigens 53: 263-268)).

A "computer-based system" refers to the hardware means, software means, and data storage means used to analyze the information of the present invention. The minimum hardware of the computer-based systems of the present invention comprises a central processing unit (CPU), input means, output means, and data storage means. A skilled artisan can readily appreciate that any one of the currently available computer-based system are suitable for use in the present invention. The data storage means may comprise any manufacture comprising a recording of the present information as described above, or a memory access means that can-access such a manufacture. A "computer readable media" refers to any suitable media on which the genetic map and its associated program for analysis and display of a genetic distribution map of the invention can be stored and, in most embodiments, executed for analysis.

To "record" data, programming or other information on a computer readable medium refers to a process for storing information, using any such methods as known in the art. Any convenient data storage structure may be chosen, based on the means used to access the stored information. A variety of data processor programs and formats can be used for storage, e.g. word processing text file, database format, etc.

A "processor" references any hardware and/or software combination which will perform the functions required of it. For example, any processor herein may be a programmable digital microprocessor such as available in the form of an electronic controller, mainframe, server or personal computer (desktop or portable). Where the processor is programmable, suitable programming can be communicated from a remote location to the processor, or previously saved in a computer program product (such as a portable or fixed computer readable storage medium, whether magnetic, optical or solid state device based). For example, a magnetic medium or optical disk may carry the programming, and can be read by a suitable reader communicating with each processor at its corresponding station.

Furthermore, not only causative genes for diseases but also those related to arbitrary phenotypes with genetic factor(s) can be mapped, for example, by randomly selecting individuals having the phenotype of interest and control individuals, and then comparing the frequency of MS genetic polymorphism markers among them.

Target Genes to be Mapped

Target genes that can be-mapped according to the present invention, include any gene of interest, including pathogenic genes and genes relating to human phenotypes with genetic factors, and are not limited to a specific range.

Diseases that have or may have genetic factors include monogenic diseases that are caused by the abnormality of a single gene, and polygenic diseases, the onset of which is triggered by the additive effect of multiple genetic factors and/or environmental factors. That is, with this invention, the term "pathogenic gene" refers not only to a single gene which can alone cause a disease, but also to a gene which is related to the onset or progress of a disease together with other genes, environmental factors, etc. Moreover, the term "pathogenic gene" herein includes genes that define the drug sensitivity of a patient to a treatment for a certain disease.

Examples of polygenic diseases include the so-called "common diseases", such as, for example, diabetes, hypertension, chronic articular rheumatism, gout, hyperlipemia, arteriosclerosis, schizophrenia, cancer, heart disease, cerebral infarction, and azoospermia, which include most of the lifestyle-related diseases. Moreover, autism, manic-depressive psychosis, epilepsy, or the like may also be included. Mapping according to the present invention allows causative gene(s) for a disease to be specified and the molecular mechanism thereof to be elucidated, and is expected to be applied to diagnosis, drug development, and development of preventive measures for the disease.

Moreover, genes relating to human phenotypes with genetic factors include causative genes relating to height, weight, skin condition, skin color, hair color, intelligence, memory, personality, and such, and the present invention may be used to map the genes. Therefore, genes expressing detectable phenotypes can be used as target genes of this invention. Furthermore, the gene mapping method of this invention can be applied not only to humans, but also to all kinds of animals including mammals, birds, breeding stock of domesticated and non-domesticated animals, and the like.

The invention has been applied to the mapping of genetic markers in human subjects having psoriasis vulgaris or having chronic articular rheumatism (RA). These populations and conditions are described in more detail below.

Psoriasis Vulgaris

Psoriasis vulgaris (MIM 177900) is a common skin disorder characterized by inflammatory cell infiltration and hyperproliferation of epidermal cells. The familial nature of this disease, which affects almost 2% of Caucasian populations, has long been recognized. However, in the Japanese population, a lower incidence (0.1%) has been observed, with most psoriasis vulgaris cases being sporadic. These facts clearly suggest that psoriasis vulgaris is a multi-factorial disease triggered by the involvement of some environmental factors in individuals with a particular genetic background. In fact, through recent linkage studies on the entire genome, several susceptibility gene loci on chromosomes 6p21.3 [human leukocyte antigen (HLA)], 17q25, 4q, and many others have been identified (Tomfohrde J. et al. (1994) Science, 20, 1141-1145; Matthews, D. et al. (1996) Nature Genet., 14, 231-233; Nair, R. P. et al. (1997) Hum. Mol. Genet., 6, 1349-1356; Trembath, R. C. et al. (1997) Hum. Mol Genet., 6,813-820).

Among them, the HLA locus is believed to be one of the major genetic factors predisposing a subject to the disease. It is well known that psoriasis vulgaris is associated with several serologically defined HLA class I antigens, such as HLA-B13, -B17, -B39, -B57, -Cw6, and -Cw7. This has been verified in many different populations throughout the world, including Caucasians and Japanese (Brenner W. et al. (1978) Arch. Dermatol. Res., 28, 337-339; Tiilikainen A. et al. (1980) Br. J. Dermatol., 102, 179-184; Ozawa A. et. al. (1981) J. Am. Acad. Dermatol., 4,205-230; Cao K. et al. (1993) Chin. Med. J., 106, 132-135; Schmitt-Egenolf, M. et al. (1996) J. Invest. Dermatol., 106, 711-714).

Among these alleles, the most consistent and significant correlation is observed with HLA-Cw6. However, this correlation is not as strong as that between HLA-B27 and ankylosing spondylitis (MIM 106300) (in this case, since up to 100% of the patients carry the allele, the HLA-B-27 is likely the bona fide cause) (Moller E. and Olhagen B. (1975) Tissue Antigens, 6,237-246). In actuality, only 10% (Japanese) to 45% (Caucasians) of patients with psoriasis vulgaris carry the HLA-Cw6 allele (Tiilikainen A. et al. (1980) Br. J. Dermatol., 102, 179-184; Asahina A. et al. (1991) J. Invest. Dermatol., 97, 254-258). Therefore, there is a possibility that the HLA-C gene itself is not the primary locus responsible for psoriasis vulgaris and that other gene(s) located nearby harbor the true pathogenic mutation/allele with strong linkage disequilibrium to HLA-Cw6. In this respect, fine mapping of this putative susceptibility gene locus, using high resolution genetic markers around the HLA-C gene, is needed.

The present inventors have completed sequence analysis of the entire 1.8 Mb HLA class I region, from MICB (major histocompatibility complex class I chain-related gene B) to HLA-F, and have identified more than 40 new genes within this segment (Mizuki N. et al. (1997) Genomics, 42, 55-66; Shina T. et al. (1998) Genomics, 47, 372-382; Shina T. et al. (1999) Immunol. Rev., 167, 193-199). Then, for high resolution mapping of a gene presumed to be the "psoriasis gene" linked with major histocompatibility complex (MHC) in Japanese psoriasis vulgaris patients, the present inventors narrowed the target to this gene fragment, selected a total of 11 highly polymorphic novel MS genetic polymorphism markers existing at regular intervals throughout the entire 1060 kb segment around the HLA-C gene locus, and performed correlation analysis thereof. Thus, MS genetic polymorphism markers are estimated to be distributed at a density of one every 96.7 kb.

Statistical analyses of the distribution and deviation from the Hardy-Weinberg equilibrium of the allelic frequency at each microsatellite locus were carried out using these MS genetic polymorphism markers. The results revealed that the pathogenic gene for psoriasis vulgaris is located within a reduced segment of 111 kb spanning 89 kb-200 kb of the telomeric HLA-C gene.

According to RT-PCR analysis using keratinocyte mRNA, this critical region for psoriasis Vulgaris included, in addition to three known genes, i.e., POU5FI (OTF3: octamer transcription factor 3) (Takeda J. et al. (1991) Nucleic Acids Res., 20, 4613-4620; Krishnan B. R. et al. (1995) Genomics, 30, 53-58), TCF19 (SC1: cell growth regulated gene) (Krishnan B. R. et al. (1995) Genomics, 30, 58-58; Ku, D. H. et al. (1991) Cell Growth Differ., 2, 179-186), and S (corneodesmosin gene) (Zhou Y. and Chaplin D. D. (1993) Proc. Natl. Acad. Sci. USA, 90, 9470-9474; Ishihara M. et al. (1996) Tissue Antigens, 48: 182-186; Tazi Ahnini, R. et al. (1999) Hum. Mol. Genet., 8,1135-1140; Allen M. H. et al. (1999) Lancet, 353, 1599-1590), four novel expressed genes identified by the genome sequencing of the entire HLC class I region, i.e., HCR (helix coiled-coil rod homologue), SPR1 (skin specific proline rich gene 1), SEEK1 (specific expressed gene in epidermal keratinocytes 1), and STG (skin specific-telomeric gene) (AB029331, AB031480, AB031479, and ABO31481, respectively). Accordingly, seven genes involved in susceptibility to psoriasis vulgaris were specified.

Among them, the S gene encodes a 52 kDa-56 kDa protein, corneodesmosin, which is expressed in differentiating epidermal keratinocytes, and thus a candidate gene related to psoriasis vulgaris. One, of the four novel genes in the 11 kb critical region related to psoriasis vulgaris was expressed in most of the examined tissues, including keratinocytes, and encodes a plectin-like protein with alpha-helical coiled-coil rod domains. Plectin has been proposed to provide mechanical strength to cells and tissues by acting as a cross-linking element of the cytoskeleton (Liu C. G. et al. (1996) Proc. Natl. Acad. Sci. USA, 30, 4278-4283). Furthermore, it is of particular interest that the plectin gene is responsible for the development of epidermolysis bullosa simplex (Pulkkinen L. et al. (1996) Hum. Mol. Genet., 5, 1539-1546). The other three novel genes show no homology to any known sequences in DNA databases. However, it is noteworthy that all of the three were specifically expressed in keratinocytes and skin tissues. Thus, in addition to the S gene, these four novel genes, from their expression pattern and/or predicted function, are genes related to psoriasis vulgaris. As described above, the inventors have exemplified that usage of a group of DNA sequences including MS genetic polymorphism markers according to the present invention allows highly efficient gene mapping In carrying out the methods of gene mapping of the invention, the inventors identified genetic regions associated with psoriasis vulgaris in humans, which regions are described in more detail in the Examples below. The inventors identified a region of about 111 kb extending from C1_2_6 (89 kb telomeric HLA-C) to C2_4_4 (200 kb telomeric HLA-C) as a common area critical for psoriasis vulgaris at a confidence level of more than 95%.

Thus the invention features methods for determining the susceptibility of a patient to psoriasis vulgaris, as well as method of determining-whether a subject may be a carrier for this condition. The diagnostic or prognostic method can be carried out using methods well known in the art, which methods involve analysis of the relevant genomic region in a nucleic acid sample obtained from a subject.

In general, the method involves, analyzing a region of about 111 kb extending from C1_2_6 to C2_4_4 for the presence-one or makers associated with psoriasis vulgaris. Preferably, the marker is at least one of allele 303, allele 357, allele 255, allele 259, or allele 223 (see Examples 2-3 below). Detection of one or more of these markers indicates the subject carries an allele associated with psoriasis vulgaris. Where the subject is homozygous for the market, the subject has or is susceptible to onset of psoriasis vulgaris. If the subject is heterozygous, the subject can be a carrier for the disease.

Rheumatoid Arthritis (RA)

Rrheumatoid arthritis (RA) is a progressive chronic inflammatory disease accompanied by proliferation of arthrosynovial cells and destruction of joints, cartilage, and bones, and a systemic autoimmune disease, which is as typical as systemic lupus erythematosus. The ratio of the RA patients in the entire population is approximately 0.5 to 1.0% worldwide, and in Japan approximately 0.7 million to 1.0 million patients are estimated. There are people with a distinctly high disease rate such as Native Americans and people with an exceptionally low disease rate such as Nigerians; however, considering the difference in diagnostic criteria or the like, it is thought that the difference in disease rates of differing races is generally small.

The RA rate increases over age, but decreases after the age of sixty. In particular, the women's disease rate is two to three times the men's disease rate, and people of ages between thirty and fifty tend to catch a disease. RA onset, however, does not catenate due to sexuality. Such difference due to sexuality is considered to emanate from some resistive reaction against the RA onset occurring in men; it is pointed out that as one cause, male hormones (androgen) may be of influence. According to this, it is considered that the threshold for the accumulated risk factor that causes RA onset on women is lower than that for men.

While an understanding level for immunological aspects such as cytokine cascade has been drastically enhanced due to the progress in molecular biologic techniques for RA, the complete picture of fundamental causes of the disease has not been directly identified even though some circumstantial evidence has been identified. However, it has been insinuated based on epidemiological data collected so far that RA has a hereditary nature. The hereditary nature includes familial accumulation and disease onset match rates for monozygotic twins.

In the case of diseases with hereditary nature, the disease incidence rate for a family within which that disease is inherited is expected to be higher than that for the entire group.

Since the familial disease incidence rate is approximately 8%, and the general-group disease incidence rate is approximately 1%, an index representing a familial accumulation level: $\lambda R$ (=familial disease incidence rate/general-group disease incidence rate) is then estimated as approximately 8. In other words, this means that the familial disease incidence rate is eight times that for the general group, insinuating that genetic factors are involved in the onset of the RA. In the case of the disease of interest not having a hereditary nature, incidence match rates (an incidence rate at which both twins suffer from the same disease) for a pair of monozygotic twins and a pair of dizygotic twins are almost the same and low; however, the stronger the hereditary nature, the higher the match rate for both types of twins, and in particular, the higher the match rate for monozygotic twins.

Aho and Simlman at, el, have reported that the incidence match rate for monozygotic twins is approximately four times that for dizygotic twins, which insinuates involvement of genetic factors. On the other hand, since the incidence match rate for the dizygotic twins is very low, it is expected that causative genetic factors or a plurality of RA susceptibility genes exist in the chromosome.

In the first step of identifying the susceptibility gene for the rheumatoid arthritis in which genetic factors are suggested to be involved, genetic correlation analysis is carried out using a method according to the present invention so as to restrict candidate causative gene regions.

Identification of MS genetic polymorphisms, according to the present invention, may be carried out by: amplifying the DNA sequence samples through polymerase chain reaction (PCR) using a forward primer and a reverse primer corresponding to each DNA sequence in a group of DNA sequences including microsatellite genetic polymorphism markers located in desired intervals; performing electrophoresis using a high resolution gel such as a DNA sequencer; and performing measurement and analysis of the DNA sequence fragment including microsatellite genetic polymorphism markers, which are amplified products.

According to the present invention, before identification, a distribution map for DNA sequences including microsatellite genetic polymorphism markers, which are used to indicate the nucleotide sequence and location in each DNA sequence of a group of DNA sequences including microsatellite genetic polymorphism markers that are located in advance on the human genome at desired intervals, is made and utilized. In actuality, the inventors prepared a group of DNA sequences including microsatellite genetic polymorphism markers on the human genome, and made and utilized a distribution map including the group of DNA sequences made up of all or a part of the nucleotide sequence referenced with sequence numbers 1 to 27088. Usage of this distribution map has enabled gene mapping throughout a genome according to the present invention. It is noted that Golden Path (Dec. 22, 2001) is used as the human genome reference sequence, which is utilized for making the distribution map.

A method according to the present invention can be easily implemented by utilizing DNA chips and mass spectrometry. Specifically, for example, by loading 1000 or more MS genetic polymorphism marker DNA sequences onto a chip, ionizing by laser irradiation, and then measuring the molecular weight using the traveled distance in a vacuum tube as an index, the number of repeats of the microsatellite, i.e., polymorphism, can be measured easily and quickly (Braun A. et al. (1997) Genomics 46: 46-23). More specifically, for example, DNA MassArray™ (MS chip) (Sequenom Co. LTD, San Diego, Calif., USA; PE Biosystems Co. LTD, Foster City, Calif., USA) may be used.

Moreover, through a method according to the present invention, using a forward primer and a reverse primer corresponding to the MS genetic polymorphism markers located throughout the genome, a first screening may be performed, and a second screening for the MS genetic polymorphism markers indicated positive by the first screening may then be performed. The second screening uses a different sample group, performing an analysis as with the first screening. The additional test through the second screening results in a drastic reduction of the number of the MS genetic polymorphism markers indicated false-positive without carrying out forced correction.

When the position of a target gene is restricted by mapping using the MS genetic polymorphism markers according to the present invention, candidate positions can be further restricted so as to specify the gene locus by a different mapping. For this purpose, for example, analysis using SNPs is effective. Since SNPs exist at a rate of one in 300 to 500 base pairs on the genome, with a high frequency of occurrence approaching several hundred times of that of MS genetic polymorphism markers, the SNP analysis after the mapping according to the present invention allows identification of the target gene. Specifically, after the analysis using MS genetic polymorphism markers, the polymorphism frequencies of SNPs in the candidate segments that have been considered to encompass the target gene are compared, for example, through correlation analysis between a group of patients and a group of healthy people, and such; and then, SNP markers with linkage disequilibrium detected by haplotype analysis are detected through linkage disequilibrium analysis.

To facilitate understanding of advantages of the mapping method using the MS genetic polymorphism markers according to the present invention, SNP (single nucleotide polymorphism) analysis of the human genome is explained below. The SNP analysis is a method for mapping causative genes of diseases using, as genetic polymorphism markers, 300,000 polymorphisms, which are collected based on differences due to replacements, deletions, or insertions of a single nucleotide in genes throughout the genome.

SNPs can be the cause of diseases with multiple factors, such diseases as the so-called lifestyle-related diseases. However, since the number of alleles of an SNP is generally only two, mapping capability is low (Kruglyak L. (1999) Nature Genetics 17: 21-24). In actuality, through analysis by the present inventors, microsatellites with 5 or more alleles that are located within approximately 200 kb from a target gene show a significant correlation, whereas the SNP analysis makes clear that only a part of SNPs that are located extremely close, within 5 kb, to the target gene showed significant correlation.

As mentioned above, this may be due to the fact that the capability in mapping SNPs is low, i.e., the number of alleles of an SNP being generally only two and its heterozygosity being 50% or less (normally 17%). Thus, according to the method of the present invention, the most effective strategy for genome mapping may be to identify a target gene by first performing mapping-using a distribution map with approximately 30,000 (density of one in approximately 100 kb) MS genetic polymorphism markers located throughout the genome so as to restrict the target gene candidate segment to 100 kb, and then performing SNP analysis.

In addition, to identify a target gene from a determined sequence, for example, an exon region that may possibly be expressed can be predicted using a computer program such as GRAIL (Uberbacher E. G. and Mural R. J. (1991) Proc. Natl. Acad. Sci. USA 88: 11261-5) and GENSCAN (Burge C. and Karlin S. (1997) J. Mol. Biol. 268: 78-94), or by performing a homology search of an expressed sequence tag (EST) database for a nucleotide sequence, in which repeating sequences are removed.

Based on these results, PCR primers and probes are prepared, and intracellularly expressed fragments are then identified by RT-PCR and Northern hybridization. Furthermore, once an expressed fragment is obtained, full-length cDNA can be obtained by 5' RACE, 3' RACE, and such. Alternatively, cDNA can be isolated through screening of cDNA libraries or CapSite libraries using a fragment of the gene as a probe, and such.

Through large scale sequence analysis of the human leukocyte antigen (HLA) gene locus, along with many genes, the present inventors have identified thus far microsatellites that can be used for mapping (Mizuki N. et al. (1997) Genomics, 42, 55-66; Shiina T. et al. (1998) Genomics, 47, 372-382; Shiina, T. et al. (1999) Immunol. Rev., 167, 193-199). Using the distribution map according to the present invention, the first screening in which gene mapping is performed throughout the genome can then provide the same results. Moreover, the gene mapping methods according to this invention can be applied by restricting this HLA region.

With this invention, the term "HLA region" refers to a 3.6 Mb segment from the centromeric HSET gene to the telomeric HLA-F gene. In addition to the causative gene(s) related to psoriasis described above, those relating to other diseases are expected to be present in the HLA region.

By implementing the gene mapping method according to this invention on the HLA region, it is possible to effectively map the causative genes for such diseases. Specifically, in addition to psoriasis and rheumatoid arthritis, examples of specific diseases for which causative genes are expected to be present in the HLA region include rheumatism, Behcet's disease, juvenile diabetes, Basedow disease, cardiomyopathy, diffuse panbronchiolitis, Buerger disease, Takayasu's disease, narcolepsy, sarcoidosis, Harada's disease, myasthenia gravis, multiple sclerosis, etc.

A causative gene for a disease specified using a mapping method according to this invention can be used for testing, preventing, and treating the disease. Genes relating to phenotypes other than diseases may also be used for tests such as genetic diagnosis and for gene therapy. Cloning identified genes can be performed by methods well known to those skilled in the art. For example, a cDNA library is made from cells in which such gene is expressed, and then prepared by performing hybridization using, as a probe, a gene fragment that is identified by mapping. The cDNA library may be prepared using, for example, the method described in the literature (Sambrook J. et al. (1989) Molecular Cloning, Cold Spring Harbor Laboratory Press), or commercially available cDNA libraries may be used instead. Alternatively, this preparation is made by: preparing RNA from cells in which the gene is expressed, synthesizing cDNA by a reverse transcriptase, synthesizing oligo-DNA based on the nucleotide sequence of the gene (or a fragment thereof), and amplifying the cDNA through PCR using the oligo-DNA as primers.

The nucleotide sequence of a full-length target gene is determined to find a translation region encoded thereby, and the amino acid sequence of the protein encoded by the gene can be obtained. Furthermore, the cDNA obtained may also be used as a probe for screening a genomic library to isolate genomic DNA.

The term "gene" encompasses both cDNA and genomic DNA. Genomic DNA typically includes exons, introns, a promoter, and enhancers of a gene. This term also includes alleles and variants.

Cloning a target gene can be carried out with the following exemplary procedure. mRNA is isolated from a cell, tissue, or organ in which the gene is expressed. Known methods can be used to isolate mRNA; for instance, total RNA can be prepared by guanidine ultracentrifugation (Chirgwin J. M. et al. Biochemistry (1979) 18, 5294-5299) or the AGPC method (Chomczynski P. and Sacchi N., Anal. Biochem. (1987) 162: 156-159), and mRNA can be purified from total RNA using mRNA Purification Kit (Pharmacia) and such. Alternatively, mRNA may be directly prepared using QuickPrep mRNA Purification Kit (Pharmacia).

The obtained mRNA may be used to synthesize cDNA using reverse transcriptase. cDNA may be synthesized using a kit such as AMV Reverse Transcriptase First-strand cDNA Synthesis Kit (Seikagaku Kogyo). Alternatively, cDNA may be synthesized and amplified using partial sequences of a target gene as primers according to the 5'-RACE method (Frohman M. A. et al., Proc. Natl. Acad. Sci. U.S.A. (1988) 85, 8998-9002; Belyavsky A. et al., Nucleic Acids Res. (1989) 17, 2919-2932) that utilizes 5Ampli FINDER RACE Kit (Clontech) and polymerase chain reaction (PCR). A target DNA fragment is prepared from the PCR products and linked to a vector DNA. The nucleotide sequence of the target DNA can be verified by well-known methods, such as dideoxynucleotide chain termination.

The isolated DNA, as described above, is inserted into a suitable vector. When *E. coli* is used as the host cell, the vector is not particularly limited as long as the vector has an "ori", which is for amplifying and mass-producing the vector in *E. coli* (e.g., JM109, DH5α, HB101, or XL1Blue), and such, and a marker gene for selecting the transformed *E. coli* (e.g., a drug-resistant gene selected by a drug (e.g., ampicillin, tetracycline, kanamycin, or chloramphenicol)). For example, M13-series vectors, pUC-series vectors, pBR322, pBluescript, pCR-Script and such can be used as the vector.

Apart from the vectors, pGEM-T, pDIRECT, pT7 and such can be also used for subcloning and excision of a cDNA as well. When a vector is used to produce a protein encoded by a gene, an expression vector is especially useful. For the purpose of expressing in *E. coli*, the expression vector should have the above characteristics such as being amplified in *E. coli*. Additionally, when *E. coli*, such as JM109, DH5α, HB 101, or XL1-Blue, is used as the host cell, the vector should have a promoter, for example, a lacZ promoter (Ward E. S. et al. (1989) Nature 341: 544-546; Ward E. S. (1992) FASEB J.6, 2422-2427), araB promoter (Better Metal (1988) Science 240, 1041-1043), or T7 promoter, that can efficiently promote the expression of a desired gene in *E. coli*. Other examples of the vectors include pGEX-5X-1 (Pharmacia), "QIAexpress system" (QIAGEN), pEGFP, and pET (for this vector, BL21, a strain expressing T7 RNA polymerase, is preferably used as the host).

Furthermore, the vector may also include a signal sequence directing the secretion of the polypeptide. For producing a protein into the periplasm of *E. coli*, the pelB signal sequence (Lei S. P. et al., J. Bacteriol. (1987) 169, 4379) may be used as the signal sequence for protein secretion. The calcium chloride method or electroporation may be used to introduce the vector into host cells. As vectors used to produce, for example, proteins, expression vectors derived from mammals (e.g., pcDNA3 (Invitrogen), pEF-BOS (Nucleic Acids Res. (1990) 18(17), p5322), pEF, pCDM8); insect cells (e.g., "BAC-TO-BAC Baculovirus Expression Systems" (GIBCO-BRL), pBacPAK8); plants (e.g., pMH1, pMH2); animal viruses (e.g., pHSV, pMV, pAdexLcw); retroviruses (e.g., pZIPneo); yeasts (e.g., "Pichia Expression Kit" (Invitrogen), pNV11, SP-Q1); and *Bacillus subtilis* (e.g., pPL608, pKTH50) may be employed besides *E. coli*.

In order to express in animal cells, such as CHO, COS, and NIH3T3 cells, the vector must have a promoter necessary for expression in such cells, e.g., SV40 promoter (Mulligan R. C. et al. (1979) Nature 277: 108-114), HMLV-LTR promoter, EF1α promoter (Mizushima S. and Nagata S. et al. (1990) Nucleic Acids Res. 18: 5322), CMV promoter, and the like. It is preferable that the vector additionally has a marker gene for selecting transformants (for example, a drug-resistant gene selected by a drug like neomycin, G418, or the like). Examples of vectors with such characteristics include pMAM, pDR2, pBK-RSV, pBK-CMV, pOPRSV, pOP13, and the like.

Furthermore, in order for a host vector system that aims to amplify the copy number in the cells, to obtain a cell strain capable of stable production, a method can be given amplifying the vector with methotrexate (MTX) by incorporating into CHO cells deficient in nucleic acid synthetic pathways, a vector (such as pCHOI) having a DHFR gene that compensates for the deficiency. Alternatively, in order to transiently express a gene, there is a method for transforming COS cells that have the gene for SV40 T antigen on the chromosome with a vector (such as pcD) having the SV40 replication origin. The replication origin may be one derived from a polyomavirus, adenovirus, bovine papilloma virus (BPV), or the like. Also, to amplify the gene copy number in the host cells, selection markers, such as the aminoglycoside transferase (APH) gene, thymidine kinase (TK) gene, *E. coli* xanthine-guanine phosphoribosyl transferase (Ecogpt) gene, and the dihydrofolate reductase (dhfr) gene may be included in the expression vector.

Alternatively, a gene can be expressed in animals by, for example, inserting the gene into an appropriate vector and introducing this vector into a living cell via the retroviral method, the liposome method, the cationic liposome method, the adenovirus method, or the like. Thus, it is possible to perform gene therapy for phenotypes of diseases caused by mutation or polymorphism of the gene, and such. The vectors used in these methods include, but are not limited to, adenovirus-vectors (e.g., pAdexlcw), retrovirus vectors (e.g., pZIPneo), and or the like. General techniques for gene manipulation, such as insertion of a DNA fragment into a vector, can be performed according to conventional methods (Sambrook J. et al. (1989) Molecular Cloning 2nd ed., 5.61-

5.63, Cold Spring Harbor Lab. press). Administration to living cells may be performed according to the ex vivo method or the in vivo method.

The host cell into which the vector is introduced is not particularly limited. For example, *E. coli*, various animal cells and such can be used. The host cell can be used, for example, as a production system to produce and express a protein. Protein production systems include in vitro and in vivo systems. Such production systems using eukaryotic cells or prokaryotic cells can be given as in vitro production systems.

Animal cells, plant cells, and fungi cells can be used as the host cell when using eukaryotic cells. Mammalian cells, for example, CHO, COS, 3T3, myeloma, BHK (baby hamster kidney), HeLa, Vero, amphibian cells e.g., *Xenopus oocytes* (Valle et al., Nature (1981) 291, 358-340), and insect cells (e.g. Sf9, Sf21, Tn5) are known as animal cells. Among CHO cells, dhfr-CHO (Urlaubb G. and Chasin L. A. (1980) Proc. Natl. Acad. Sci. USA 77: 4216-4220), which are CHO cells deficient in the DHFR gene, and CHO K-1 (Kao F. T. and Puck T. T. (1968) Proc. Natl. Acad. Sci. USA 60: 1275-1281), are particularly preferable. Among animal cells, CHO cells are particularly preferable for large scale expression.

A vector can be introduced into a host cell by, for example, the calcium phosphate method, the DEAE-dextran method, methods using cationic liposome DOTAP (Boehringer-Mannheim), electroporation, lipofection, or the like.

Plant cells originating from *Nicotiana tabacum* are known as protein producing systems and may be used as callus cultures. As fungal cells, yeast cells such as Saccharomyces, including *Saccharomyces cerevisiae*, or filamentous fungi such as Aspergillus, including *Aspergillus niger*, are known.

When utilizing prokaryotic cells, there is a production system using bacterial cells. Bacterial cells, for example, *E. coli* such as JM109, DH5α, HB101, as well as *Bacillus subtilis* are known.

The transformant cells produced using a recombinant DNAs are cultured in vitro to obtain a protein. Culturing can be performed according to known methods. DMEM, MEM, RPMI1640, or IMDM, or the like, may be used as a culture medium for animal cells with or without serum supplements such as fetal calf serum (FCS). It is preferable that the pH for incubation is approximately 6 to 8. Culturing is typically performed for about 15 to 200 hrs at about 30 to 40 degrees centigrade, and the culture medium may be replaced, aerated, or stirred if necessary.

Alternatively, in vivo protein production system includes, for example, a production system using animal or plant. A target DNA is introduced into an animal or a plant, so as to produce proteins in vivo therewithin, and then recovered. With this present invention, these animals and plants are included in the "host".

Animals to be used for the production system described above include mammals and insects. Goats, pigs, sheep, mice, and cattle can be used as mammals (Vicki Glaser, SPECTRUM Biotechnology Applications (1993)). Alternatively, the mammals may be transgenic animals. For instance, a desired DNA may be prepared as a fusion gene with a gene, such as goat β casein gene, that encodes a protein specifically produced into milk. DNA fragments including this fusion gene are injected into goat embryos, which are then introduced back to female goats. Desired proteins are recovered from milk produced by the transgenic goats (those born from the goats that had received the modified embryos) or from their offspring. To increase the amount of milk containing the proteins produced by transgenic goats, appropriate hormones may be administered (Ebert K. M. et al., Bio/Technology (1994) 12: 699-702).

Alternatively, insects, such as silkworm, may be used as the host. When using silkworms, baculoviruses, into which a DNA encoding a desired protein has been inserted, can be used to infect the silkworms, and the desired protein can be recovered from body fluids thereof (Susumu M. et al., Nature (1985) 315, 592-594).

As plant hosts, tobacco can be used, for example. When using tobacco, a DNA encoding a desired protein may be inserted into a plant expression vector, such as pMON 530, which is then introduced into bacteria, such as *Agrobacterium tumefaciens*. The bacteria are used to infect tobacco, such as *Nicotiana tabacum*, and the desired polypeptide is recovered from the leaves (Ma J. K. et al. (1994) Eur. J. Immunol. 24, 131-138).

A protein obtained as above can-be isolated from the interior or exterior of the host cell (culture medium and such), and purified to a substantially pure homogeneous protein. The method for protein isolation and purification is not limited to any specific method; in fact, any standard method may be used. For instance, column chromatography, filtration, ultrafiltration, salting out, solvent precipitation, solvent extraction, distillation, immunoprecipitation, SDS-polyacrylamide gel electrophoresis, isoelectric point electrophoresis, dialysis, and recrystallization may be appropriately selected and combined to isolate and purify the protein.

Chromatography, such as affinity chromatography, ion-exchange chromatography, hydrophobic chromatography, gel filtration chromatography, reverse phase chromatography, adsorption chromatography and such may be used (Strategies for Protein Purification and Characterization: A Laboratory Course Manual. Ed. Daniel R. Marshak et al., Cold Spring Harbor Laboratory Press (1996)). These chromatographies may be performed using liquid chromatographies, such as HPLC and FPLC. Highly purified proteins can be obtained by the above purification methods.

A protein may be optionally modified or partially deleted by treatment with an appropriate protein modifying enzyme before or after purification. For example, trypsin, chymotrypsin, lysylendopeptidase, protein kinase, glucosidase and such are used as protein-modifying enzymes.

Antibodies against a protein, which is encoded by a target gene, can be prepared by using proteins obtained as above. The antibodies may take any form, including monoclonal antibodies and polyclonal antibodies. Such form further includes antiserum obtained by immunizing animals such as rabbits with the protein, all classes of polyclonal and monoclonal antibodies, as well as human and humanized antibodies produced by genetic recombination.

A protein used as a sensitizing antigen to obtain antibodies may be derived from any animal species. However, it is preferably from a mammal, such as human, mouse, or rat, more preferably, from a human.

A full-length protein or a partial peptide thereof may be used as a sensitizing antigen with the present invention. A partial peptide may be, for example, an amino (N)-terminus or carboxy (C)-terminus fragment of the protein. Herein, an "antibody" is defined as an antibody that reacts with either the full-length or a fragment of the protein.

For preparing antibodies, a target gene or its fragment may be-inserted into a known expression vector used to transform a host cell as described herein. The desired protein or its fragment may be recovered from the exterior or interior of the host cell by any standard method, and may be used as the sensitizing antigen. Alternatively, cells expressing the protein or their lysates, or a chemically synthesized protein may be used as an antigen. Preferably, short peptides are used as antigens by appropriately binding to carrier proteins, such as keyhole limpet hemocyanin, bovine serum albumin, and ovalbumin.

Any mammal may be immunized with the sensitizing antigen. However, preferably, the compatibility with parental cells used for cell fusion is taken into account. In general, animals classified as Rodentia, Lagomorpha, or Primates are used.

Animals classified as Rodentia include, for example, mice, rats, and hamsters. Animals classified as Lagomorpha include, for example, rabbits. Animals classified as Primates include, for example, monkeys of Catarrhini (old world monkeys), such as *Macaca fascicularis*, rhesus monkeys, sacred baboons, or chimpanzees.

Methods for immunizing animals with sensitizing antigens are well known in the art. Intraperitoneal injection or subcutaneous injection of sensitizing antigens is used for mammals as a standard method. More specifically, the sensitizing antigen may be diluted and suspended with phosphate-buffered saline (PBS), physiological saline, etc. into an appropriate amount. If desired, the antigen suspension may be mixed with an appropriate amount of a standard adjuvant, such as Freund's complete adjuvant, made into an emulsion, and then administered to mammals. Preferably, this is followed by several administrations of the sensitizing antigen mixed with an appropriate amount of Freund's incomplete adjuvant every 4 to 21 days. An appropriate carrier may also be used when immunizing the sensitizing antigen. After the above immunization, the serum is examined for an increase in the amount of desired antibodies by a standard method.

Polyclonal antibodies may be prepared by collecting blood from the immunized mammal after confirming the increase in the levels of desired antibodies in the serum. The serum is separated from the blood by any conventional method. Serum containing a polyclonal antibody may be used as a polyclonal antibody, or if necessary, the fraction containing the polyclonal antibody may be isolated from the serum, and the isolated fraction can then be purified using a protein A or G column, thereby preparing immunoglobulin G or M.

To prepare monoclonal antibodies, immune cells are collected from a mammal immunized with an antigen and checked for an increase in the level of the desired antibodies in the serum as described above, and these cells are subjected to cell fusion. The immune cells used for cell fusion are preferably obtained from the spleen. The other parent cell fused with the above immune cell is preferably a mammalian myeloma cell, and more preferably, a myeloma cell that has acquired a special feature that can be used for selecting fusion cells by a drug.

The above immune cell and myeloma cell may be fused by basically any standard method, such as those described by Milstein et al. (Galfre G. and Milstein C., Methods Enzymol. (1981) 73, 3-46).

Resulting hybridomas obtained by cell fusion may be selected by cultivating in a standard selection medium, such as the HAT medium (medium containing hypoxanthine, aminopterin, and thymidine). The cell culture is typically continued in the HAT medium for a time period that is sufficient to allow all cells, except the desired hybridoma (non-fused cells), to die, usually from several days to several weeks. Then, standard limiting dilution is performed to screen and clone a hybridoma cell producing the desired antibody.

In addition to the above method for immunizing a nonhuman animal with an antigen for preparing a hybridoma, human lymphocytes, such as those infected by the EB virus, may be immunized with a protein, protein-expressing cells, or their lysates in vitro. The immunized lymphocytes are then fused with human-derived myeloma cells having indefinite division ability, such as U266, to yield a hybridoma producing a desired human antibody binding to a protein (Japanese Patent Application Laid-open No. Sho 63-17688).

Subsequently, the hybridomas thus obtained are transplanted into the abdominal cavity of a mouse from which the ascites is collected. The monoclonal antibodies thus obtained can be purified by, for example, ammonium sulfate precipitation or column chromatography using a protein A or protein G column, a DEAE ion exchange column, an affinity column to which a protein encoded by a target gene is coupled, and such. The prepared antibody can be used not only for purifying and detecting the protein encoded by the target gene, but also as a candidate for an agonist or antagonist of the protein. Such an antibody may also be considered to be used for antibody-therapy of diseases. To administer the obtained antibody to humans (namely, antibody therapy), human antibodies or humanized antibodies are preferred to reduce immunogenicity.

For example, transgenic animals having a repertory of human antibody genes may be immunized with a protein, protein-expressing cells, or their lysates as antigen. Antibody producing cells are collected from the animals, and fused with myeloma cells to obtain hybridoma, from which human antibodies against the protein can be prepared (see WO92-03918, WO93-2227, WO94-02602, WO94-25585, WO96-33735, and WO96-34096). Alternative to producing antibodies using hybridoma, an immune cell that produces antibodies, such as an immunized lymphocyte, which are immortalized by an oncogene, may be used for preparing antibodies.

The monoclonal antibodies obtained as such can also be recombinantly prepared using genetic engineering techniques (see, for example, Borrebaeck C. A. K. and Larrick J. W., Therapeutic Monoclonal Antibodies, published in the United Kingdom by MacMillan Publishers LTD, (1990)).

A recombinant antibody can be prepared by cloning a DNA encoding the antibody from an immune cell, such as a hybridoma or an immunized lymphocyte producing the antibody; inserting this into an appropriate vector; and introducing the vector into a host cell. The present invention encompasses this recombinant antibody.

According to the present invention, an antibody may be a fragment of an antibody or modified antibody, so long as it binds to a protein encoded by a target gene. For instance, the antibody fragment may be Fab, F(ab)$_2$, Fv, or single chain Fv (scFv) in which Fv fragments from H and L chains are linked by an appropriate linker (Huston J. S., et al.(1988) Proc. Natl. Acad. Sci. U.S.A. 85: 5879-5883). More specifically, treating an antibody with an enzyme, such as papain or pepsin, may generate an antibody fragment. Alternatively, a gene encoding the antibody fragment may be constructed, inserted into an expression vector, and expressed in an appropriate host cell (see, for example, Co M. S. et al., J. Immunol., (1994) 152: 2968-2976; Better M. and Horwitz A. H., Methods Enzymol., (1989) 178: 476-496; Pluckthum A. and Skerra A., Methods Enzymol., (1989) 178,497-515; Lamoyi E., Methods Enzymol., (1986) 121,652-663; Rousseaux J. et al., Methods Enzymol., (1986) 121, 663-669; Bird R. E. and Walker B. W., Trends Biotechnol. (1991) 9, 132-137).

An antibody may be modified by conjugation with a variety of molecules, including polyethylene glycol (PEG). "Antibodies" of the present invention include such modified antibodies. Such modified antibody can be obtained by chemically modifying an antibody. These modification methods are conventional in the field.

Alternatively, according to the present invention, an antibody may be obtained as a chimeric antibody, comprising a variable region derived from a nonhuman antibody, and the constant region derived from a human antibody, or as a humanized antibody, including the complementarity determining region (CDR) derived from a nonhuman antibody, the framework region (FR) derived from a human antibody, and the constant region, by well-known methods.

Antibodies thus-obtained may be purified to homogeneity. Any standard protein separation and purification method may be used for antibody separation and purification according to the present invention. For example, column chromatographies, such as affinity chromatography; filtration; ultrafiltration; salting out; dialysis; SDS polyacrylamide gel electrophoresis; isoelectric point electrophoresis may be appropriately selected and combined to isolate and purify the antibody (Antibodies: A Laboratory Manual. Ed Harlow and David Lane, Cold Spring Harbor Laboratory (1988)). However, the methods are not limited thereto. The concentration of the obtained antibody may be determined by measuring absorbance, by enzyme-linked immunosorbent assay (ELISA), or the like.

Columns used for affinity chromatography include protein A columns and protein G columns. For example, Hyper D, POROS, and Sepharose F. F. (Pharmacia) may be given as columns using protein A columns. Chromatography other than affinity chromatography includes ion-exchange chromatography, hydrophobic chromatography, gel filtration chromatography, reverse phase chromatography, adsorption chromatography, and such (Strategies for Protein Purification and Characterization: A Laboratory Course Manual. Ed. Daniel R. Marshak et al., Cold Spring Harbor Laboratory Press (1996)). These chromatographies can be conducted using liquid chromatographies, such as HPLC and FPLC.

For example, measurements of absorbance, enzyme-linked immunosorbent assay (ELISA), enzyme immunoassay (EIA), radioimmunoassay (RIA), or immunofluorescence may be used to measure the antigen binding activity of an antibody. In the case of using ELISA, a target protein is applied to a solid state antibody plate, and then a sample containing a desired antibody, such as culture supernatant of antibody producing cells or a purified antibody, is applied. Then, a secondary antibody, which recognizes the primary antibody labeled with an enzyme, such as alkaline phosphatase, is applied. The plate is then incubated. After washing, an enzyme substrate, like p-nitrophenyl phosphate, is added to the plate and absorbance is measured to evaluate the antigen binding activity of the sample. A fragment of a protein, such as a C-terminus fragment or a N-terminus fragment, may be used as the protein. BIAcore (Pharmacia) may be used to evaluate the activity of an antibody.

The above methods allow the detection or measurement of a protein encoded by a target gene, by exposing an antibody to a sample assumed to contain the protein encoded by the target gene in the sample, and detecting or measuring the immune complex formed by the antibody and the protein. Because the measurement method can specifically detect or measure a protein encoded by a gene, the method may be useful in a variety of experiments, tests, diagnoses, and such, in which the protein is used.

The present invention also provides polynucleotides comprising at least 15 nucleotides that are complementary to one strand of a double strand of a target gene or to the complementary strand thereof.

The term "complementary strand" as used herein refers to one strand of a double strand DNA comprising A:T (or A:U for RNA) and G:C base pairs when viewed against the other strand. Furthermore, "complementary" encompasses not only a nucleotide sequence completely complementary to a continuous nucleotide region with at least 15 nucleotides but also a homology of at least 70%, preferably at least 80%, more preferably 90%, and most preferably 95% or more at the nucleotide sequence level. Homology of proteins can be determined using the algorithm described in the literature (Wilbur W. J. and Lipman D. J., Proc. Natl. Acad. Sci. USA, (1983) 80: 726-730).

Such nucleic acids include probes and primers used for the detection and amplification of a target gene; probes and primers for detecting the expression of the gene; and nucleotides and nucleotide derivatives (for example, antisense oligonucleotides, ribozymes, or DNAs encoding them) used for suppressing the expression of the gene. Herein, the detection of a gene also includes the detection of gene mutation. Furthermore, such nucleic acids can be used in the preparation of DNA chips.

If the above polynucleotide is used as a primer, the 3'-region thereof may be the complementary site, and restriction enzyme recognition sites, tag sequences, and such may be attached to the 5'-region. Antisense oligonucleotides include, for example, antisense oligonucleotides that hybridize with any portion of the protein coding region. The antisense oligonucleotide is preferably an antisense of a continuous sequence comprising at least 15 nucleotides or more within the protein coding region. More preferably, the above continuous sequence comprising at least 15 nucleotides or more contains a translation initiation codon.

A derivative or modified form of an antisense oligonucleotide may also be used. The latter form may be prepared by modifying an antisense oligonucleotide with lower alkylphosphonates, such as, methylphosphonate or ethylphosphonate, or with phosphorothioate, or phosphoroamidate.

The antisense oligonucleotide is not restricted to one in which all nucleotides are complementary to the corresponding nucleotides within a given region of a DNA or mRNA. So long as an oligonucleotide can specifically hybridize with a DNA or mRNA encoding a target gene, it may have one or more nucleotide mismatches.

A derivative of an antisense oligonucleotide according to the present invention may act on cells producing a protein encoded by a target gene and bind to a DNA or mRNA encoding the protein. It then may inhibit the expression of the protein by inhibiting its transcription or translation, or by promoting the degradation of mRNA, and thereby inhibiting the function of the protein.

A derivative of an antisense oligonucleotide of the present invention may be mixed with an appropriate base that is inactive against the derivative, and used as a medicine for external application, such as a liniment or poultice. If necessary, it may be mixed with excipients, isotonizing agents, solubilizing agents, stabilizers, preservatives, pain-killers, or such to be prepared as a tablet, powder, granule, capsule, liposome capsule, injectable solution, liquid formulation, nose drops, freeze-dried agent, or such. The above may be prepared according to standard methods.

For treating patients, a derivative of an antisense oligonucleotide according to the present invention may be directly applied to the affected area of a patient, or administered into blood vessels so as to finally reach the affected area. Moreover, the derivative may be encapsulated in antisense-encapsulating materials, such as liposomes, poly-L-lysine, lipid, cholesterol, lipofectin, or their derivatives in order to increase durability and/or membrane permeability.

The dose of a derivative of the antisense oligonucleotides according to the present invention may be appropriately adjusted depending on the patient's conditions, and a preferable amount in the range of, for example, 0.1 to 100 mg/kg, preferably 0.1 to 50 mg/kg, may be administered.

Since the antisense oligonucleotides of the present invention inhibit the expression of a protein encoded by a target gene, they are useful as an inhibitor of the biological activity of the protein. An expression inhibitor containing an antisense oligonucleotide according to the present invention is useful due to its ability to inhibit the biological activity of the protein, and is further useful not only for medicinal application but as a functional analysis tool for the gene.

Test of mutation or expression of a target gene or a protein can be performed using an antibody against the protein encoded by the target gene, or a polynucleotide containing at least 15 nucleotides complementary to one of the chains of the gene or to the complementary strand thereof. When the target gene is related t® a disease, testing of the disease can be performed using the antibody or the polynucleotide. The test of a disease according to the present invention includes not only tests of patients expressing symptoms of the disease associated with the mutation of a pathogenic gene, but also tests of the expression level of the pathogenic gene and tests of the mutation of the gene performed to determine whether or not the subject is prone to have the disease due to abnormality in the expression level of the pathogenic gene or due to mutation of the gene. That is, the danger of having the disease is considered to be greatly increased due to abnormalities in the expression of the pathogenic gene and occurrence of mutation in one of the alleles of the pathogenic gene, even when no symptom has risen to the surface. Furthermore, phenotypes other than diseases that have genetic factors can be, for example, tested for the presence or absence of their causative genes, or for the mutation or expression of those genes.

Methods for testing diseases and such using antibodies includes, for example, a method including the step of detecting a protein encoded by a causative gene in a test sample. Specifically, the method for testing with antibodies against proteins encoded by causative genes includes the steps of: (a) making the above-mentioned antibody have contact with a test sample; and (b) detecting binding of the antibody to the test sample; Detection of proteins can be performed by immunoprecipitation using antibodies, Western blotting, immunohistochemisty, ELISA, and such.

For the testing according to the present invention, polynucleotides (probe and primers) complementary to a nucleotide sequence of a transcript or cDNA of a gene and a nucleotide sequence of a genomic DNA sequence (including endogenous transcription regulatory sequence) or to their complementary strands may be used. Incidentally, testing mutation includes a test that specifies "carriers", i.e., those having mutation in one of the alleles.

When used as a primer, polynucleotides are normally 15 to 100 bp, and preferably 17 to 30 bp. There are no limitations on the primer so long as it can amplify at least a portion of a target gene region or a region that regulates its expression. Examples of such regions include, for example, exons, introns, promoters, and enhancer regions of the gene.

On the other hand, as a probe, the polynucleotide normally has a strand length of at least 15 bp or longer if it is a synthetic polynucleotide. Double-stranded DNA obtained from a clone that has been inserted into a vector such as plasmid DNA may also be used as a probe. There are no limitations on the probe so long as it is complementary to the nucleotide sequence of at least a portion of a gene or the region regulating its expression, or to its complementary strand.

The regions to which the probe may hybridize includes, for example, the exon, intron, promoter, and enhancer regions of a gene. When used as probes, the polynucleotide or the double stranded DNA are labeled appropriately, and then used. The labeling methods are, for example, phosphorylating the 5'-terminus of polynucleotide with $^{32}$P using T4 polynucleotide kinase, or incorporating a substrate nucleotide labeled with biotin, fluorescent moiety, isotopes such as. $^{32}$P, and such, and using a random hexamer oligonucleotide as a primer and DNA polymerase such as Klenow enzyme (random priming method).

An example of a testing method that utilizes an antibody against a protein encoding a target gene or a polynucleotide containing at least 15 nucleotides complementary to one of the strands of the gene or to its complementary strand, includes a method that includes the step of detecting a transcript of the target gene within a test sample. Such a test method includes methods including the steps of: (a) making the above-mentioned polynucleotide have contact with a test sample, and (b) detecting binding of the polynucleotide to an mRNA in the test sample. Such tests can be performed, for example, by Northern hybridization or RT-PCR.

A test that uses RT-PCR specifically includes (a) synthesizing cDNA from an mRNA in a test sample, (b) performing a polymerase chain reaction using the synthesized cDNA as a template and the polynucleotide of the present invention as a primer, and (c) detecting the DNA amplified by the polymerase chain reaction. Northern hybridization and RT-PCR can be performed by well-known genetic engineering techniques. Also, detection using a DNA chip or a DNA microarray is possible.

In addition, test of diseases and such may be performed by detecting mutations or polymorphisms in target genes. Specifically, such tests can be performed by detecting mutations or polymorphisms in the transcription regulatory region or encoding region of a target gene.

According to an embodiment of such testing methods, the nucleotide sequence of a target gene from a subject is directly determined. For example, a portion or all of a target gene from a subject (for example, regions including exons, introns, promoter, and enhancer) may be amplified by PCR (Polymerase Chain Reaction) and such, using the above-mentioned nucleotide as a primer, DNA isolated from a subject as a template, and the nucleotide sequence thereof may be determined. Then, the determined sequence may be compared to the sequence of a gene derived from a control subject (e.g., healthy person, etc.) to accomplish the test.

As a method for testing according to the present invention, various methods are used in addition to the method for directly determining the nucleotide sequence of DNA derived from the subject. An embodiment of the test methods includes the steps of: (a) preparing a DNA sample from a subject, (b) amplifying the subject-derived DNA using the polynucleotide of this invention as a primer, (c) dissociating the amplified DNA into single-stranded DNA, (d) separating the dissociated single stranded DNA on a non-denaturing gel, and (e) comparing the mobility of the separated single-stranded DNA on the gel with that of a control subject.

An example of such methods is a single-strand conformation polymorphism (PCR SSCP) method (Cloning and polymerase chain reaction-single-strand conformation polymorphism analysis of anonymous Alu repeats on chromosome 11. (1992 Jan 1) Genomics 12(1): 139-146; Detection of p53 gene mutations in human brain tumors by single-strand conformation polymorphism analysis of polymerase chain reaction products. (1991 Aug 1) Oncogene 6(8): 1313-1318; Multiple fluorescence-based PCR-SSCP analysis with postlabeling. (1995 Apr. 1) PCR Methods Appl. 4(5): 275-282).

This method is relatively simple and has the advantage of requiring the smallest amount of sample. Therefore, it is especially preferable when screening many DNA samples. Its principles are as follows. When a double-stranded DNA fragment is dissociated into single strands, each strand forms an independent higher-order structure according to its nucleotide sequence. When this dissociated DNA strand is electrophoresed on a polyacrylamide gel that does not contain a denaturant, depending on the difference in each higher-order structure, complementary single-stranded DNA having the same length of nucleotides move to different positions. The higher-order structure of such single-stranded DNA changes even with replacement of a single nucleotide, and indicates different mobility in the polyacrylamide gel electrophoresis: Therefore, by detecting this change in mobility, existence of mutation in the DNA fragment, such as point mutation, deletion, or insertion, can be detected.

Specifically, to begin with, a whole target gene, or a portion of it, is amplified by PCR and such. Normally, the amplified range preferably has a length of approximately 200 to 400 bp. The amplified region includes all exons and all introns of the gene and also, promoter and enhancers of the gene. During gene fragment amplification by PCR, synthesized DNA fragments are labeled by performing PCR using a primer labeled with isotopes, such as $^{32}P$ or with fluorescent pigments, biotin, and such, or by adding a substrate nucleotide labeled with isotopes such as $^{32}P$, or with fluorescent pigments, biotin, and such into the PCR reactive solution. Otherwise, labeling can be performed by adding a substrate nucleotide labeled with isotopes, such as $^{32}P$, or with fluorescent pigments, biotin, and such to a synthesized DNA fragment using Klenow enzyme and such, after PCR.

The labeled DNA fragment obtained as such is denatured by heating and such, and electrophoresis is performed using a polyacrylamide gel that does not contain denaturants such as urea. Here the conditions for DNA fragment separation can be improved by adding an appropriate amount (approximately 5% to 10%) of glycerol to the polyacrylamide gel. Electrophoretic conditions change with properties of each DNA fragment, but normally, it is performed at room temperature (20° C. to 25° C.). When a favorable separation cannot be achieved, the temperature that gives the most appropriate mobility is tested to be between 4° C. to 30° C.

After electrophoresis, mobility of the DNA fragment is detected by autoradiography using an X-ray film, a scanner detecting fluorescence and such, and then analyzed. When a band having a difference in mobility is detected, this band is directly cut out from the gel and then re-amplified by PCR, and by direct sequencing, the existence of mutation can be confirmed. Also, even when labeled DNA is not used, by staining the gel after electrophoresis with ethidium bromide or by silver staining and such, bands can be detected.

Another embodiment of the testing method of this invention includes the steps of: (a) preparing a DNA sample from a subject, (b) amplifying the subject-derived DNA using a polynucleotide of this invention as a primer, (c) cleaving the amplified DNA, (d) separating the DNA fragments according to their size, (e) hybridizing the detectably labeled polynucleotide of this invention as a probe to the separated DNA fragment, and (f) comparing the size of the detected DNA fragment with that of a control subject.

Examples of such methods include methods using restriction fragment length polymorphism (RFLP), PCR-RFLP, and such. Normally, restriction enzymes are used as enzymes to cleave DNA. Specifically, when mutation or polymorphism exists at the restriction enzyme recognition site, or when there is a nucleotide insertion or deletion in the DNA fragment formed by restriction enzyme treatment, the size of the fragment formed after restriction enzyme treatment changes compared to that of a control (healthy subject). Amplifying this portion containing the mutation or polymorphism by PCR, and then treating with each restriction enzyme enables the detection of these mutations or polymorphisms as differences in band mobility after electrophoresis. Otherwise, chromosomal DNA is treated with these restriction enzymes, and after electrophoresis, by performing Southern blotting using the polynucleotide described above as: a probe, the presence or absence of mutation or polymorphism can be detected.

The restriction enzyme to be used can be appropriately selected depending on each region to be tested. In this method, in addition to genomic DNA, RNA prepared from a subject may be made into cDNA by reverse transcriptase, and after cleaving it in its original form by a restriction enzyme, Southern blotting can be performed. Also, using this cDNA as a template, a portion of or a whole target gene can be amplified by PCR, and after cleaving it with restriction enzyme, their difference in mobility can be investigated.

Furthermore, instead of using DNA prepared from a subject, a similar detection is possible using RNA as well. Such a method includes the steps of: (a) preparing an RNA sample from a subject, (b) separating the prepared RNA according to size, (c) hybridizing the polynucleotide of this invention, that has a detectable label as a probe, to the separated RNA, and (d) comparing the size of the detected RNA with that of a control. An example of a specific method includes electrophoresing RNA prepared from a subject, performing Northern blotting using the polynucleotide described above as a probe, and detecting differences of mobility.

An embodiment of the test methods includes the steps of: (a) preparing a DNA sample from a subject, (b) amplifying the subject-derived DNA using the polynucleotide of this invention as a primer, (c) dissociating the amplified DNA on a gel having a gradually-increased concentration of a DNA denaturant, and (d) comparing the mobility of the dissociated DNA on the gel with that of a control subject.

An example of such a method is denaturant gradient gel electrophoresis (DGGE). The whole target gene, or a portion thereof, is amplified by PCR using the primer as described above, and such. This is then electrophoresed on a polyacrylamide gel in which the concentration of a denaturant such as urea gradually becomes higher in the gel as the material moves, and this is compared to that of a control subject (such as a healthy subject). For a DNA fragment in which mutation exists, the DNA fragment becomes single stranded at a position of lower denaturant concentration, and the rate of movement becomes extremely slow. Therefore, by detecting this difference in mobility, the presence or absence of mutation of polymorphism can be detected.

Apart from these methods, for the purpose of detecting mutations only at a particular position, allele specific oligonucleotide (ASO) hybridization can be used. An oligonucleotide containing a sequence in which a mutation is thought to exist is prepared, and when this is hybridized with sample DNA, if mutation exists, the efficiency of hybrid formation decreases. This can be detected by Southern blotting or by a method that utilizes the property of quenching by intercalation of a specialized fluorescent reagent into a gap in the hybrid, or such a method.

Also, detection by a ribonuclease. A mismatch cleavage method is possible. Specifically, a whole target gene, or a portion thereof, is amplified by PCR and such, and the product is hybridized with labeled RNA prepared from a target gene fragment and such inserted in a plasmid vector, and such. In the portion in which mutation exists, the hybrid takes a single-stranded structure, therefore, this portion is cleaved by ribonuclease A, and by detecting this with autoradiography, and such, existence of mutation can be detected.

Computer-Related Embodiments

In another aspect, the invention provides a distribution map of one or more human genomic regions, which regions can include an entire chromosome, and in particular 2 or more, 5 or more, 10 or more chromosomes of the human genome. In one embodiment, the entire human genome is mapped with microsatellite markers, including 23 single chromosomes (i.e., 22 autosome and an X or Y sex chromosomes). The microsatellite genetic polymorphism markers are located on the human genome map in intervals of at least about 50 to 150 Kb, usually at least about 80 to 120 Kb, more usually at least about 90 to 110 Kb.

The map can include, for example, the position of the markers provided in the Sequence Listing as SEQ ID NOS: 1-27,088. The map can additionally including sequence information for SEQ ID NOS:1-27088, as well as information for design and production of primer pairs (forward and reverse) for use in amplifying the markers.

The distribution map can provide not only the location of the polymorphic markers, but can also be modified to include, either by the manufacturer or by the user performing the marker analysis, the frequency of the markers in a sample from a test subject compared to a control subject, where the test subject has a characteristic of interest (e.g., a condition, disease, and the like). The map can also provide information about the genomic regions throughout which the markers are positioned.

The map thus represents a collection of information, which can be provided in an electronic, machine-readable form (e.g., stored in a computer-readable form, as in a computer system and/or as part of a computer program). The distribution map and sequence information can be used in a variety of ways as exemplified herein, e.g., as a resource for gene discovery, as markers of a given disease or disease state, and the like.

The distribution map and corresponding nucleotide sequence information can be embodied in electronic form comprises, e.g., as an accessible computer data on a machine-readable media. "Media" refers to a manufacture, that contains the distribution map, which can include corresponding sequence information, as described herein, which can be read and accessed by a computer. Such media include, but are not limited to: magnetic storage media, such as a floppy disc, a hard disc storage medium, and a magnetic tape; optical storage media such as CD-ROM; electrical storage media such as RAM and ROM; and hybrids of these categories such as magnetic/optical storage media. One of skill in the art can readily appreciate how any of the presently known computer readable mediums can be used to create a manufacture comprising a recording of the present sequence information.

"Recorded" refers to a process for storing information on computer readable medium, using any such methods as known in the art. Any convenient data storage structure can be chosen, based on the means used to access the stored information. A variety of data processor programs and formats can be used for storage, e.g. word processing text file, database format, etc. The distribution map and sequence information can be provided in conjunction or connection with other computer-readable information and/or other types of computer-readable files (e.g., searchable files, executable files, etc, including, but not limited to, for example, search program software, etc.).

By providing the distribution map and sequences in computer readable form, the information can be accessed for a variety of purposes. Computer software to access sequence information is publicly available. For example, the gapped BLAST (Altschul et al. *Nucleic Acids Res.* (1997) 25:3389-3402) and BLAZE (Brutlag et al. *Comp. Chem.* (1993) 17:203) search algorithms on a Sybase system can be used to identify open reading frames (ORFs) within the genome that contain homology to ORFs from other organisms.

As used herein, "a computer-based system" refers to the hardware means, software means, and data storage means used to analyze the nucleotide sequence information of the present invention. The minimum hardware of the computer-based systems of the present invention comprises a central processing unit (CPU), input means, output means, and data storage means. A skilled artisan can readily appreciate that any one of the currently available computer-based system are suitable for use in the present invention. The data storage means can comprise any manufacture comprising a recording of the present sequence information as described above, or a memory access means that can access such a manufacture.

A variety of structural formats for the input and output means can be used to input and output the information in the computer-based systems of the present invention. One format for an output means ranks the relative expression levels of different polynucleotides. Such presentation provides a skilled artisan with a ranking of relative frequencies of markers in a sample to facilitate analysis and identification of regions associated with a condition of the test subjects.

The distribution map, which can include the sequences of the markers, can be stored on the machine-readable medium in connection with an executable program to facilitate its display and analysis. The distribution map can be used to select polymorphic markers suitable for analysis of a desired region. Such markers can include any combination of at least 50, 100, 500, 1,000, 2,500, 5,000, 10,000, or more of the makers of SEQ ID NOS: 1-27,088.

The computer-readable medium carrying the microsatellite polymorphic marker distribution map also carries one or more sequences of instructions from a user of a computer system for performing, over a desired human genomic region, analysis, searches, and displaying results of searches or analysis, of information regarding the markers within the desired genomic region. Analysis can include, for example, analysis of frequency data for said markers with respect to a characteristic of interest for a human population of interest. The frequency data can be provided by the manufacturer on the medium, or can be input and stored by the user, e.g., as in during the course of marker analysis.

The medium contains information regarding the position of microsatellite polymorphic markers over one or more regions of the human genome, e.g, the position of the markers within a chromosomal region, more usually over one or more regions on 2 or more, 5 or more, 10 or more chromosomes of the human genome. In one embodiment, the entire human genome is mapped with microsatellite markers, including 23 single chromosomes (i.e., 22 autosome and an X or Y sex chromosomes). The microsatellite genetic polymorphism markers are located on the human genome map in intervals of at least about 50 to 150 Kb, usually at least about 80 to 120 Kb, more usually at least about 90 to 110 Kb, said markers usually being positioned at intervals of from about 50 Kb to 150 Kb. The map and thus the computer-readable medium can also include carries sequence information for the markers, where the markers can be any combination of SEQ ID NOS:1-27808.

The medium additionally carries one or more sequences of instructions for execution, at the direction of the user, by one or more processors so as to cause the one or more processor to perform a method. The method can involve, for example receiving a query inputted by the user and receiving instructions as to microsatellite markers and/or a human genomic region to include in analysis; accessing distribution map information stored on the medium; displaying on a display means (e.g., a monitor or screen) a map showing the position of markers on a human genomic region, where the map provides at least the selected markers or markers within the selected region.

Kits

Also provided are reagents and kits thereof for practicing one or more of the above-described methods. The subject reagents and kits thereof may vary greatly. Typically, the kits at least include one or more primer pairs, normally 20 or more, 50 or more 500 or more, 1,000 or more primer pairs, where the primer pairs re forward and reverse primers as described above for amplification of a combination of polymorphic markers of SEQ ID NOS:1-27088 or for amplification of a region associated with psoriasis vulgaris. The primers can be appropriately detectably labeled to facilitate analysis. The subject kits may also include one or more additional reagents, e.g., reagents employed in detecting the detectable label.

In addition to the above components, the subject kits can further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. The computer-readable format can also include the distribution map as described above. Yet another means that may be present is a website address which may be used via the internet to access the information at a removed site. Any convenient means may be present in the kits.

EXAMPLES

Example 1

(1) Sampling of DNA Samples

Genetic analysis was performed using blood samples of patients suffering from each disease and healthy subjects, which are controls, collecting blood of 10 to 20 ml from 464 Japanese healthy subjects who have agreed to participate in the study, 306 patients with rheumatoid arthritis, and 118 patients with psoriasis vulgaris is carried out, and DNA samples are then collected.

It is noted that this study was made upon examination and approval by the Japan Biological Information Consortium Committee for Ethical Examination, Tokai University Research of Human Genome and Genetic Analysis Committee for Ethical. Examination, University of Tokyo Graduate School of Medicine and Faculty of Medicine, Research Committee for Ethical Examination, Juntendo University Faculty of Medicine Research Ethical Committee.

(2) Preparation of DNA Samples

Preparation of DNA samples was carried out in conformity with the following procedure. Extraction and purification of the genome DNA from the collected blood is carried out using QIAamp DNA Blood Maxi Kit (QIAGEN). Considering a possible influence to amplification efficiency for PCR, T. E. (10 mM Tris-HCl, 0.1 mM EDTA), which is one tenth the normal EDTA concentration, is used to extract the genome DNA from columns. Once extraction is accomplished, agarose gel electrophorsis is carried out so as to determine that decomposition of DNA does not occur, and also to find the purity based on the measured absorbance or 260/280 ratio.

Measurement of DNA and preparation of mixed DNA (pooled DNA) solution are carried out in conformity with the following procedure. A fluorescence plate reader and the fluorescent pigment PicoGreen reagent (Molecular Probes), which stains a double strand DNA specifically, are used to measure DNA. $\lambda$ phage DNA attached to the PicoGreen reagent is used as standard samples to be used for concentration measurement, which include five-point dilution sequences of 10, 30, 100, 300, and 1000 pg/mL. The genome DNA of each individual is diluted into 1/400, and measurements are then carried out three times for the respective sequences. From the results of the three-time measurements, a total of three combinations of two were made, and average values, S.Ds. and C.Vs. are calculated for the respective combinations. The combination with a C.V. of 5% or less and being the lowest value is selected, and the corresponding average is then used as the final DNA concentration. If the respective C.Vs. for all of the three combinations exceeds 5%, measurement of the DNA is carried out repeatedly until a combination with 5% or less is found.

Based on the DNA concentration determined by such operation and measurement, fixed DNA amounts from DNA samples of 125 subjects were mixed together, and T.E. (10 mM Tris-HCl, 0.1 mM EDTA) is added thereto to obtain an 8 ng/µL pooled sample. To perform the first and the second screening, two sets of such pooled DNA sample for the 125 subjects were prepared for each patient group and healthy subject group. It is noted that the sex ratio for the 125 subjects in each set is selected so that it can be equal between the pooled DNA samples for each patient group and those for the healthy subject group, and the age distribution is selected so that it can also be almost equal between them in the 10-year-old class.

(3) Preparation of DNA Sequence Fragment Group Including Microsatellite Genetic Polymorphism Markers (Pooled DNA Genotyping)

A set of a forward primer and reverse primer each having 15 to 100 nucleotides, preferably 15 to 25 nucleotides, more preferably 18 to 22 nucleotides, which are obtained from the DNA sequence made up of the nucleotide sequences of SEQ ID NOS: 1 to 27088, was used to amplify a DNA sequence fragment groups including microsatellite genetic polymorphism markers. The forward primer with its 5'-terminus fluorescently labeled with 6-FAM or HEX(PE Biosystems, Foster City, Calif.) was used whereas the reverse primer is not labeled.

Preparation of a reactive solution for PCR is performed in conformity with the following procedure. The preparation was made such that a 24 ng pooled DNA sample (i.e., 3 µL×8 ng/µL), 2 µL/10× buffer (100 mM Tris-HCl, pH 8.3, 500 mM KCl, and 15 mM MgCl2), 2 pmol forward primer and reverse primer, and 0.5 U AmpliTaq DNA polymerase (Applied Biosystems) were included in a 20 µL reactive solution. The PCR cycle includes: one cycle consisting of processing carried out for 5 minutes at 96° C., 1 minute at 56° C., and 1 minute at 72° C., and 40 cycles consisting of processing carried out for 45 minutes at 96° C., 45 seconds at 57° C. and 45 seconds at 72° C.

The PCR products obtained were diluted with ultra pure water into 1/20 or 1/40, dried by a vacuum pump or an evaporator, and then dissolved in a buffer containing formamide (Applied Biosystems) and DNA size marker GS500 ROX (Applied Biosystems). Afterwards, they were heat-treated for 5 minutes, and then electrophoresed by DNA analyzer ABI 3700 followed by being subjected to determining, using the GeneScan analysis software (Applied Biosystems), the size of each fluorescence signal peak derived from the PCR products. After this operation, each peak size and height were measured using the PickPeak software so as to make data for analysis.

(4) Statistical Calculation

For each MS genetic polymorphism marker whose DNA sequence-was included, comparison of the estimated allele frequencies obtained from the pooled DNA samples for a patient group and pooled DNA samples for a healthy subject group was performed using statistical processing based on the chi-square test and the Fisher test so as to make a genetic correlation analysis. This analysis was performed as follows.

The total of the heights of fluorescence signal peaks derived from the detected PCR products was calculated for each gene locus (MS genetic polymorphism marker). With this as the denominator, the ratio of each allele peak height was calculated to be the gene frequency for each allele within a group. In the statistical processing, an allele number for each allele within a group was found by multiplying the total allele number for the sample included in the pooled DNA sample, and using this allele number, a test regarding the difference among the allele frequencies of the healthy subject group and the patient group is carried out.

Moreover, for genetic correlation analysis using pooled DNA samples based on the above-described method, 2×2 and 2×m divided tables were made to calculate statistic values through the chi-square test and the Fisher test. These results allow optimization of the genetic correlation analysis using pooled DNA samples. Methods for performing a quick analysis are thus studied and corresponding software is developed.

Example 2

Specification of Susceptibility Gene for Psoriasis Vulgaris

Using the method described in Embodiment 1, genome correlation analysis of the susceptibility gene for psoriasis vulgaris is carried out. This screening allows identification of the gene locus extending from the centromeric MICB gene of the sixth chromosome to the telomeric HLA-F gene, and identification of 758 microsatellite loci having 2- to 5-nucleotide repeats existing within the 1.8 Mb HLA class I region including the HLA-B and the HLA-C gene. This fact corresponds to conventional reports (Mizuki N. et al. (1997) Genomics, 42, 55-66; Shiina T. et al. (1998) Genomics, 47, 372-382; Shiina T. et al. (1999) Immunol Rev., 167, 193-199; Tamiya G. et al. (1998) Tissue Antigens, 51, 337-346).

Among these microsatellites, 70 were analyzed for their polymorphism content in the Japanese population. Of these, 38 are found to be highly informative with an average of 66% heterozygosity and an average of 8.9 alleles (Tamiya G. et al. (1998) Tissue Antigens, 51, 337-346; Tamiya G. et al. (1999) Tissue Antigens, 54: 221-228). These 38 microsatellite repeats are selected for high resolution mapping.

Combined with the seven previously known polymorphic genes and microsatellites [MICB, MICA, HLA-B, HLA-C, HLA-A, MIB (Grimaldi M. C. et al. (1996) Hum. Immunol., 51, 89-94), and D6S265 (Weissenbach J. et al. (1992) Nature, 29, 794-801)], a total of 45 informative genetic markers, i.e. one every 41.1 kb, were defined within the HLA class I region. It is considered that this high density polymorphism marker allows acquisition of exact information regarding the haplotype analysis and mapping analysis of psoriasis vulgaris HLA class I related diseases.

Example 3

Specification of Susceptibility Gene for Psoriasis Vulgaris (2)

Next, to determine the definite position of the causative gene for psoriasis vulgaris within the HLA class I region, association analyses are conducted using 11 of these 38 repeats.

These eleven microsatellites are selected so that they can be distributed around the HLA-C gene locus of the sixth chromosome at the rate of one in 100 kb.

Correlation analysis targets the psoriasis vulgaris patient group and the healthy subject group described in Example 1. The patient group consists of 51 males and 25 females with an average onset age of 33 years (SD=15.3).

To determine the number of repeat units of the eleven genetic polymorphism microsatellite loci (genotype of microsatellite allele), the reverse primer and forward primer with 20 to 28 nucleotides are synthesized from the MS genetic polymorphism marker included DNA sequence. It is noted that this synthesizing uses the fluorescent reagent 6-FAM, HEX, or TET (PE Biosystems (presently Applied Biosystems), Foster City, Calif.) so as to label the 5'-terminus of the forward primer. Table 1 shows eleven sets of the primers, i.e., twenty-two in all.

TABLE 1

Microsatellite markers used for correlation analysis

| Micro-Satellite | Localization | Repeat unit | PCR primer |
| --- | --- | --- | --- |
| C1_2_A | Tel. (0 kb)/MICB<br>Cen.(89 kb)/MICA | $(CA)_{23}$ | CA:AATAGCCATGAGAAGCTATGTGGGGGAG<br>TG:CTACCTCCTTGCCAAACTTGCTGTTTGTG |
| C1_4_1 | Tel. (40 kb)/MICA<br>Cen.(6 kb)/HLA-B | $(CAAA)_6$ | CAAA:CGAGAACAACTGGCAGGACTG<br>TTTG:GACAGTCCTCATTAGCGCTGAGG |
| C1_2_5 | Tel. (62 kb)/HLA-B<br>Cen.(19 kb)/HLA-C | $(CA)_4AA(CA)_{20}$ | CA:CAGTAGTAAGCCAGAAGCTATTAC<br>TG:AAGTCAAGCATATCTGCCATTTGG |

TABLE 1-continued

Microsatellite markers used for correlation analysis

| Micro-Satellite | Localization | Repeat unit | PCR primer |
|---|---|---|---|
| C1_4_3 | Tel. (26 kb)/HLA-C<br>Cen.(71 kb)/OTF3 | $(GGAA)_{18}$ | GGAA:TAGAAAACGCAATCTCGGCC<br>TTCC:CTGGATTAACCTGGAGACTC |
| C1_3_1 | Tel. (27 kb)/HLA-C<br>Cen.(69 kb)/OTF3 | $(TTG)_8$ | TTG:CAGTGACAAGCACCTGGCAC<br>CAA:GCCAGATGTGGTGGCATGC |
| C1_2_6 | Tel. (85 kb)/HLA-C<br>Cen.(11 kb)/OTF3 | $(TA)_{17}$ | TA:TGTTCAGACCTCTTCCTGCC<br>AT:GACTAGCTCTTGACTACTTG |
| C1_3_2 | Tel. (37 kb)/OTF3<br>Cen.(7 kb)/S | $(TAA)_{16}$ | TAA:TAGGGATGGTCCCAAACGTG<br>TTA:CCCGTGCAGGACTGATCTCC |
| C2_4_4 | Tel. (80 kb)/S | $(GAAA)_6AAAA(GAAA)_3$ | GAAA:GGCTTGACTTGAAACTCAGAGACC<br>TTTC:TTATCTACTTATAGTCTATCACGG |
| C4_2_12 | Tel. (75 kb)/DDR<br>Cen.(89 kb)/TUBB | $(CA)_{13}$ | CA:GAGCCACGGAGAGTCTCCCTTTATC<br>TG:TCCAGGAACTGTGAGTAGTAAGAAC |
| C4_2_25 | Tel. (69 kb)/TUBB<br>Cen.(47 kb)/HSGT260 | $(TG)_{16}$ | TG:TCTTCTGTGCAAGCAATGCACTGTAC<br>CA:ATGTTACTTTTAGAAGATAACACTC |
| C3_2_11 | Tel. (50 kb)/HLA-E<br>Cen.(21 kb)/MICC | $(GA)_{22}TA(GA)_8$ | GA:AGATGGCATTTGGAGAGTGCAG<br>TC:TCCTTACAGCAGAGATATGTGG |

Eleven selected microsatellite genetic polymorphism markers and PCR primer sequence numbers are listed here. The numbers on the left denote the sequence numbers for the forward primer, while the numbers on the right denote the sequence numbers for the reverse primer.

C1-2-A; SEQ ID NO:27089: SEQ ID NO:27090
G1-4-1; SEQ ID NO:27091: SEQ ID NO:27092
C1-2-5; SEQ ID NO:27093: SEQ ID NO:27094
C1-4-3; SEQ ID NO:27095: SEQ ID NO:27096
C1-3-1; SEQ ID NO:27097: SEQ ID NO:27098
C1-2-6; SEQ ID NO:27099: SEQ ID NO:27100
C1-3-2; SEQ ID NO:27101: SEQ ID NO:27102
C2-4-4; SEQ ID NO:27103: SEQ ID NO:27104
C4-2-12; SEQ ID NO:27105: SEQ ID NO:27106
C4-2-25; SEQ ID NO:27107: SEQ ID NO:27108
C3-2-11; SEQ ID NO:27109: SEQ ID NO:27110

The PCR reactive mixture was prepared to contain 50 ng genomic DNA, 2 μl dNTP (2.5 mM each), 2 μl/10× buffer (100 mM Tris-HCl, pH 8.3, 500 mM KCl, 15 mM MgCl$_2$), and 20 pmol forward and reverse primers as well as 0.5 U Takara recombinant Taq polymerase (Takara Shuzo, Kyoto, Japan) in a total volume of 20 μl. After initial denaturation for 5 minutes at 96° C., processing was carried out using an automated thermal cycler (Takara Shuzo) for 30 cycles consisting of 1 minute at 96° C., 30 seconds at 55° C. and 45 seconds at 72° C., with a final extension of 4 minutes at 72° C. The amplified products were denatured for 5 minutes at 100° C., mixed with formamide-containing stop buffer, applied with a size standard marker of GS5OO Tamra (PE Biosystems) to the starting position of each lane, and run on a 4% polyacrylamide denaturing sequencing gel containing urea in an automated DNA sequencer. Fragment sizes are determined automatically using the GeneScan software (PE Biosystems).

The results are shown in FIG. 1, with the following notations: a) gene map showing the location of each gene in the HLA class I region from IkBL to HLA-L. Black and white boxes represent the HLA-class I genes and the non-HLA genes, respectively. Arrows indicate the orientations of genes; b) Statistical analysis by the case-control correlation test and the exact test of Hardy-Weinberg proportion. The curve is drawn as smoothly fitted on the basis of a two-point moving average in each test. Open circles with solid line indicates Pc-values obtained by Fisher's exact test in the case-control correlation test; open squares with dashed line indicates P-values obtained by the exact test in terms of deviation from Hardy-Weinberg proportions (the probability test); closed spares with bold solid line indicates P-values obtained in the patients by the exact test in terms of heterozygote deficiency against the null hypothesis of Hardy-Weinberg equilibrium; c) Locations of microsatellite markers with the distance (kb) from the HLA-C locus to each microsalellite in parentheses.

The order of the MS genetic polymorphism markers from the centromeric towards the telomeric is C1_2_A, C1_4_1, C1_2_5, C1_4_3, C1_3_1, C1_2_6, C1_3_2, C2_4_4, C4_2_12, C4_2_25, and C3_2_11 (FIG. 1). Repeat units are determined from sequencing data previously obtained by the present inventors (Shiina T. et al. (1999) Immunol. Rev., 167: 193-199). All MS genetic polymorphism markers are established by Tamiya et al. (Tamiya G. et al. (1998) Tissue Antigens, 51, 337-346; Tamiya G. et al. (1999) Tissue Antigens, 54: 221-228).

"Tel" indicates the telomeric, and "Cen.", the centromeric. The PCR primer sequences in order from top of the list are numbered SEQ ID NO:27089 to SEQ ID NO:27110.

Allele frequencies were estimated by direct counting. The test of significance for the distribution of alleles between the patients and the controls was conducted through the chi-square test, which performs correction for continuity, and Fisher's exact test (P-value test). The P-value was corrected by multiplying by the number of microsatellite alleles observed in each locus (Pc). A level of A calculated from the 2×2 contingency table. The exact P-value test of the Hardy Weinberg proportion for multiple alleles is simulated based on the Markov chain method within the Genepop software package (Tamiya G. et al. (1998) Tissue Antigens, 51, 337-346; Tamiya G. et al. (1999) Tissue Antigens, 54: 221-228; Guo S. W. and Thompson E. A. (1992) Biometrics, 48: 361-372). The Markov chain method has the advantage of giving a complete enumeration for testing the Hardy Weinberg proportion in cases where the number of alleles as well as sample size are small. When the number of alleles is below 5, the exact P-value is calculated by the complete enumeration method. A level of P<0.1 is accepted as statistically significant for the Hardy-Weinberg equilibrium test.

In the patients, the phenotype frequency of HLA-Cw6 (8/76 patients, 10.5%) is significantly increased, with a Pc-value of 0.02 (odds ratio=15.88). As shown in Table 2, alleles showing statistically significant differences in Pc-values below 0.05 in the patient group are found at the four microsatellite loci: allele 303 ($\chi^2$=12.62, Pc=0.0015) in C1__2__6; 357 ($\chi^2$=7.91, Pc=0.0034) in C1__8__2; 255 and 259 ($\chi^2$=9.53, Pc=0.0012 and $\chi^2$=11.58, Pc=0.0022, respectively) in C2__4__4; and 223 ($\chi^2$=7.59, Pc=0.036) in C4__2__12. Alleles in each microsatellite genetic polymorphism marker are named on the basis of the length of the amplified fragment.

The most significant correlation was obtained for the allele 303 in the C1__2__6 locus. All four microsatellites in the segment from the loci C1__2__6 to C4__2__12 exhibited statistically significant differences in their allele frequencies between the patients and controls (Table 2 and FIG. 1).

The exact test of Hardy-Weinberg proportion was also carried out for the above 11 microsatellite genetic polymorphism markers by the Markov chain method (Guo S. W. and Thompson E. A. (1992) Biometrics, 48: 361-372) in terms of deviation from Hardy-Weinberg proportions (the probability test) and heterozygote deficiency against the null hypothesis of Hardy-Weinberg equilibrium (Raymond M. and Rousset F. (1995) J. Hered., 86: 248-249; Rousset F. and Raymond M. (1995) Genetics, 140:1413-1419).

All of the tested 11 MS genetic polymorphism markers follow the Hardy-Weinberg equilibrium in the healthy controls (P>0.25), as expected. In contrast, five loci deviate significantly from the Hardy-Weinberg equilibrium in the patient group (P<0.1: C1__2__5, C1__3__1, C1__2__6, C1__3__2, and C2__4__4), as listed in Table 3. Furthermore, five loci show a significant decrease in heterozygotes (P<0.1: C1__4__3, C1__3__1, C1__3__2, C2__4__4, and C4__2__12). On the other hand, no increase in heterozygotes is observed for any MS genetic polymorphism markers. It must be noted that the three microsatellite loci (C1__3__1, C1__3__2, and C2__4__4) in the segment from C1__3__1 to C2__4__4 displays significant P-values in both probability and heterozygote deficiency tests (Table 3 and FIG. 1). In particular, in C1__3__2 and C2__4__4, highly significant P-values are obtained in both of these tests.

TABLE 3

Exact test of the Hardy-Weinberg proportion for microsatellites

| Loci | HW[a] | SE | Hetero.[b] | SE | Ex. Hetero.[c] | Ob. Hetero.[d] |
|---|---|---|---|---|---|---|
| C1__2__A | 0.3939 | 0.0043 | 0.2881 | 0.0042 | 0.801 | 0.763 |
| C1__4__1 | 0.2443 | 0.0016 | 0.7024 | 0.0019 | 0.633 | 0.613 |
| C1__2__5 | <u>0.0063</u> | 0.0006 | 0.1599 | 0.0042 | 0.883 | 0.842 |
| C1__4__3 | 0.1968 | 0.0065 | <u>0.0362</u> | 0.0028 | 0.89 | 0.829 |
| C1__3__1 | <u>0.0286</u> | — | <u>0.0203</u> | — | 0.561 | 0.461 |
| C1__2__6 | <u>0.0889</u> | 0.0023 | 0.1776 | 0.0027 | 0.676 | 0.579 |
| C1__3__2 | <u>0.0172</u> | 0.0005 | <u>0.0051</u> | 0.0003 | 0.848 | 0.75 |
| C2__4__4 | <u>0.0097</u> | 0.0004 | <u>0.0093</u> | 0.0003 | 0.655 | 0.553 |
| C4__2__12 | 0.3006 | 0.0052 | <u>0.0303</u> | 0.0013 | 0.679 | 0.635 |

TABLE 2

Statistically significant alleles that correlate with psoriasis vulgaris

| Loci | Distance from HLA-C a) | No. of alleles | Allele | Odds ratio | CI of odds ratio | X² | P-value b) | Pc-value c) |
|---|---|---|---|---|---|---|---|---|
| C1__2__A | 232 kb(c) | 10 | 242 | 0.44 | 024-0.81 | 6.97 | 0.0059 | 0.059 |
| C1__4__1 | 91 kb(c) | 5 | 221 | 0.59 | 0.31-1.11 | 2.66 | 0.069 | 0.345 |
| C1__2__5 | 19 kb(c) | 14 | 216 | 2.58 | 1.59-5.08 | 7.54 | 0.0057 | 0.0798 |
| C1__4__3 | 29 kb(t) | 17 | 467 | 0.16 | 0.04-0.59 | 7.52 | 0.0037 | 0.0629 |
| C1__3__1 | 31 kb(t) | 4 | 291 | 0.49 | 0.27-0.89 | 5.57 | 0.013 | 0.052 |
| C1__2__6 | 89 kb(t) | 8 | 303 | 0.21 | 0.09-0.50 | 12.62 | 0.00019 | <u>0.00152</u> |
| C1__3__2 | 143 kb(t) | 8 | 357 | 2.37 | 1.30-4.32 | 7.91 | 0.0042 | <u>0.0336</u> |
| C2__4__4 | 200 kb(t) | 6 | 255 | 2.76 | 1.45-5.25 | 9.53 | 0.002 | <u>0.012</u> |
| C2__4__4 | | | 259 | 0.24 | 0.11-0.55 | 11.58 | 0.00037 | <u>0.00222</u> |
| C4__2__12 | 457 kb(t) | 9 | 223 | 0.33 | 0.73-0.15 | 7.59 | 0.004 | <u>0.036</u> |
| C4__2__25 | 618 kb(t) | 7 | 271 | 5.06 | 0.56-45.1 | 2.11 | 0.2 | 1 |
| C3__2__11 | 831 kb(t) | 17 | 209 | 0.55 | 0.26-1.17 | 2.43 | 0.082 | 1 |

Table legend:
a) (c), centromeric HLA-C gene; (t), telomeric HLA-C gene.
b) Determined by Fisher's exact test.
c) Corrected by multiplying by the number of microsatellite alleles observed in each locus.
Pc-values below 0.05, accepted as statistically significant, are underlined.

TABLE 3-continued

Exact test of the Hardy-Weinberg proportion for microsatellites

| Loci | HW[a] | SE | Hetero.[b] | SE | Ex. Hetero.[c] | Ob. Hetero.[d] |
|---|---|---|---|---|---|---|
| C4__2__25 | 0.666 | 0.0041 | 0.6684 | 0.007 | 0.466 | 0.481 |
| C3__2__11 | 0.1837 | 0.0057 | 0.4787 | 0.0078 | 0.9 | 0.895 |

[a]Deviation from Hardy-Weinberg proportions (probability test).
[b]Heterozygote deficiency against the null hypothesis of the Hardy-Weinberg equilibrium.
[c]Expected helerozygote frequency in the patient population.
[d]Observed heterozygote frequency in the patient population.

In the above table, the exact P-value is estimated by the simulations based on the Markov chain method with the following parameters: dememorization number=1000; number of batches=400; number of iteration per batch=8000. When the number of alleles is below 5, the exact P-value is calculated by the complete enumeration method. Pc-values below 0.1, accepted as statistically significant, are underlined. SE, standard error.

As indicated above, four of the analyzed microsatellites (C1_2_6, C1_3_2, C2_4_4, and C4_2_12) in the segment from C1_2_6 to C4_2_12 display statistically significant differentiation between the patients and controls (Table 2 and FIG. 1). Moreover, the three microsatellite loci (C1_3_1, C1_3_2, and C2_4_4) in the segment from C1_3_1 to C2_4_4 display significant deviation in both probability and heterozygote deficiency tests (Table 3 and FIG. 1). In particular, in C1_3_2 and C2_4_4, highly significant P-values are obtained in both of these tests.

Although the mode of inheritance of psoriasis is unclear, Table 2 makes it clear that the frequency of heterozygotes at the five microsatellite loci in the patients is lower than the expected suggests a recessive HLA trait for this disease, although the genetic penetrance is not high. Collectively, it can be concluded that the 111 kb segment from C1_2_6 (89 kb telomeric HLA-C) to C2_4_4 (200 kb telomeric HLA-C) is the common area critical for psoriasis vulgaris at a confidence level of more than 95%, as assessed by both statistical methods for allelic distribution and deviation on the Hardy-Weinberg equilibrium (FIG. 1).

It must be emphasized that these two independent statistical methods, of which the former deals with the data of patients and controls and the latter only with the data of patients, reveals an almost identical critical segment for psoriasis vulgaris. This result is consistent with previous mapping data Which showed the susceptibility gene for psoriasis vulgaris to be residing on the telomeric HLA-C gene, based on a transmission/disequilibrium test (TDT) and parametric linkage analysis using the HLA class I (HLA-A, -B, and -C) and class II (HLA-DRB1 and -DQB1) alleles in the patients (Jenisch S. et al. (1998) Am. J. Hum. Genet., 63, 191-199).

Example 4

Analysis of Susceptibility Gene for Rheumatoid Arthritis

Figure 2:
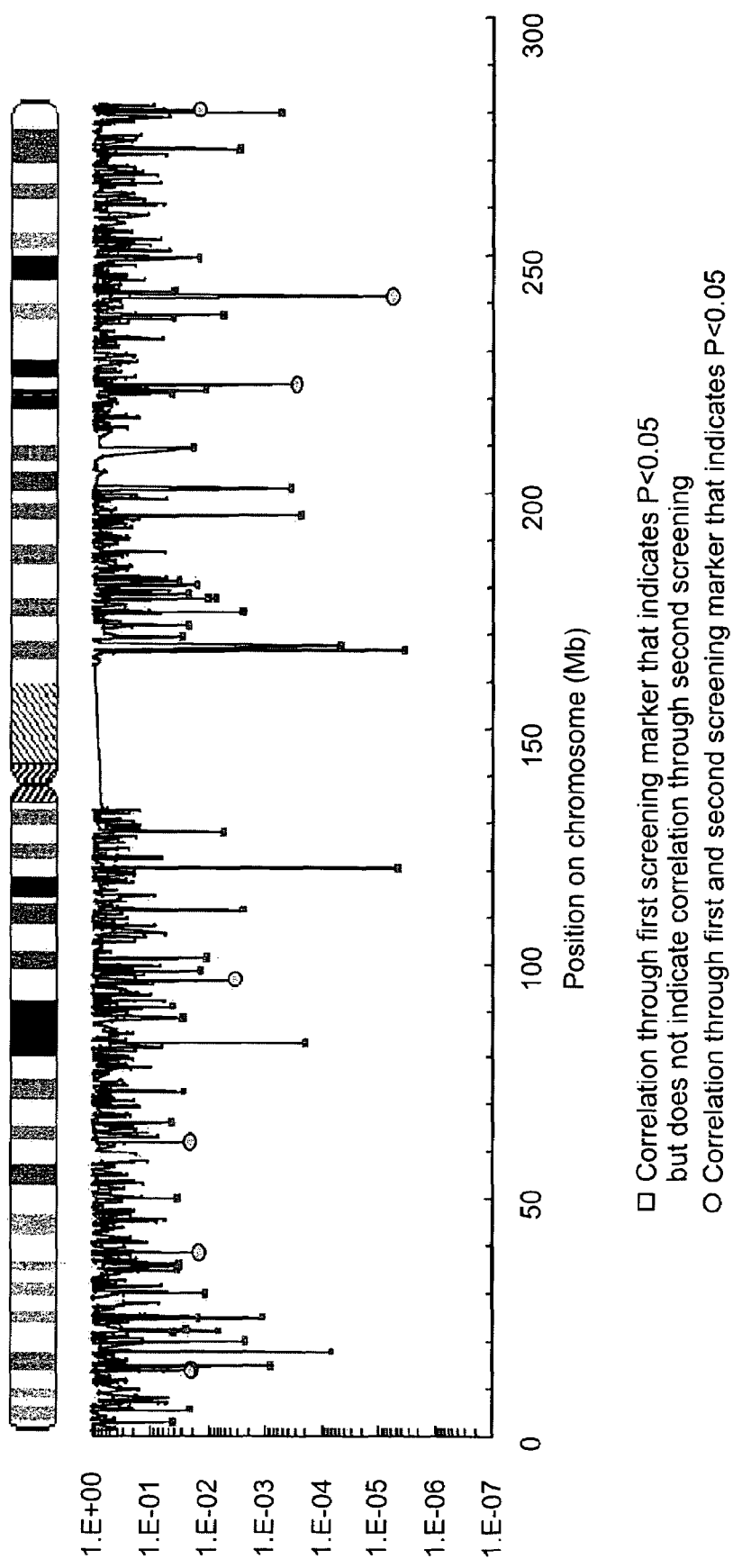
FIG. 2 shows a result of carrying out the first screening of the first chromosome for rheumatoid arthritis.

In the first step of identifying the susceptibility gene for rheumatoid arthritis in which genetic factors are suggested to be involved, a genetic correlation analysis is carried out throughout the genome. Considering the sampling structure for age and sex of patients and healthy subjects, the pooled DNA reagents for analysis of the susceptibility gene for rheumatoid arthritis are adjusted. The sex ratio for the reagents collected from the rheumatoid arthritis patients before the test has begun is 0.212 for men to 0.788 for women. In order to perform the second screening, two pooled DNA reagents (i.e., 125×2) are prepared in accordance with the above sex ratio. The age distribution for this case is illustrated in the ten-year-old class (FIG. 2). The average ages for the reagent pool of to be-compared healthy subjects is shown below:

<Men> Average age: 44.3 SD: 11.8 Sample number: 52
<Women> Average age: 39.1 SD: 12.9 Sample number: 198

Since there is no information regarding onset ages for patients, certain references are referred. The age distribution is surveyed (since the average age is unknown, the age of 45 is given), and in conformity therewith, the pooled DNA reagents for the healthy subjects are prepared.

Screening the pooled DNA samples for the patients and healthy subjects was carried out, as described in Example 1, using primers corresponding to MA genetic polymorphism markers throughout the genome, and the first chromosome and the fourth chromosome (2471 markers) are analyzed first. It is noted that the inter-marker spacing for 57% of the MS genetic polymorphism markers used for the first chromosome and 59% used for the fourth chromosome is below 100 kb.

Figure 3:
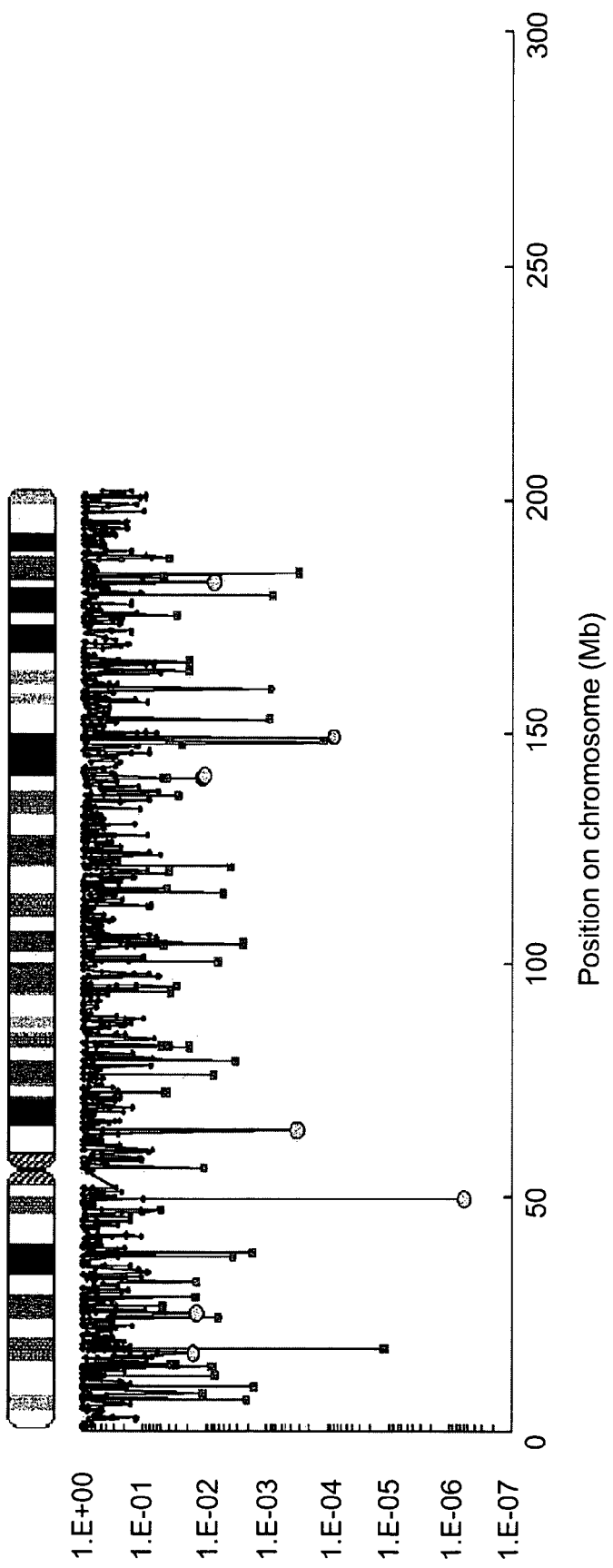
FIG. 3 shows a result of carrying out the first screening of the fourth chromosome for rheumatoid arthritis.
Figure 4:
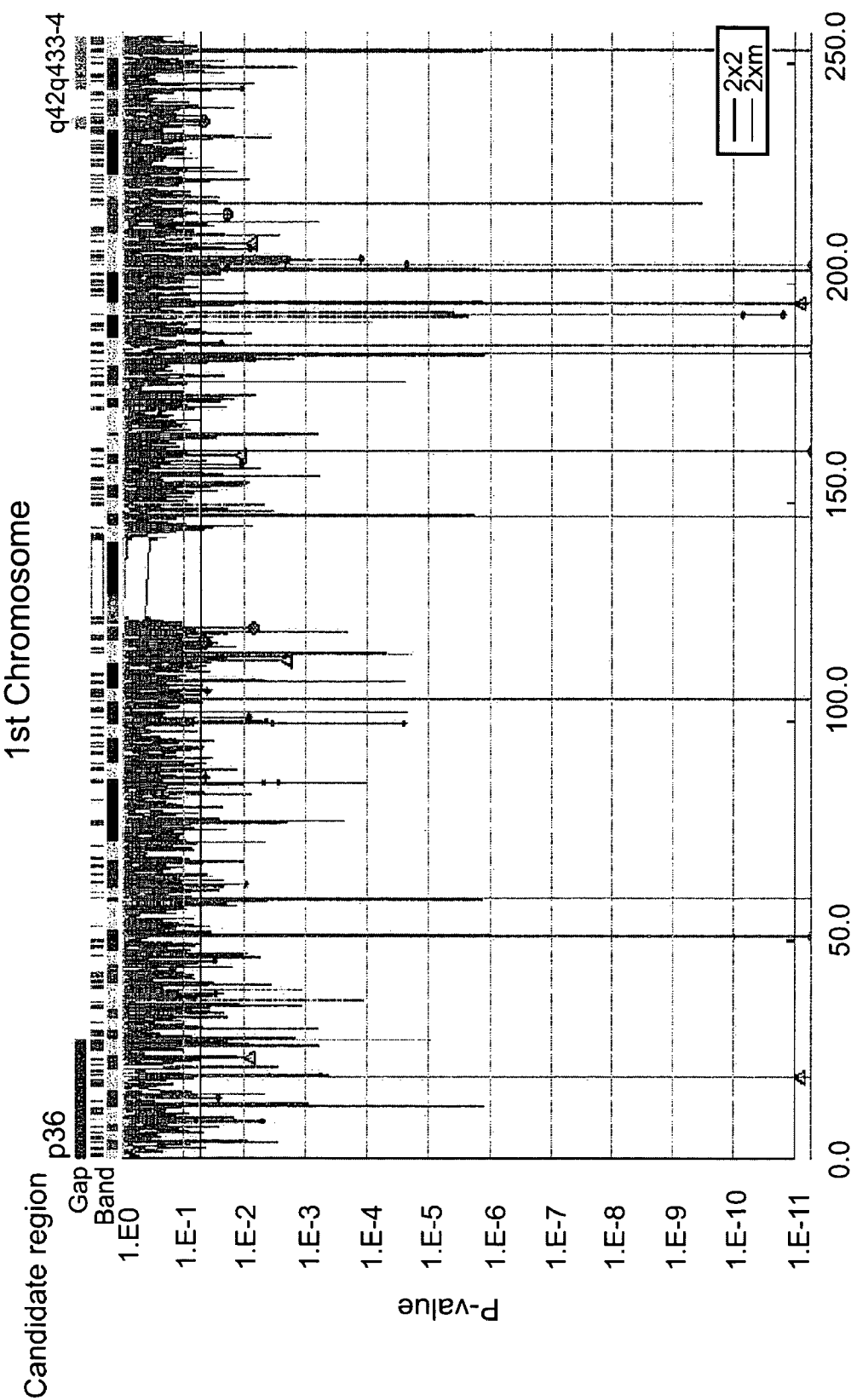
FIG. 4 shows a profile for the rheumatism susceptibility segment in the first chromosome analyzed using a method according to the present invention.
Figure 5:
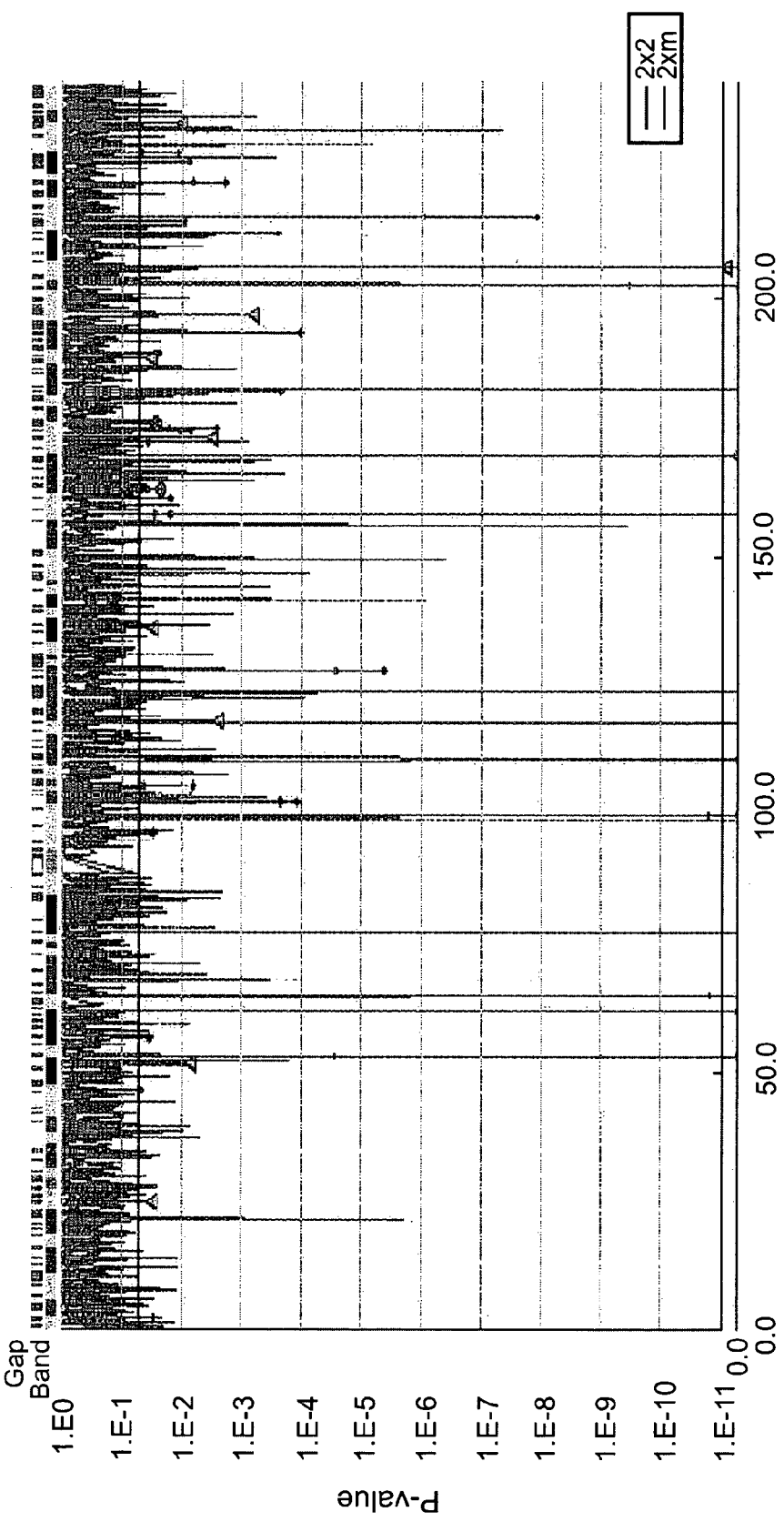
FIG. 5 shows a profile for the rheumatism susceptibility segment in the second chromosome analyzed using a method according to the present invention.
Figure 6:
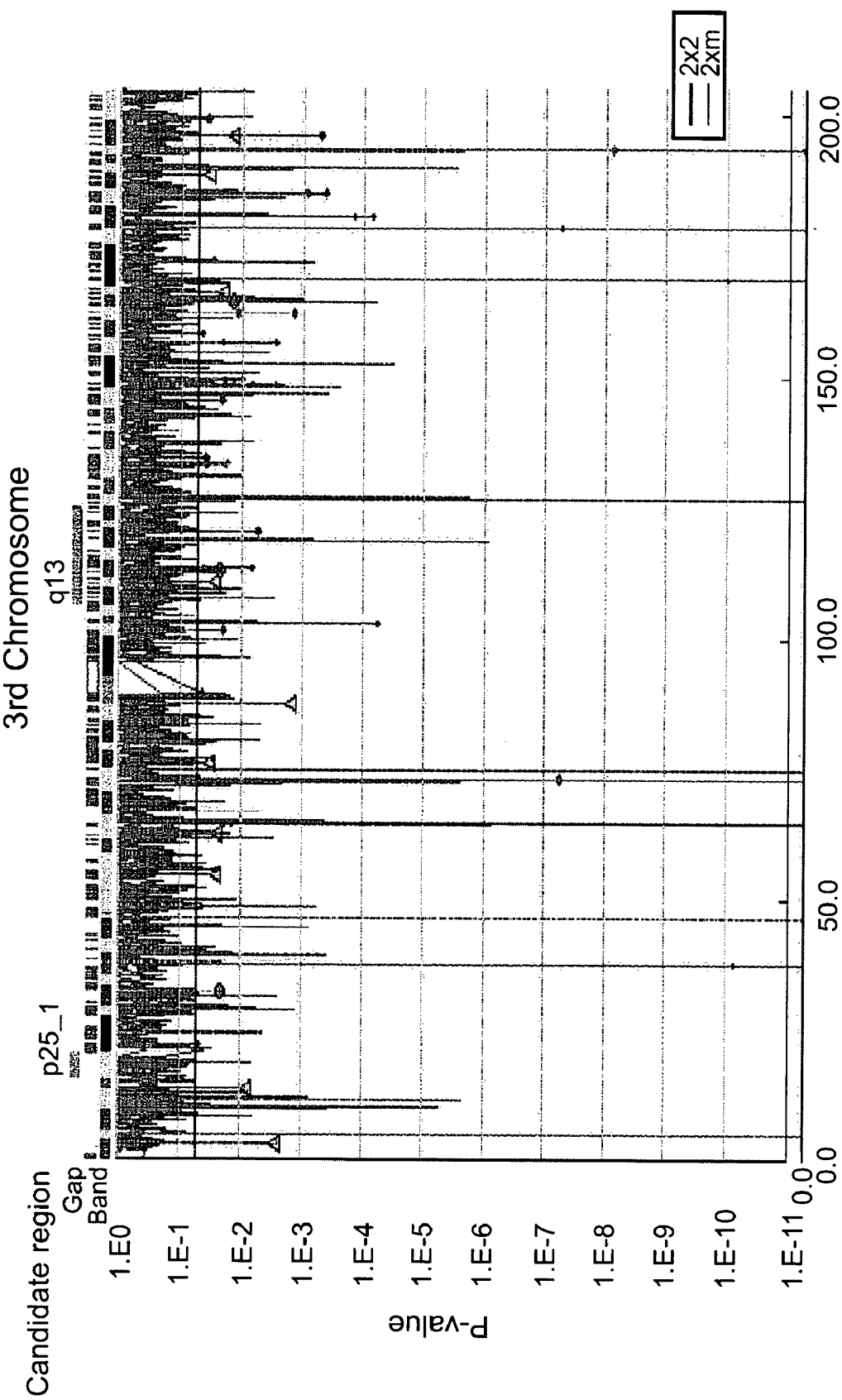
FIG. 6 shows a profile for the rheumatism susceptibility segment in the third chromosome analyzed using a method according to the present invention.
Figure 7:
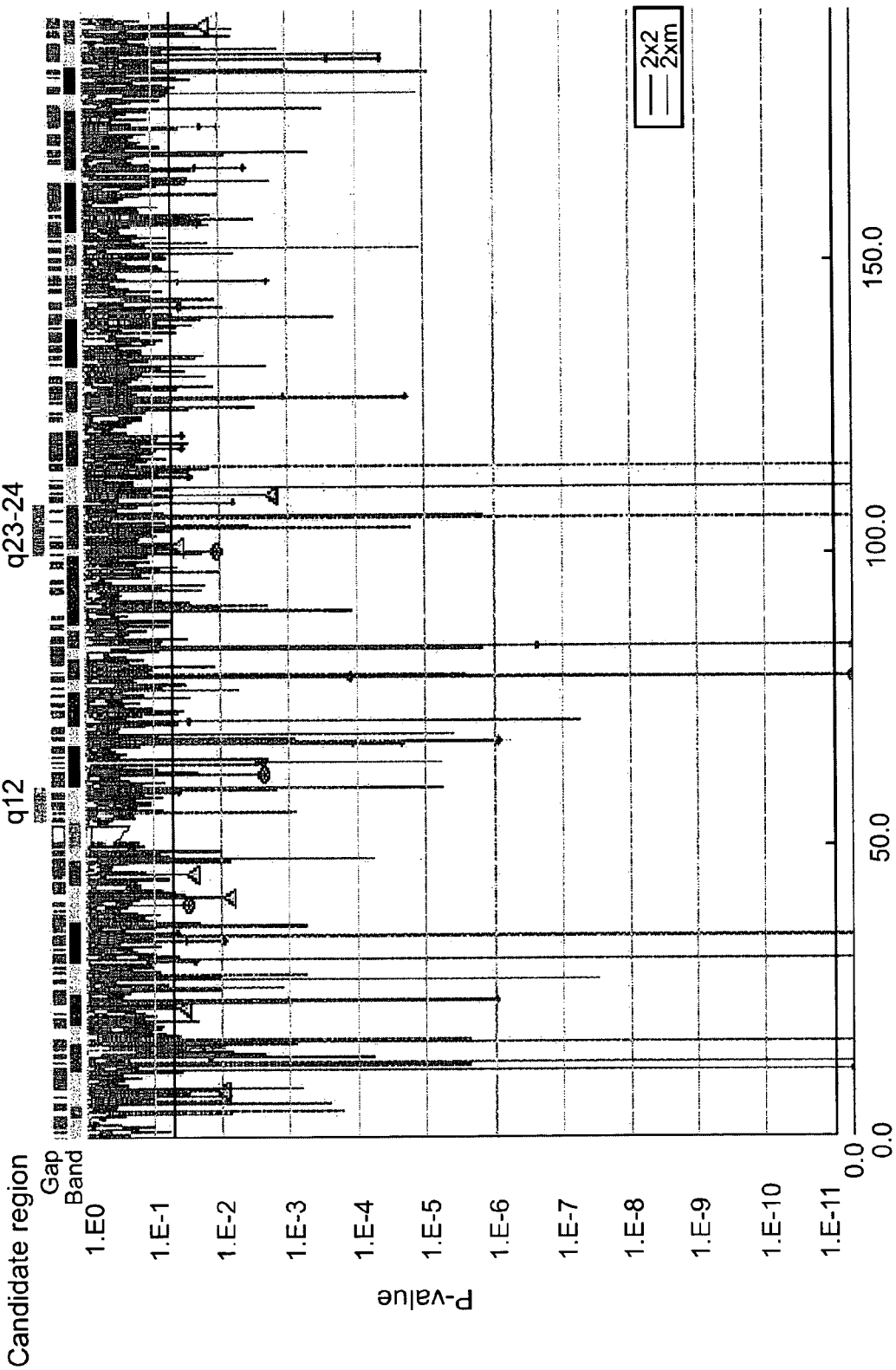
FIG. 7 shows a profile for the rheumatism susceptibility segment in the fourth chromosome analyzed using a method according to the present invention.
Figure 8:
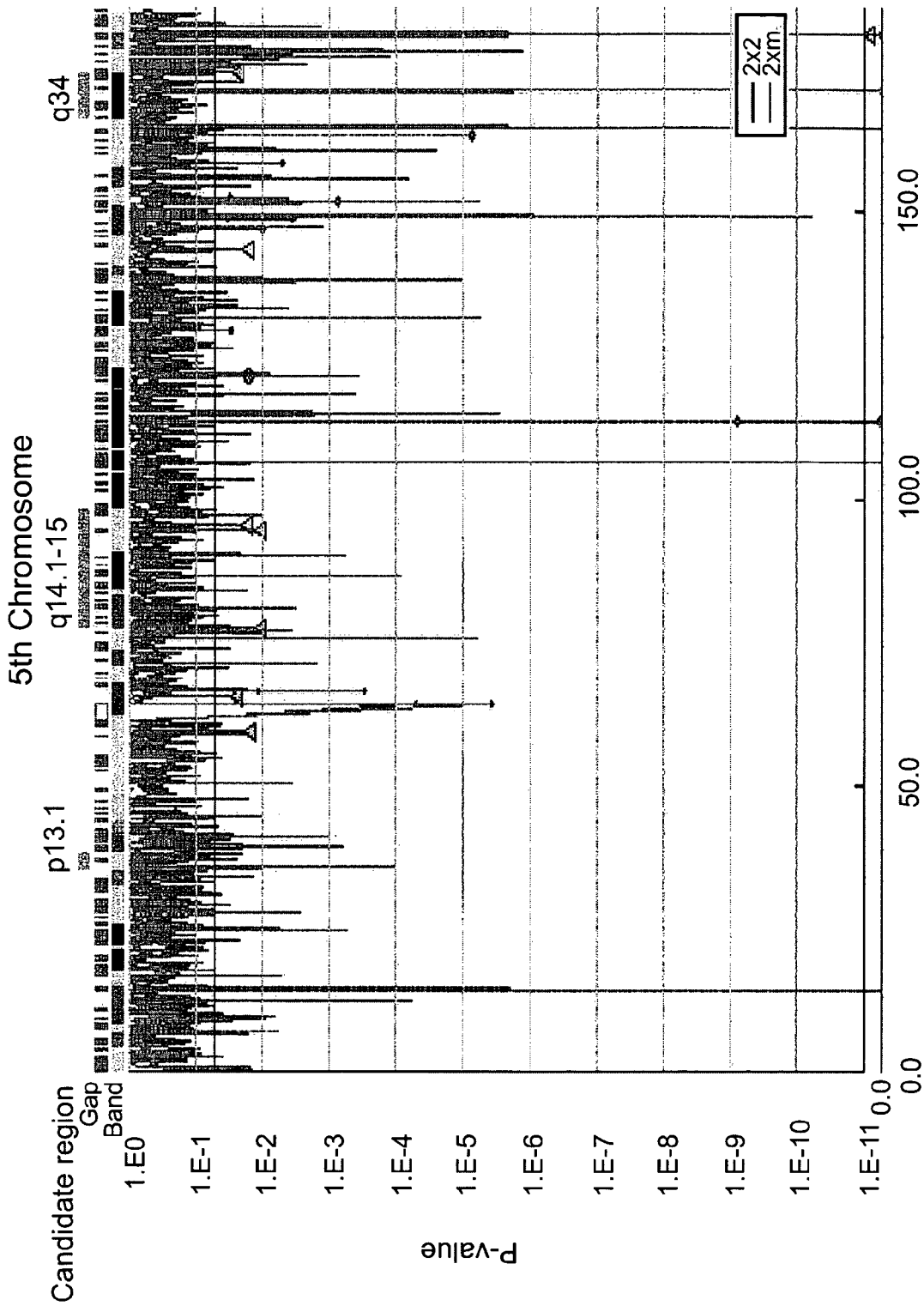
FIG. 8 shows a profile for the rheumatism susceptibility segment in the fifth chromosome analyzed using a method according to the present invention.
Figure 9:
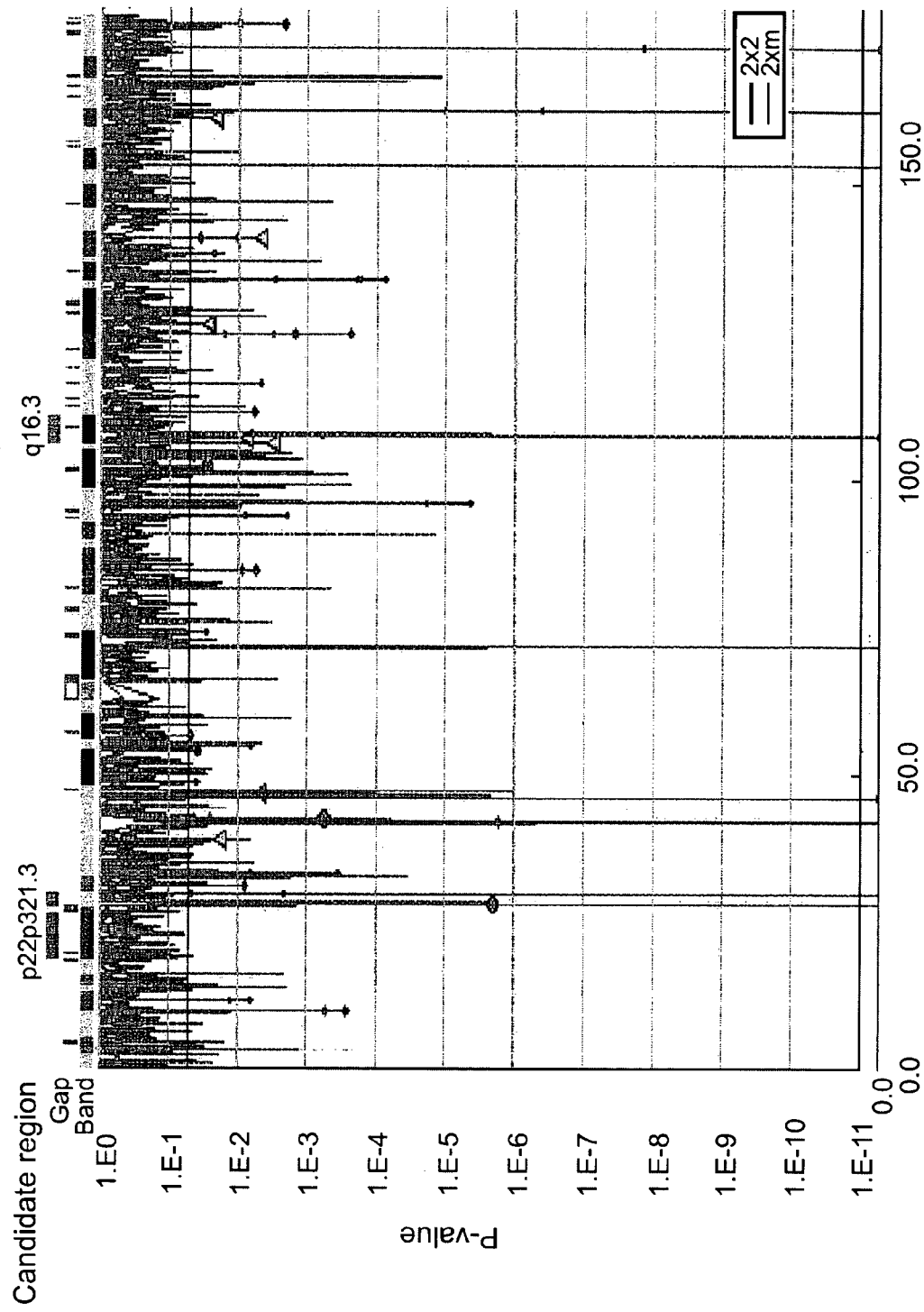
FIG. 9 shows a profile for the rheumatism susceptibility segment in the sixth chromosome analyzed using a method according to the present invention.
Figure 10:
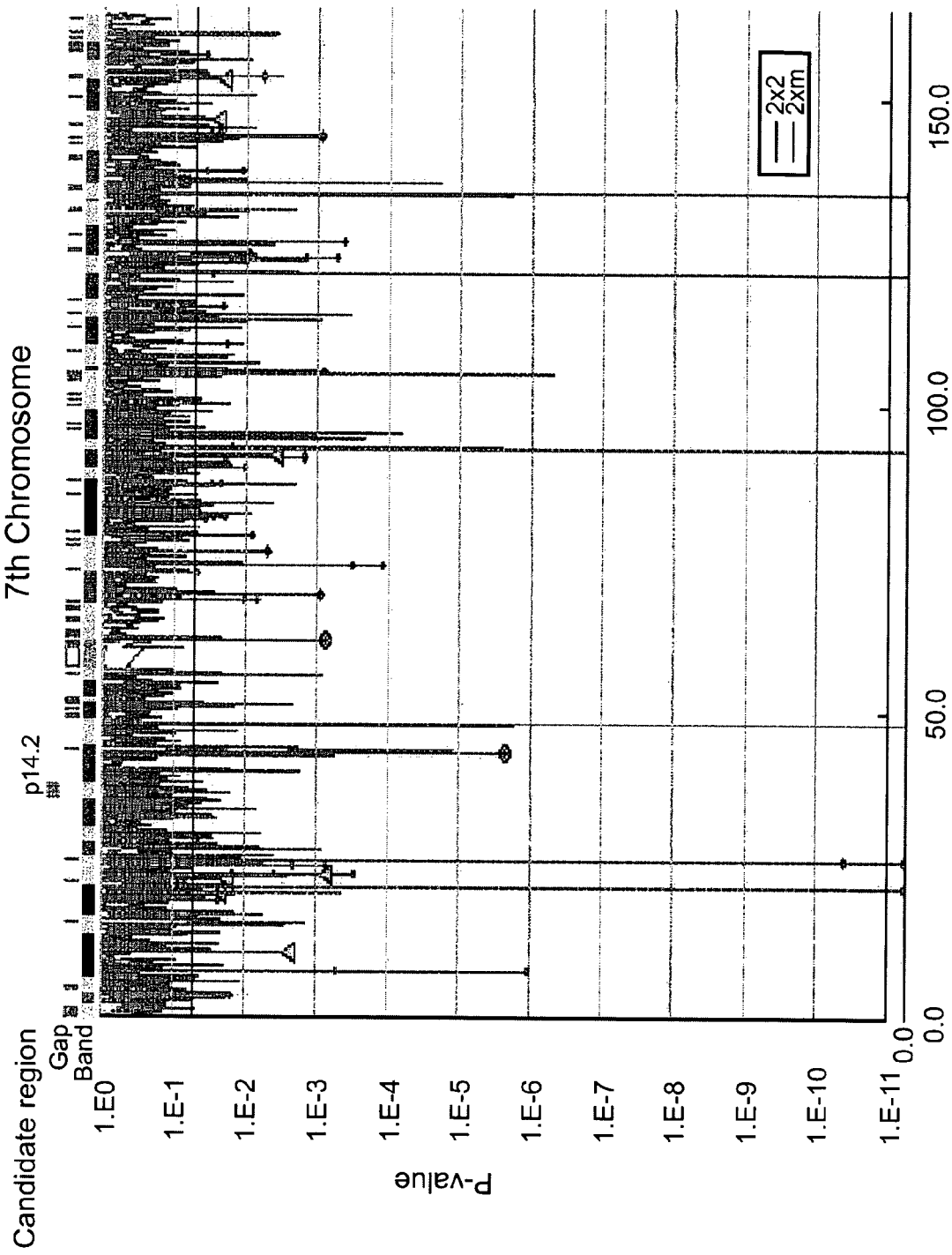
FIG. 10 shows a profile for the rheumatism susceptibility segment in the seventh chromosome analyzed using a method according to the present invention.
Figure 11:
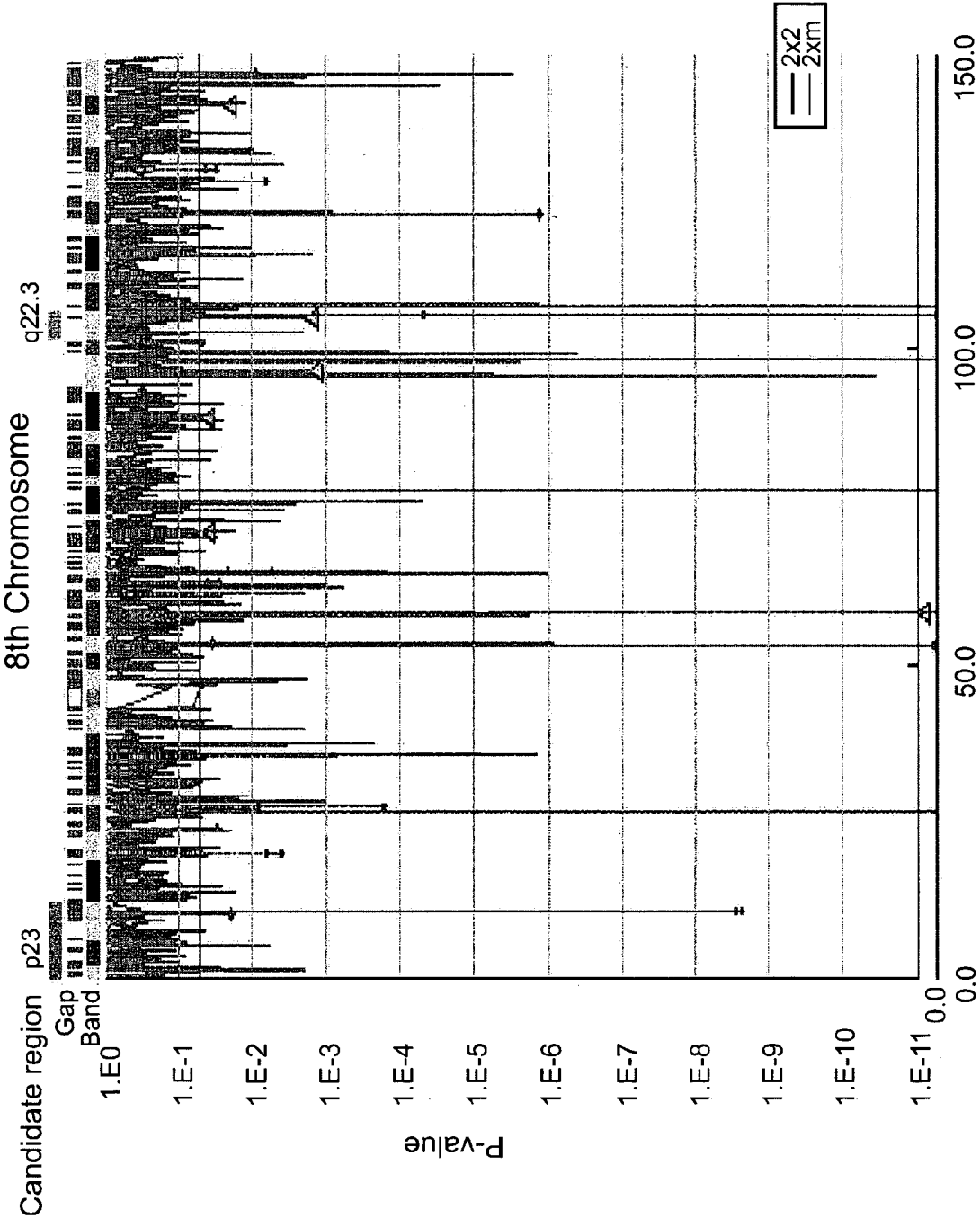
FIG. 11 shows a profile for the rheumatism susceptibility segment in the eighth chromosome analyzed using a method according to the present invention.
Figure 12:
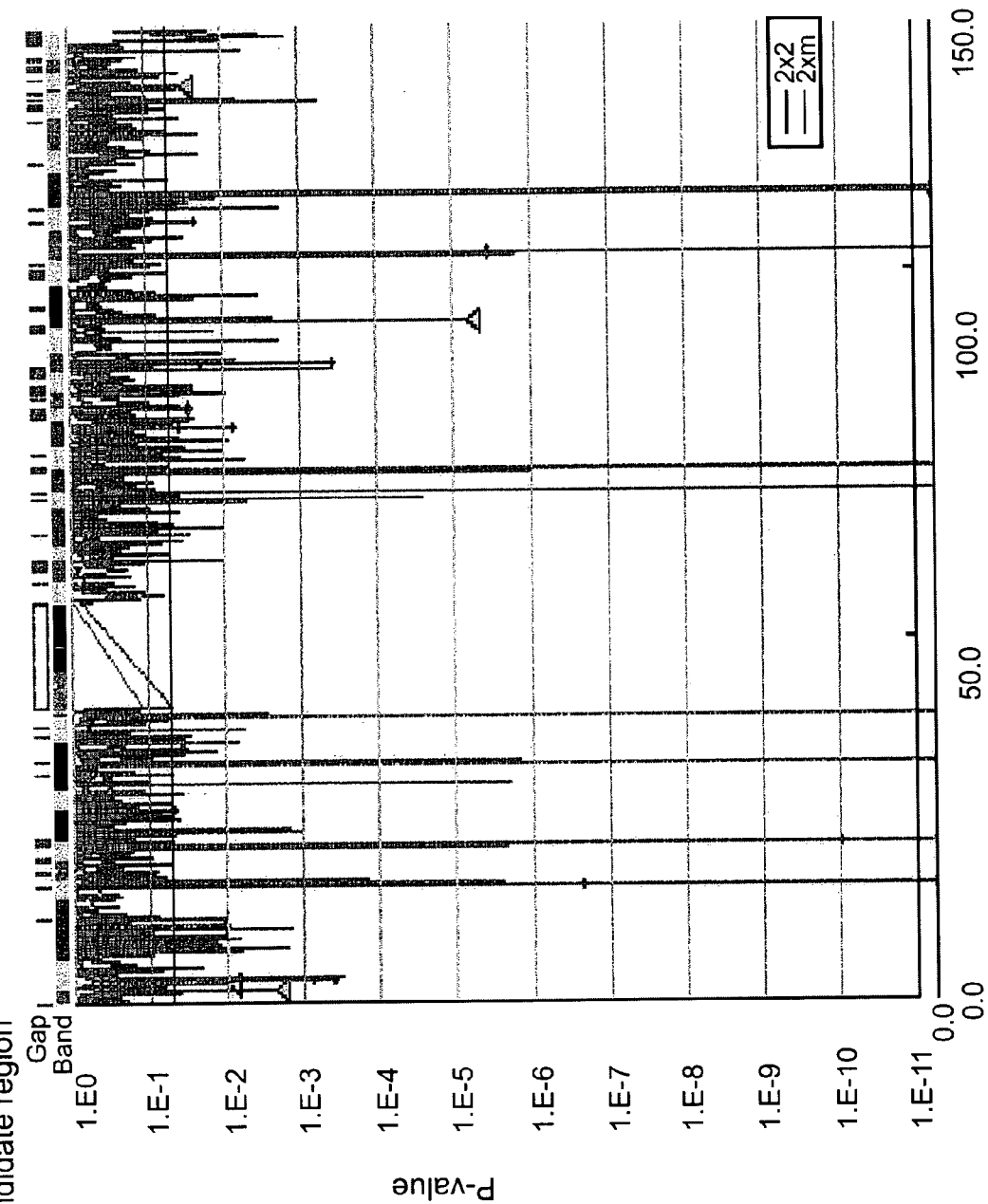
FIG. 12 shows a profile for the rheumatism susceptibility segment in the ninth chromosome analyzed using a method according to the present invention.
Figure 13:
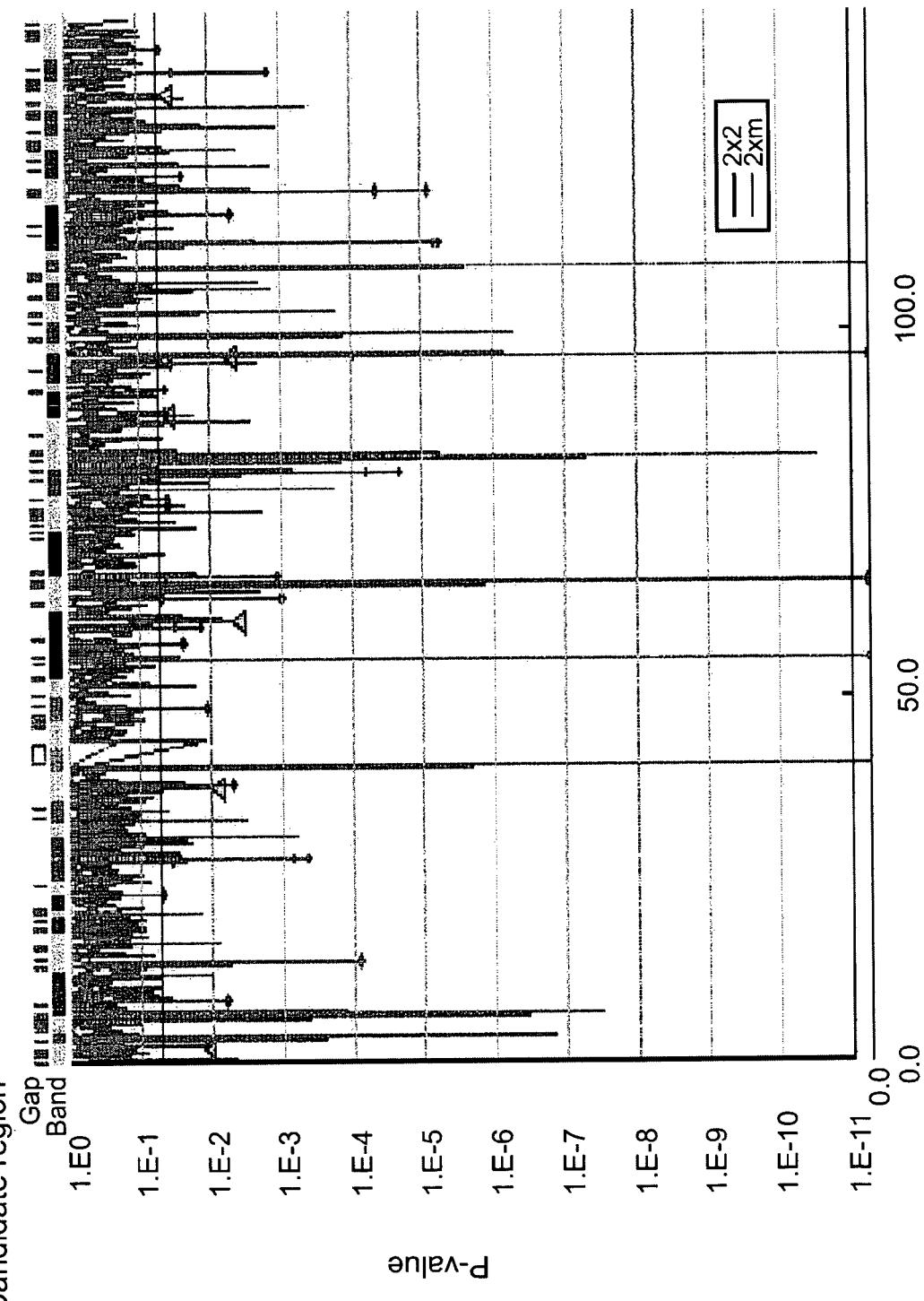
FIG. 13 shows a profile for the rheumatism susceptibility segment in the tenth chromosome analyzed using a method according to the present invention.
Figure 14:
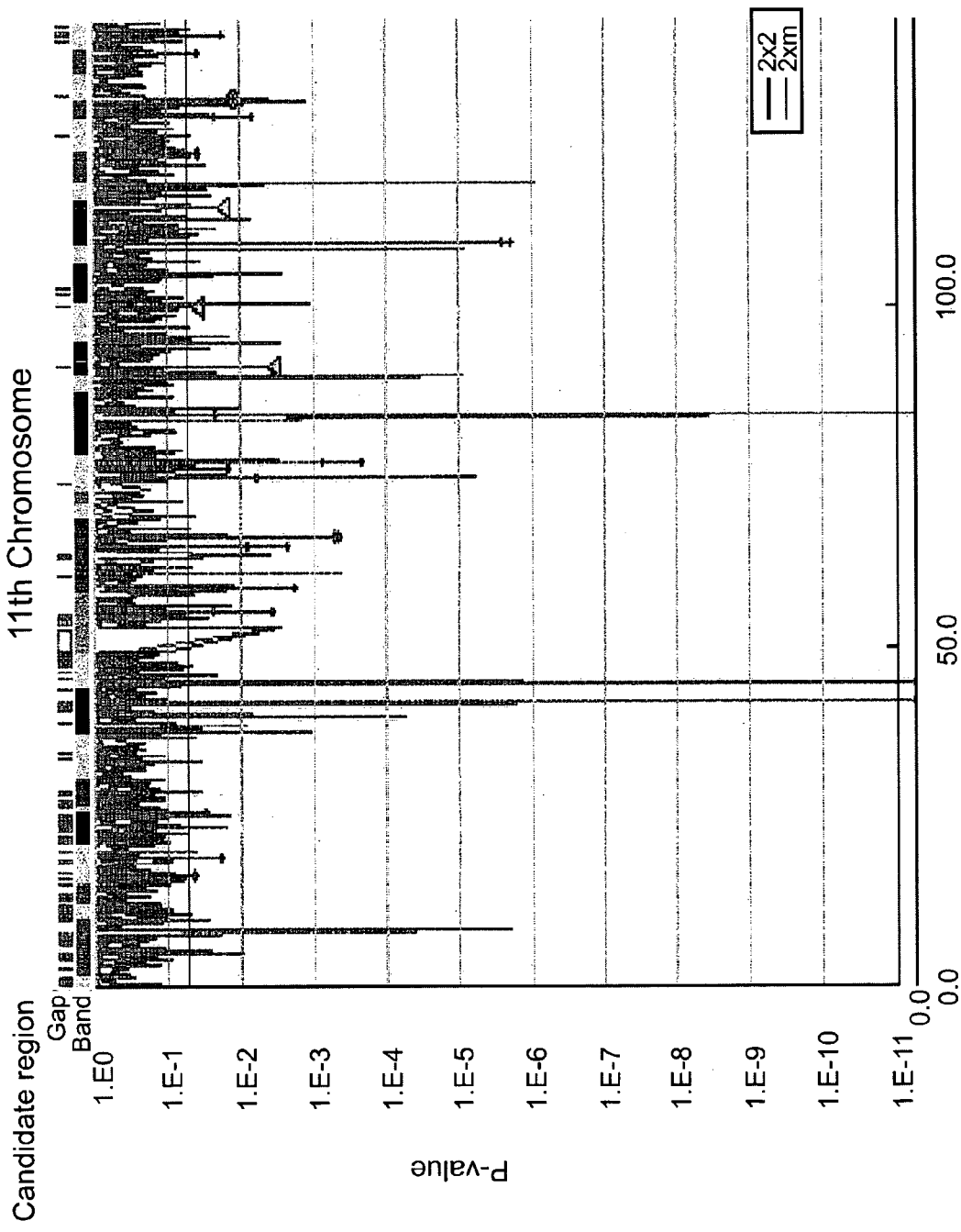
FIG. 14 shows a profile for the rheumatism susceptibility segment in the eleventh chromosome analyzed using a method according to the present invention.
Figure 15:
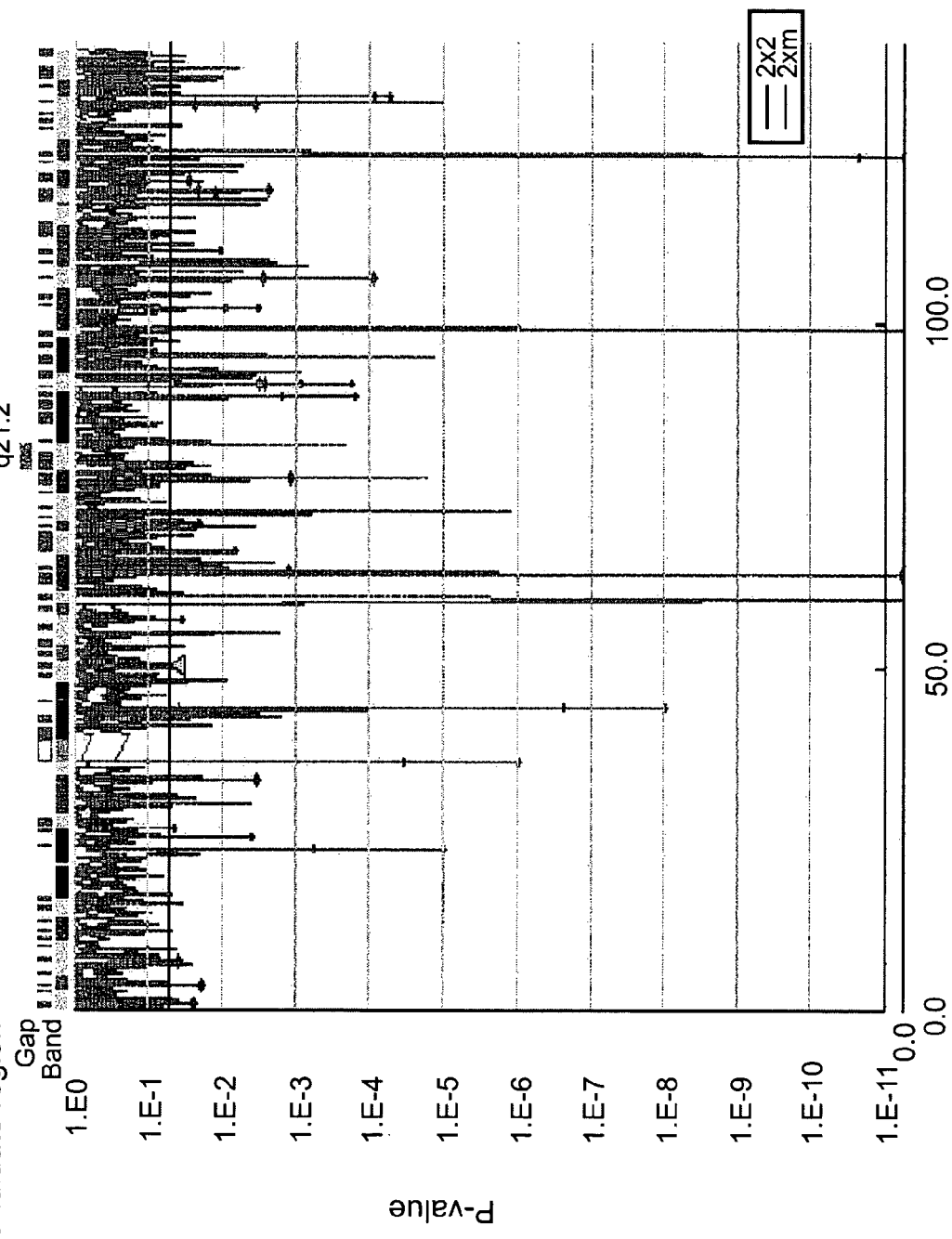
FIG. 15 shows a profile for the rheumatism susceptibility segment in the twelfth chromosome analyzed using a method according to the present invention.
Figure 16:
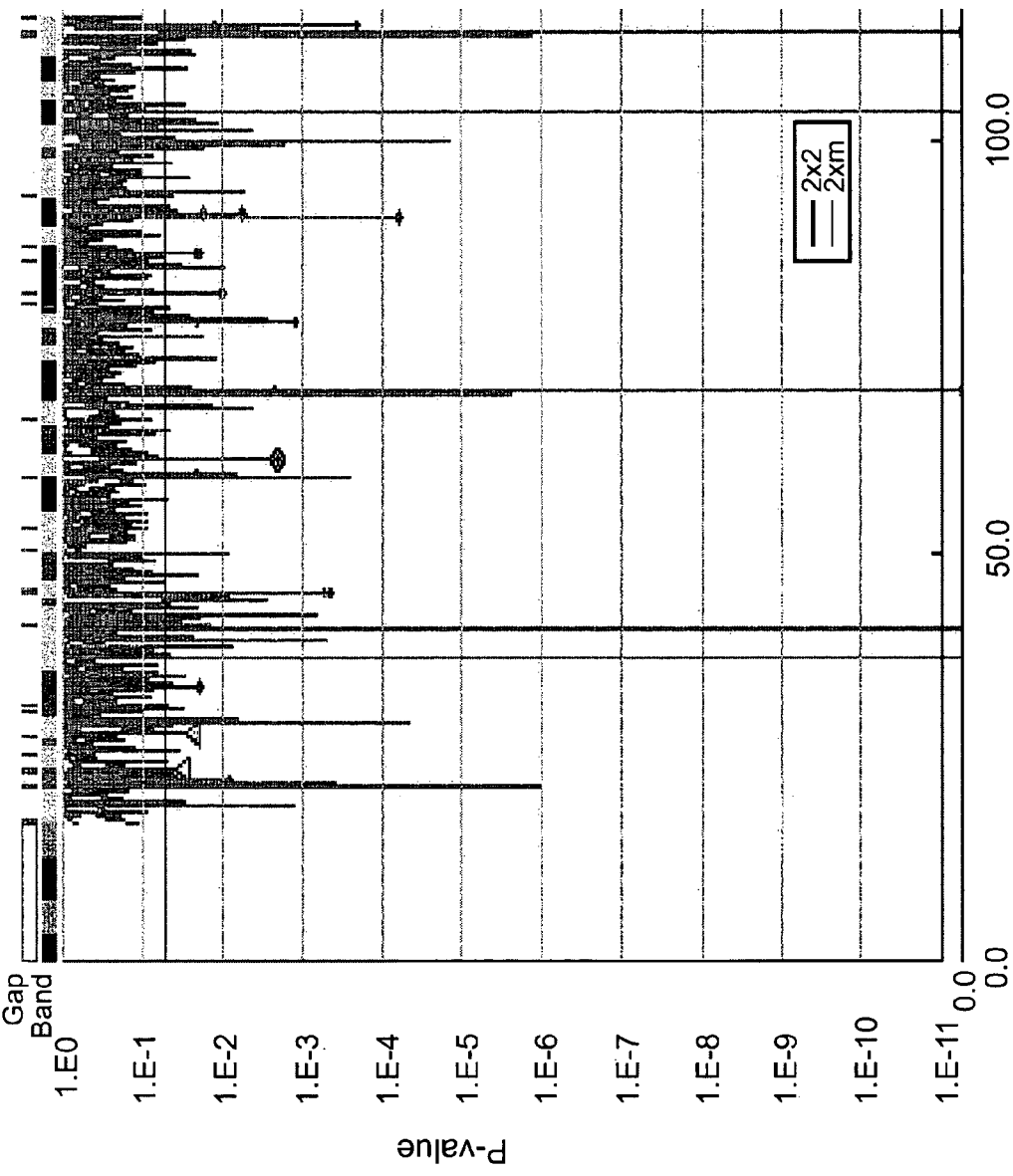
FIG. 16 shows a profile for the rheumatism susceptibility segment in the thirteenth chromosome analyzed using a method according to the present invention.
Figure 17:
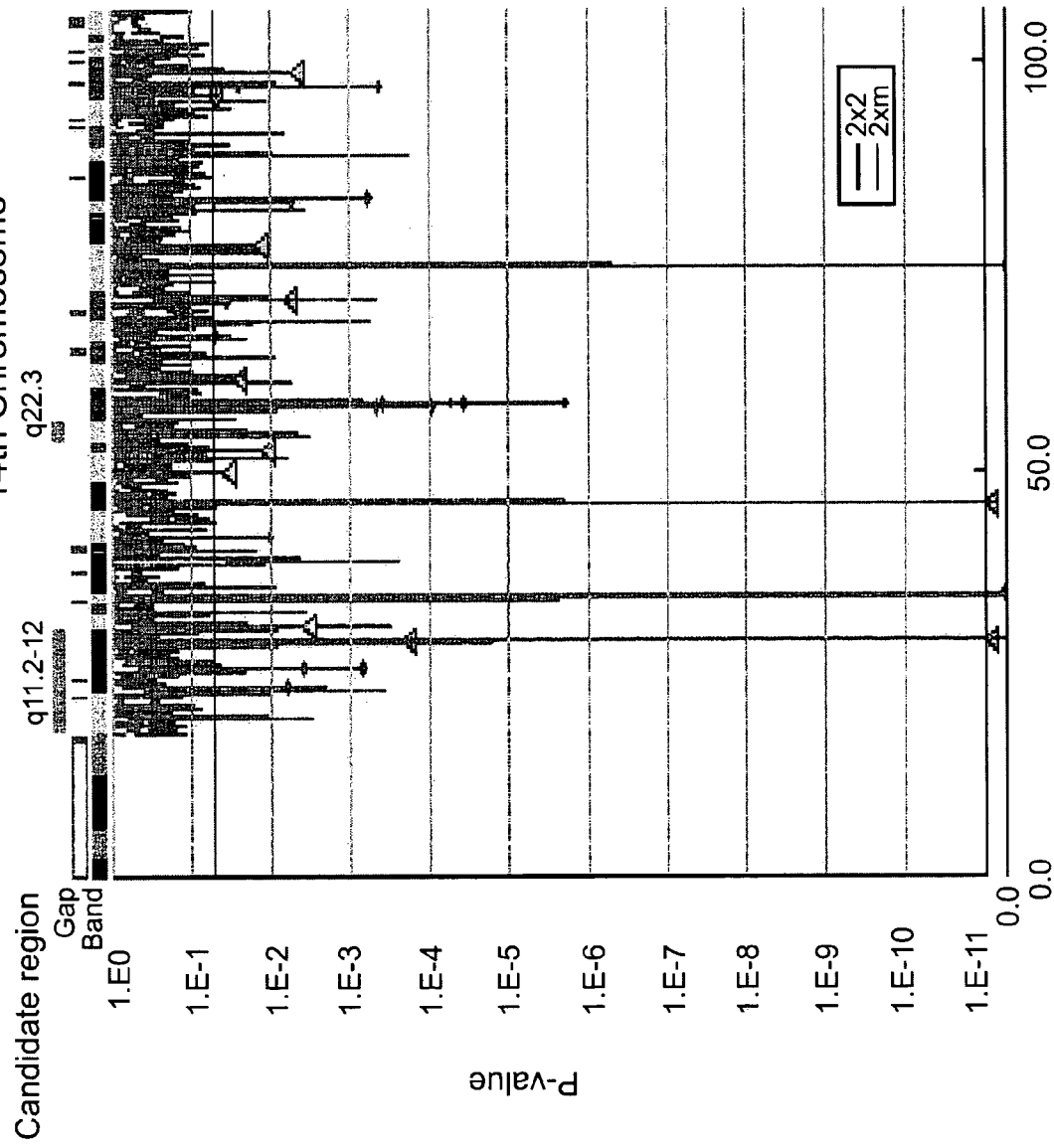
FIG. 17 shows a profile for the rheumatism susceptibility segment in the fourteenth chromosome analyzed using a method according to the present invention.
Figure 18:
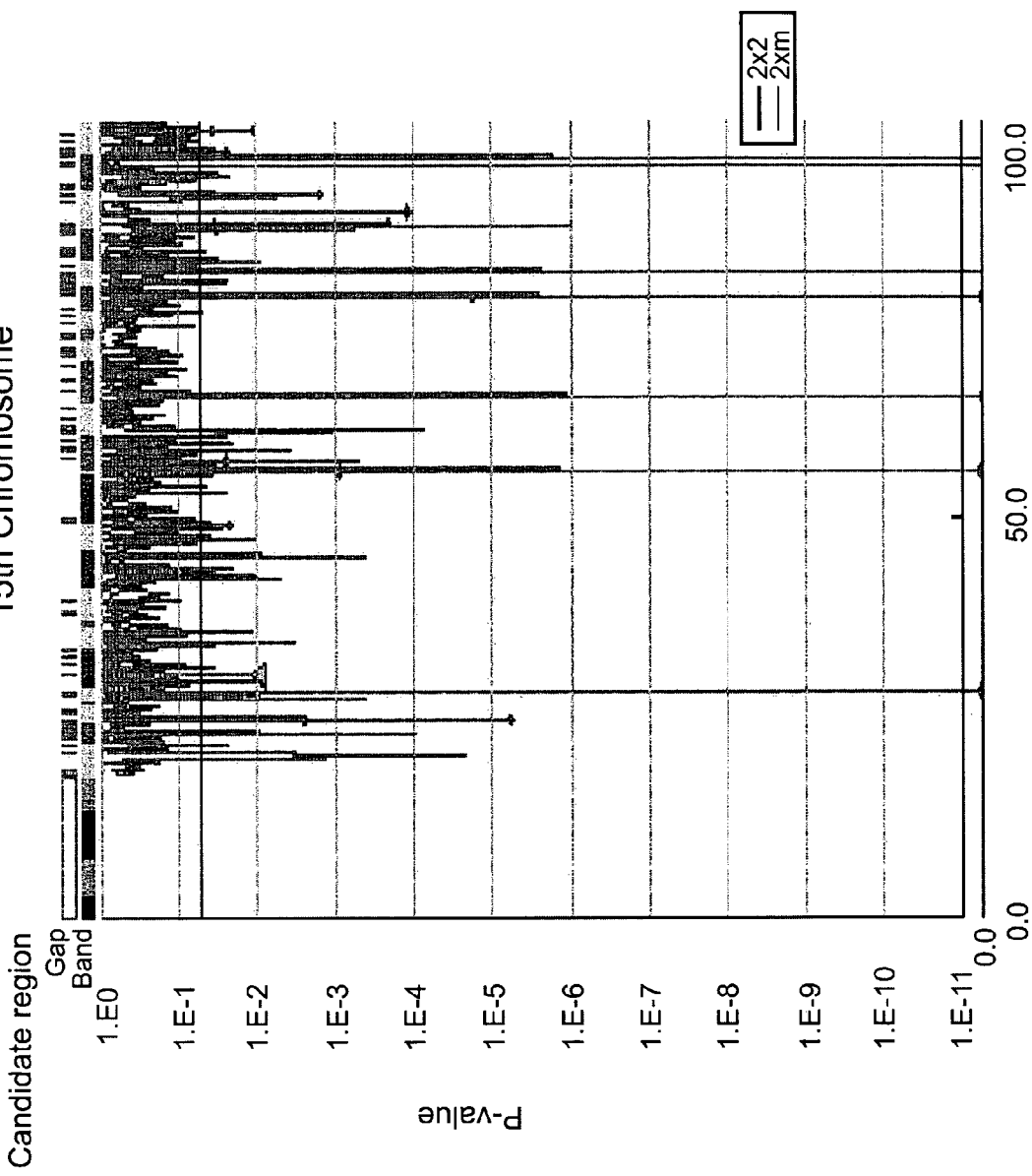
FIG. 18 shows a profile for the rheumatism susceptibility segment in the fifteenth chromosome analyzed using a method according to the present invention.
Figure 19:
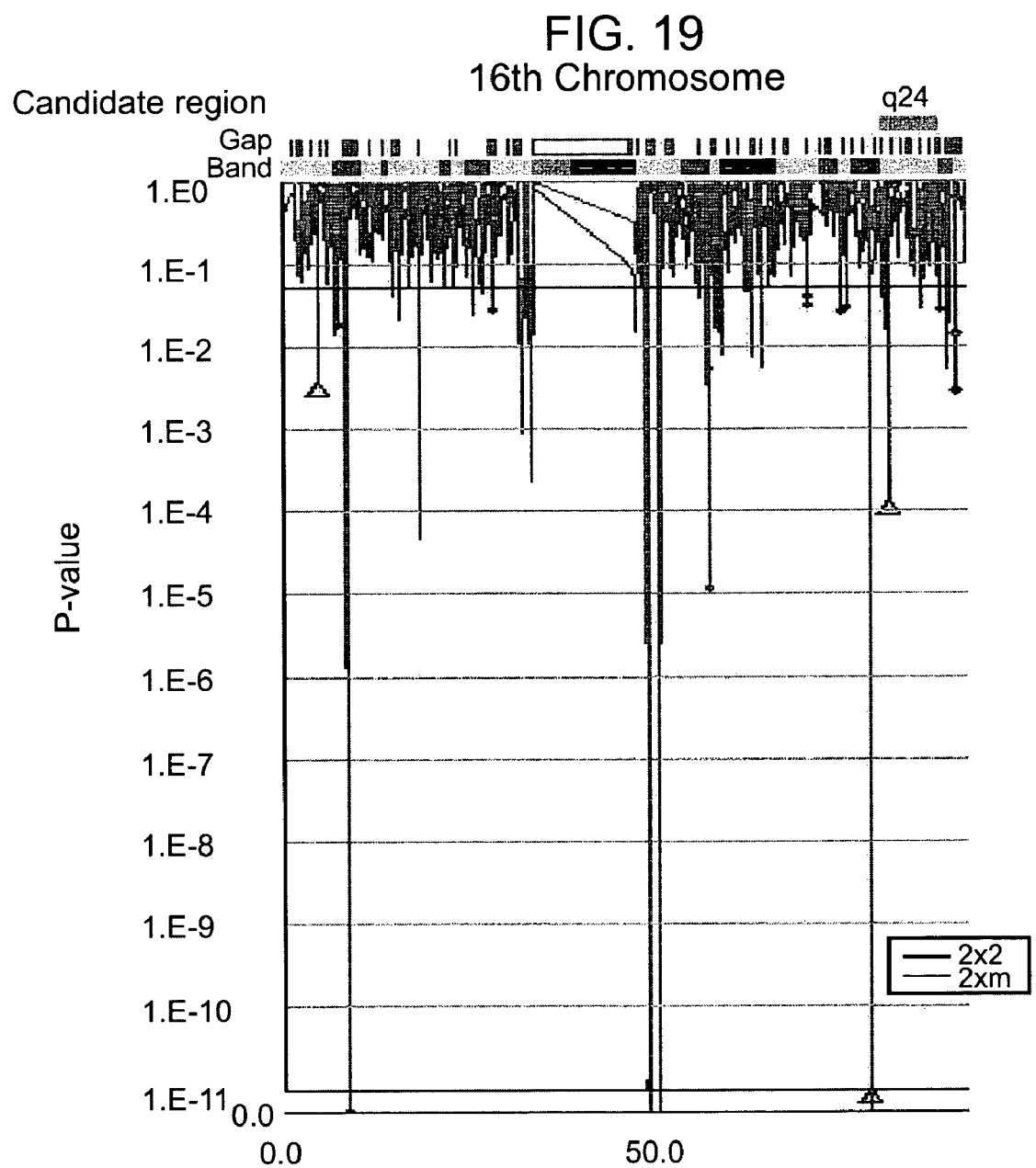
FIG. 19 shows a profile for the rheumatism susceptibility segment in the sixteenth chromosome analyzed using a method according to the present invention.
Figure 20:
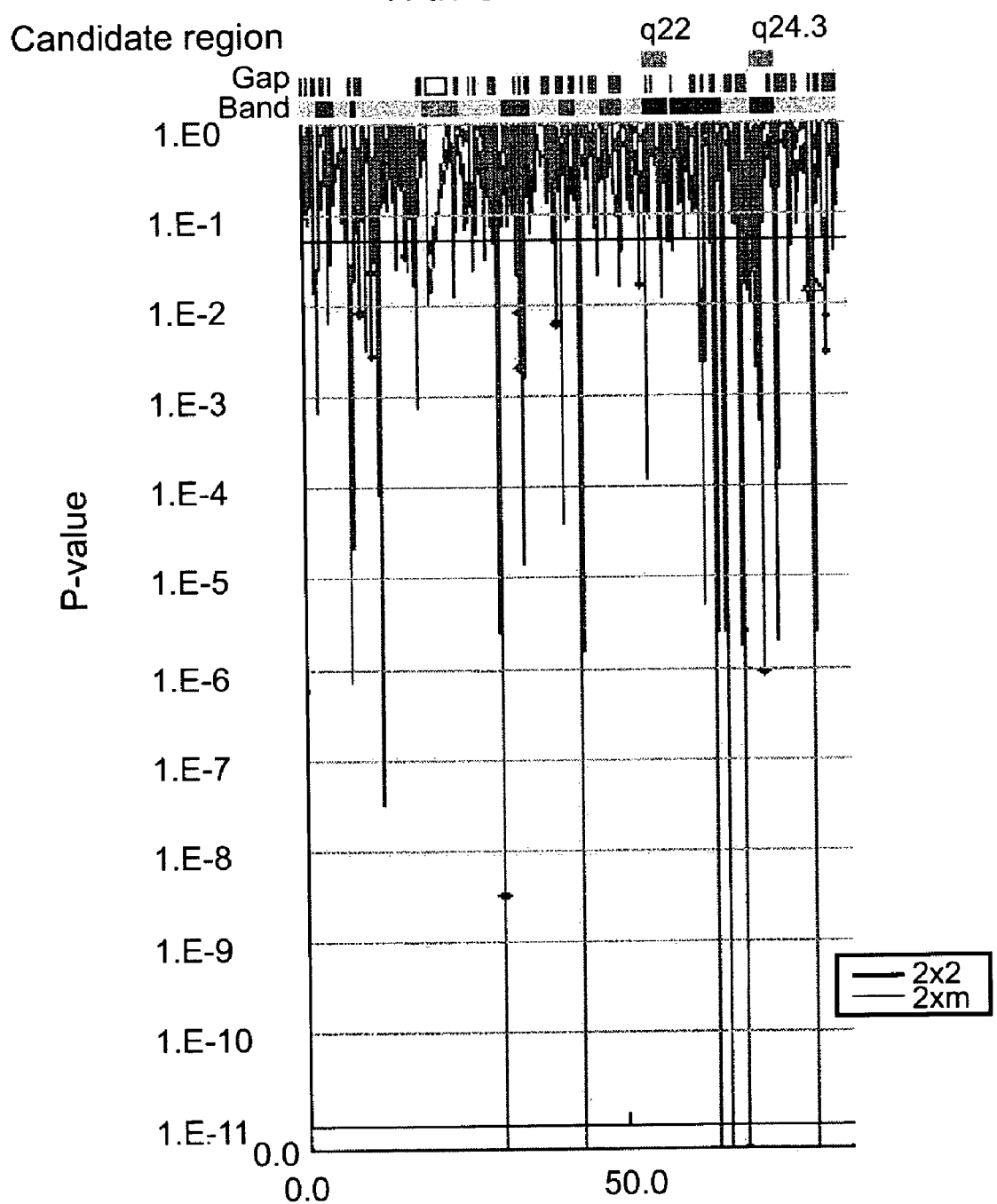
FIG. 20 shows a profile for the rheumatism susceptibility segment in the seventeenth chromosome analyzed using a method according to the present invention.
Figure 21:
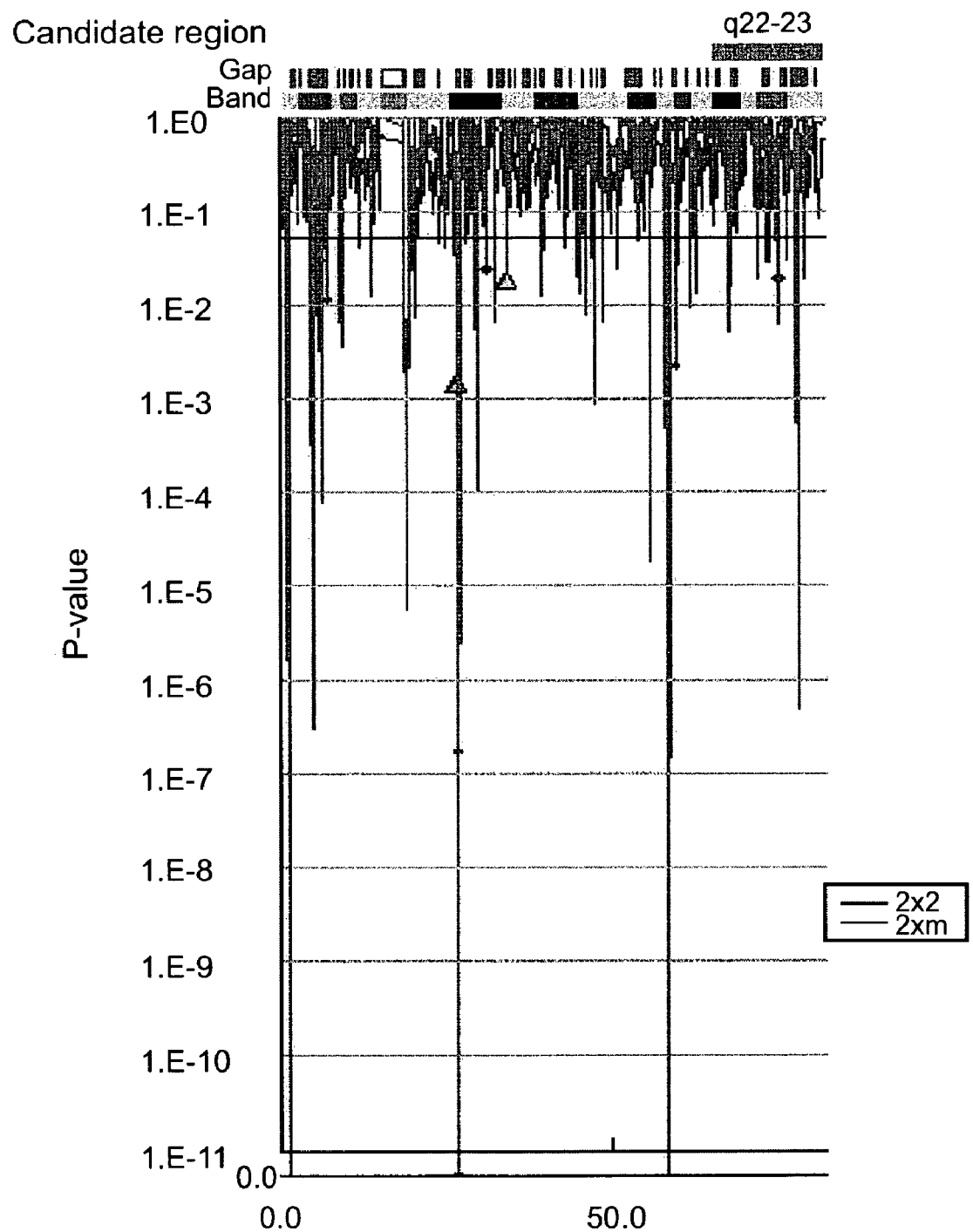
FIG. 21 shows a profile for the rheumatism susceptibility segment in the eighteenth chromosome analyzed using a method according to the present invention.
Figure 22:
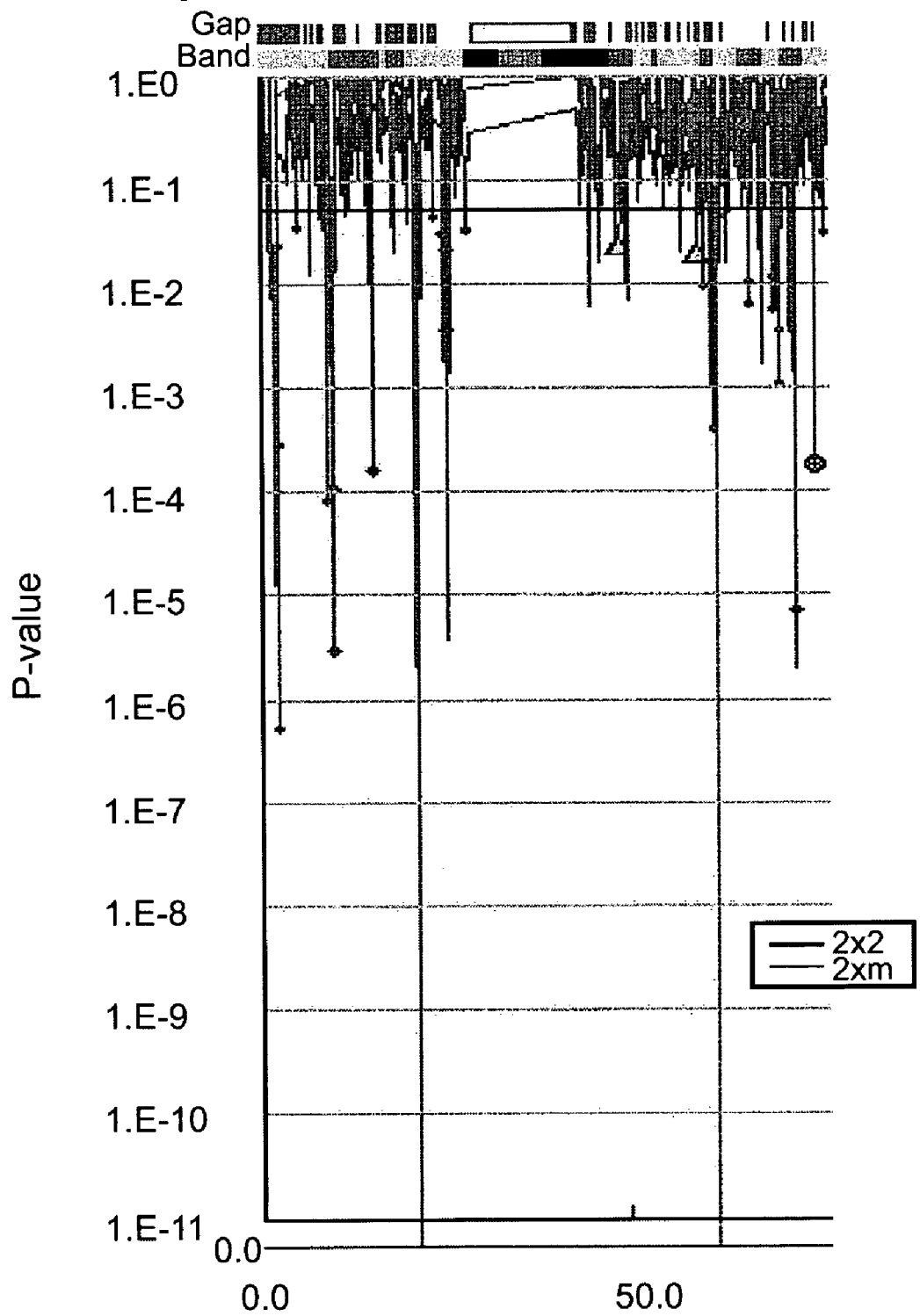
FIG. 22 shows a profile for the rheumatism susceptibility segment in the nineteenth chromosome analyzed using a method according to the present invention.
Figure 23:
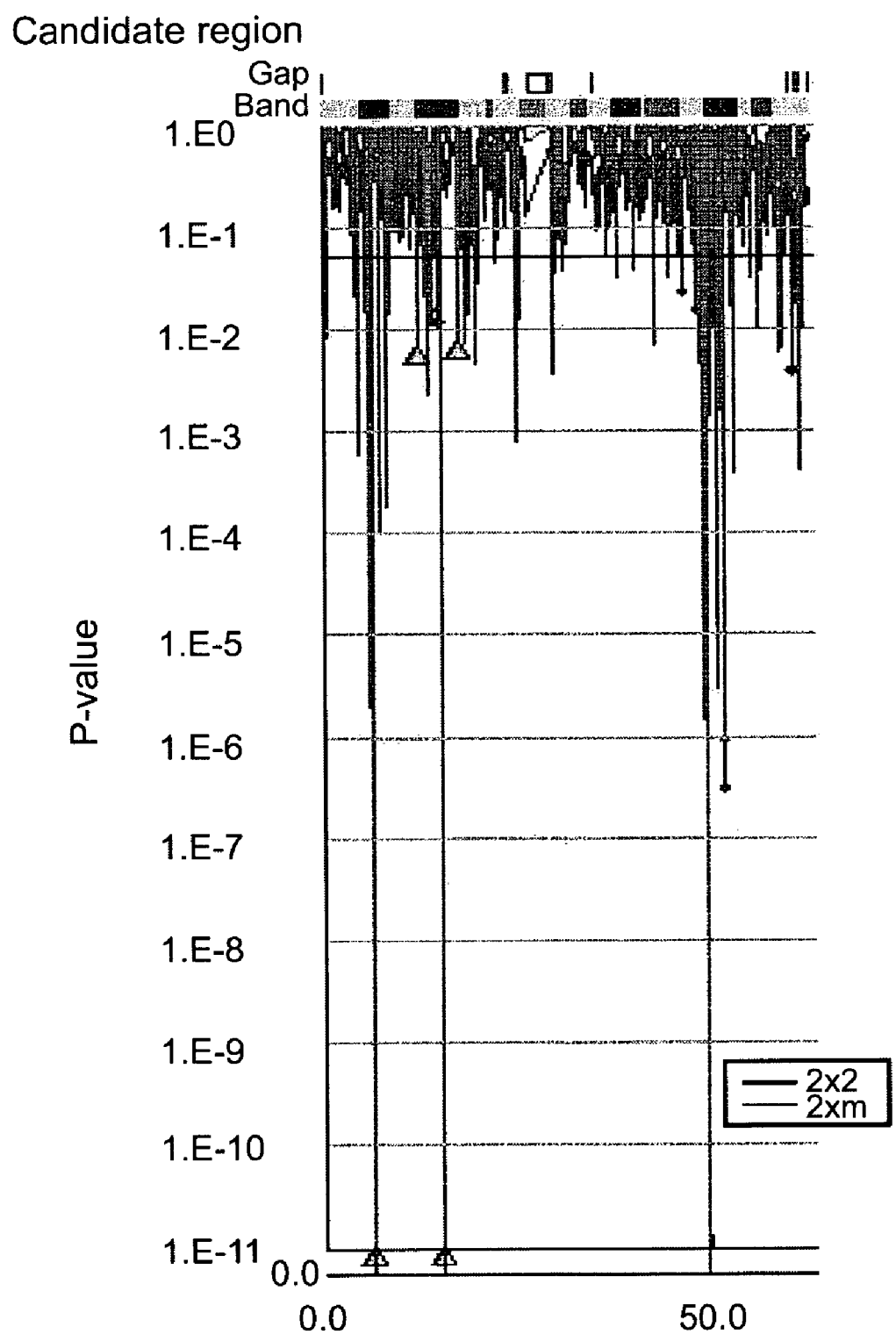
FIG. 23 shows a profile for the rheumatism susceptibility segment in the twentieth chromosome analyzed using a method according to the present invention.
Figure 24:
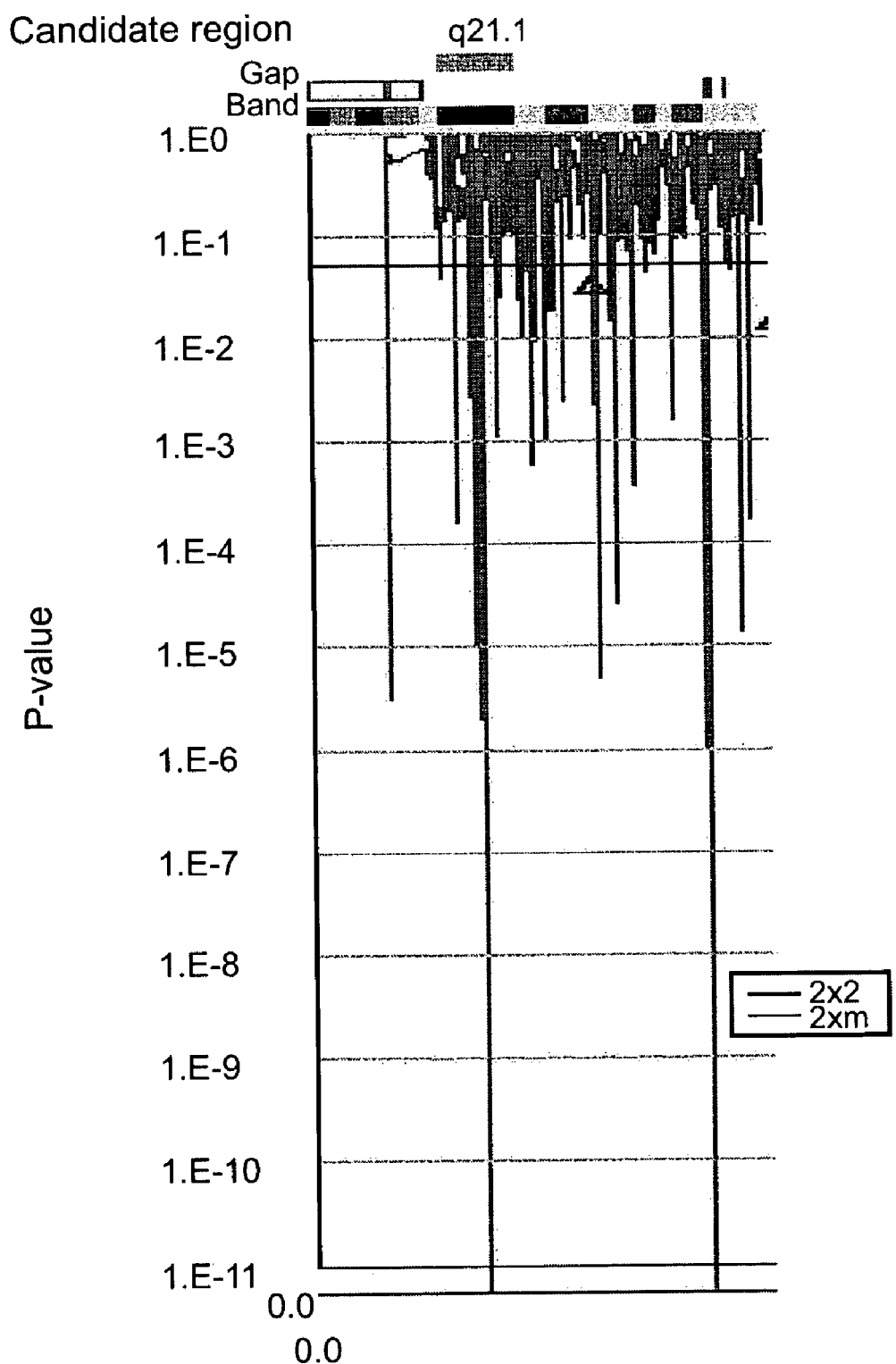
FIG. 24 shows a profile for the rheumatism susceptibility segment in the twenty-first chromosome analyzed using a method according to the present invention.
Figure 25:
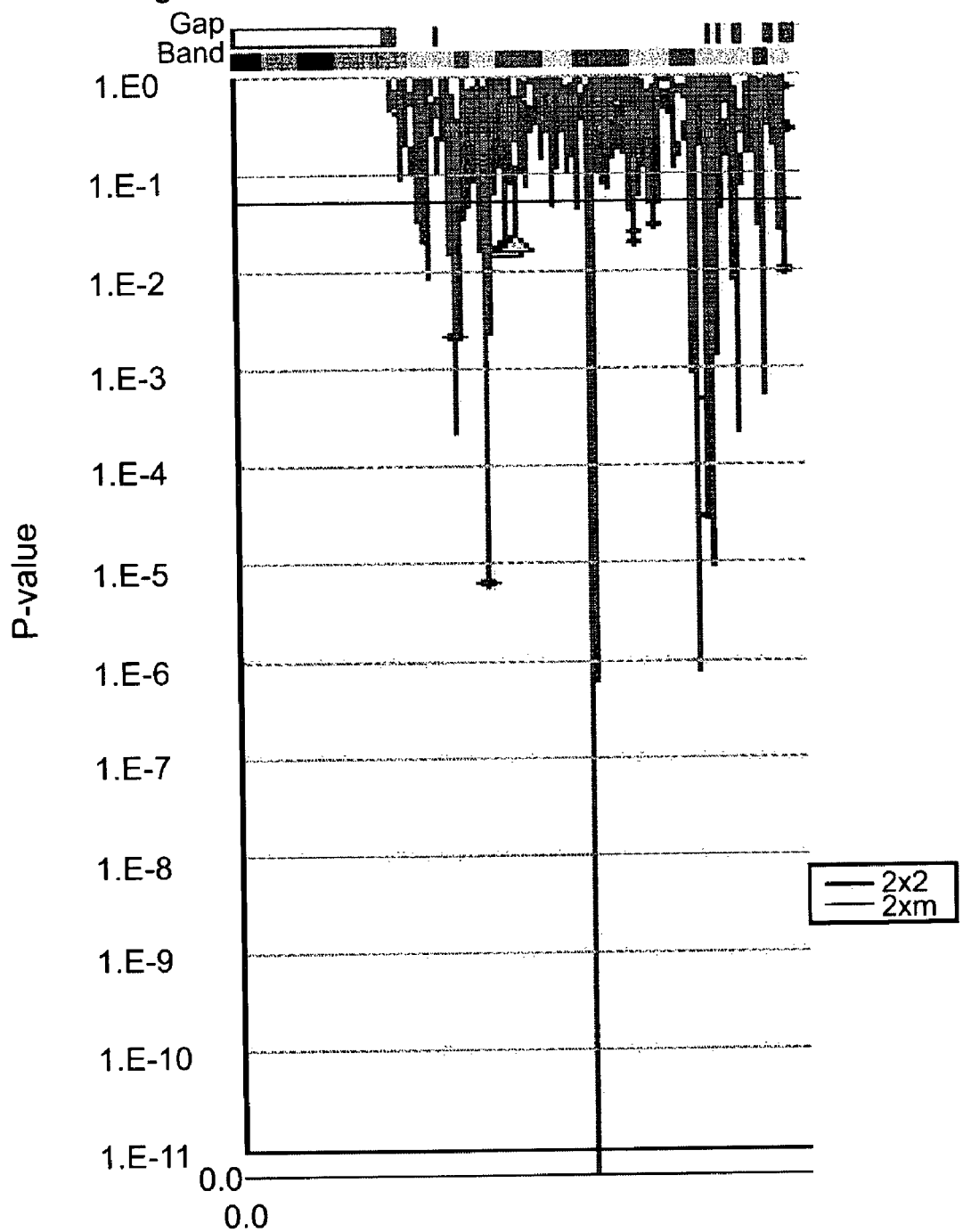
FIG. 25 shows a profile for the rheumatism susceptibility segment in the twenty-second chromosome analyzed using a method according to the present invention.

The result from performing the first screening is shown in FIG. 3. At this time, MS genetic polymorphism markers with correlation are selected through the chi-square test using a 2×m divided table and the Fisher's exact test using a 2×2 divided table. Comparison of the results from using 2×m and 2×2 divided tables show a difference in the number of markers, which indicates correlation. The test using the 2×2 divided table allows detection of the difference in each allele between the patients and the healthy subjects even for the observed markers with a high allele number.

Therefore, in the case where a specific allele and susceptibility gene indicate linkage disequilibrium, the test using the 2×2 divided table allows detection. On the other hand, in the case where there are differences in the allele frequencies on the whole between the patients and the healthy subjects, the test using the 2×m divided table allows thorough detection. Considering such statistical characteristics, an MS genetic polymorphism marker is selected for performing the second screening.

In the second screening, analysis of 102 markers that have been identified as positive by the first screening is carried out. Using other DNA samples, which are different from the DNA samples used for the first screening, the pooled DNA samples to be used for the second screening are prepared and a test is carried out.

Such a step-by-step analysis is expected to allow efficient decrease in false-positive without correcting the statistic threshold. According to the report by Barcellos et al., in the case of performing the first screening using genetic polymorphism markers throughout the genome, the detected number of the MS genetic polymorphism markers found positive is expected to be the total of 1500 false-positive markers (5% of all markers) and some of the true-positive markers. Performing the second screening In the same manner allows restriction of the number of the false-positives to 75 (5% of 1500). Determination due to Individual typing and/or TDT analysis or the like using other patient samples allow further decrease in the false-positives, thereby approaching identification of the susceptibility gene.

Analysis of 10 for the second screening showed 16 positive markers. Cornelis (1998) has reported about the linkage analysis of the first chromosome carried out for 114 paired incidence European Caucasians (Proc Natl Acad Sci USA. (1998) 95(18):10746-50. They have identified significant linkage regions in D1S228 (1p36-pter). Furthermore, Shiozawa at el. (1998) shows a significant linkage in 1p36 with a maximal lod score (MLS) being 3 or greater as the result from performing incidence pair analysis of 41 Japanese families (Int Immunol. (1998) 10(12):1891-5). Furthermore, Jawaheer at el. (2001) shows a significant linkage in D1S235 (1q43-44) as the result from performing incidence pair analysis of 257 families from the North American Rheumatoid Arthritis-Consortium (Am J Hum Genet. 2001 April;68(4): 927-36. Epub 2001 March 09.). On the other hand, Jawaheer at el. (2001) shows a significant linkage in D4S1647 (4q23-24) of the fourth chromosome (Am J Hum Genet. 2001 April; 68(4):927-36. Epub 2001 March 09.).). According to our results provided this time, positive MS genetic polymorphism markers are observed in the reported band regions.

Example 5

Analysis of Susceptibility Segment for Diseases Scattering in Entire Chromosome for Rheumatoid Arthritis Using the samples and method used in Example 4, the first and the second screening with 22,636 polymorphism microsatellites distributed throughout the chromosome as markers are performed. Moreover, the candidate segments restricted by the first and the second screening using samples of the 125 additional healthy subjects and samples of 125 additional patients for the third screening are subjected to an analysis throughout the genome or gene statistic analysis for individuals. As a result, as shown in FIGS. 4 to 26, a profile for the rheumatism susceptibility segment is identified in the first to the twenty-second chromosome except for the Y chromosome, and the X chromosome. The peaks in the figures indicate a given area of the chromosome that is associated with a susceptibility to the disease. These results are compared in quantity with the known candidate segments, and shown in Tables 4 to 6. As shown in Tables 4 to 6, three regions are known, and with a method herein, 22 regions are identified in the third screening step. Specifically, 19 additional candidate segments are identified.

TABLE 4

Correlation of known candidate segment with positiveness rate found by the present analysis

| | First screening | | |
|---|---|---|---|
| | No. of markers for analysis | No. of positive markers | No. of positive markers/1 Mb |
| Entire chromosome* | 22,636 | 2,504 | 0.811 |
| Known candidate segment | 1,843 | 160 | 0.664 |
| Other than candidate segment | 19,432 | 2,166 | 0.761 |

*Y chromosome is removed.

TABLE 5

Correlation of known candidate segment with positiveness rate found by the present analysis

| | Second screening | | |
|---|---|---|---|
| | No. of markers for analysis | No. of positive markers | No. of positive markers/1 Mb |
| Entire chromosome* | 2,204 | 117 | 0.038 |
| Known candidate segment | 145 | 30 | 0.125 |
| Other than candidate segment | 1,910 | 59 | 0.021 |

*Y chromosome is removed.

TABLE 6

Correlation of known candidate segment with positiveness rate found by the present analysis

| | Third Screening | | |
|---|---|---|---|
| | No. of markers for analysis | No. of positive markers | No. of positive markers/1 Mb |
| Entire chromosome* | 53 | 22 | 0.007 |
| Known candidate segment | 8 | 3 | 0.012 |
| Other than candidate segment | 45 | 19 | 0.006 |

*Y chromosome is removed.

Utility of the Invention

The method according to the present invention allows effective genetic correlation analysis throughout a genome irrelevant to race since DNA sequences including microsatellite genetic polymorphism markers prepared (SEQ ID NOS:1 to 27088) have genetic polymorphism, where 95% or greater of them are shared by all races. Analysis of 2471 markers of the first and the fourth chromosome for, for example, the rheumatoid arthritis is carried out, and since the first screening results in finding 102 markers positive, the second screening is then carried out. As a result, 16 markers are found positive (i.e., 6 markers in the first chromosome and 10 markers in the fourth chromosome).

Candidate segments in the susceptibility gene identified are subjected to SNP analysis, which allows identification of the susceptibility gene. Moreover, in addition to usage of the microsatellite genetic polymorphism markers included DNA sequences throughout the genome (SEQ ID NOS:1 to 27088), detailed analysis of only a specific chromosome for a phenotype of a disease or the like is carried out using the sequence numbers 1 to 27088, which allows higher speed and further accurate identification of the genes existing in the susceptibility segment for a disease.

Genes isolated by the method of this invention, proteins encoded by these genes, antibodies against these proteins, and/or polynucleotides containing at least 15 nucleotides complementary to one of the strands of these genes or to their complementary strands may be used for genetic screening and gene therapy. Furthermore, a pathogenic gene of a disease isolated by the method of this invention, a protein encoded by the gene, an antibody against the protein and/or a polynucleotide containing at least 15 nucleotides-complementary to one of the strands of this gene or to its complementary strand may be used for testing, preventing, and/or treating the disease.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US07510834B2). An electronic copy of the "Sequence Listing" will also be available from the USPTO upon request and payment of the fee set forth in 37 CFR 1.19(b)(3).

What is claimed is:

1. A method of identifying a DNA sequence fragment comprising a microsatellite in a human genomic region in which a gene associated with a phenotype exists, comprising:
   selecting a combination of DNA sequences comprising SEQ ID Nos. 1-27088, wherein each of the sequences comprises a microsatellite genetic polymorphism marker;
   collecting DNA samples from subjects affected with said phenotype and control subjects not affected with said phenotype;
   performing polymerase chain reactions (PCR) on the DNA samples using forward primers consisting of 15-25 nucleotides wherein the forward primers consist of the same nucleotide sequence as the sequence extending in the 3'-direction from the 5'-terminus of each of the DNA sequences in said combination and reverse primers consisting of 15-25 nucleotides wherein the reverse primers consist of the sequence complementary to the sequence extending in the 5'-direction from the 3'-terminus of each of the DNA sequences in said combination to produce DNA sequence fragments, wherein each of said DNA sequence fragments comprises a microsatellite genetic polymorphism marker;
   analyzing alleles of the microsatellite genetic polymorphism markers of said DNA sequence fragments; and
   statistically comparing allele frequencies observed in the DNA sequence fragments produced from the affected subjects with those observed in the DNA sequence fragments produced from the control subjects to identify microsatellite polymorphism markers found positive whose allele frequencies observed in the DNA sequence fragments produced from the affected subjects are statistically significantly different from the allele frequencies observed in their corresponding DNA sequence fragments produced from the control subjects, wherein the DNA fragments comprising at least one microsatellite polymorphism marker found positive are in a human genomic region in which a gene associated with a phenotype exists.

2. The method according to claim 1, further comprising the step of mixing the DNA samples obtained from the subjects affected with the phenotype to provide pooled samples for affected subjects and mixing the DNA samples obtained from the control subjects not affected with the phenotype to provide pooled DNA samples for control subjects before performing the polymerase chain reaction.

3. The method according to claim 1, wherein the DNA sequence fragments produced by PCR comprise all or a part of the DNA sequences of SEQ ID Nos: 1-27088.

4. The method according to claim 1, wherein said analyzing of alleles of the microsatellite genetic polymorphism markers is carried out using a DNA chip and a mass spectrometer.

5. A method of identifying a DNA sequence fragment comprising a microsatellite in a human genomic region according to claim 1, further comprising:
   selecting secondary DNA sequences containing at least one microsatellite polymorphism marker found positive through the method of claim 1 from the combination of DNA sequences comprising SEQ ID Nos. 1-27088;
   collecting DNA samples from affected subjects different from the subjects affected with the phenotype of claim 1 and control subjects different from the control subjects of claim 1;
   performing polymerase chain reaction (PCR) on the DNA samples using forward primers consisting of 15-25 nucleotides wherein the forward primers consist of the same nucleotide sequence as the sequence extending in the 3'-direction from the 5'-terminus of each of the secondary DNA sequences and reverse primers consisting of 15-25 nucleotides wherein the reverse primers consist of the sequence complementary to the sequence extending in the 5'-direction from the 3'-terminus of each of the secondary DNA sequences to produce secondary DNA sequence fragments;
   analyzing alleles of the microsatellite genetic polymorphism markers of said secondary DNA sequence fragments, and
   statistically comparing allele frequencies observed in the secondary DNA sequence fragments produced from the affected subjects with those observed in the secondary DNA sequence fragments produced from the control subjects to identify microsatellite polymorphism markers found true-positive whose allele frequencies observed in the secondary DNA sequence fragments produced from the affected subjects are statistically significantly different from allele frequencies observed in their corresponding secondary DNA sequence fragments produced from the control subjects, wherein the secondary DNA fragments comprising at least one microsatellite polymorphism marker found true-positive are regarded as a region in which a pathogenic gene or a gene relating to human phenotypes associated with a genetic factor exists with higher probability.

6. The method according to claim 1, further comprising:
   analyzing said DNA sequence fragments comprising at least one microsatellite polymorphism marker found positive through the method of claim 1, based on allele frequency of known single nucleotide polymorphisms.

7. The method according to claim 5, further comprising:
   analyzing said DNA sequence fragments comprising at least one microsatellite polymorphism marker found true-positive through the method of claim 5, based on allele frequency of known single nucleotide polymorphisms.

* * * * *